(12) United States Patent
Dapprich et al.

(10) Patent No.: US 11,821,023 B2
(45) Date of Patent: Nov. 21, 2023

(54) METHOD FOR CAPTURING LONG POLYNUCLEOTIDES FOR SEQUENCING SPECIFIC GNOMIC REGIONS

(71) Applicant: Generation Biotech, LLC, Lawrenceville, NJ (US)

(72) Inventors: Johannes Dapprich, Lawrenceville, NJ (US); Karl P. Dresdner, Jr., Haddonfield, NJ (US); Richard R. McKay, East Windsor, NJ (US)

(73) Assignee: GENERATION BIOTECH, LLC, Lawrenceville, NJ (US)

( * ) Notice: Subject to any disclaimer, the term of this patent is extended or adjusted under 35 U.S.C. 154(b) by 646 days.

(21) Appl. No.: 16/501,730

(22) Filed: May 29, 2019

(65) Prior Publication Data
US 2020/0080130 A1 Mar. 12, 2020

Related U.S. Application Data

(60) Provisional application No. 62/763,015, filed on May 30, 2018.

(51) Int. Cl.
*C12Q 1/68* (2018.01)
*C12Q 1/6806* (2018.01)
*G01N 33/543* (2006.01)

(52) U.S. Cl.
CPC ..... *C12Q 1/6806* (2013.01); *G01N 33/54326* (2013.01)

(58) Field of Classification Search
None
See application file for complete search history.

(56) References Cited

U.S. PATENT DOCUMENTS

| 7,057,026 B2 | 6/2006 | Barnes |
| 8,465,925 B2 | 6/2013 | Dapprich et al. |
| 9,103,827 B2 * | 8/2015 | Dapprich ........... G01N 33/6875 |

(Continued)

OTHER PUBLICATIONS

Han et al. (Nature Nanotechnology, 2010, vol. 5, p. 712-717) (Year: 2010).*

(Continued)

*Primary Examiner* — Stephanie K Mummert
(74) *Attorney, Agent, or Firm* — MEAGHER EMANUEL LAKS GOLDBERG & LIAO, LLP

(57) ABSTRACT

The invention relates to methods for capturing a polynucleotide comprising a DNA target segment from a population of polynucleotide molecules using a rotation of a magnetic field to move streptavidin-labeled magnetic beads relative to a buffered liquid medium to increase the probability of capturing and preventing damage to a long polynucleotide comprising a DNA target segment. The methods may use a rotation of the magnetic field relative to the mixture or a rotation of the mixture relative to the magnetic field for causing magnetic bead rotation in the buffered liquid medium and increasing the binding of biotinylated nucleotides of an extended polynucleotide primer to streptavidin-labeled magnetic beads, and winding or condensation of a polynucleotide onto the streptavidin-labeled magnetic beads to prevent damage to the long polynucleotide comprising a DNA target segment.

22 Claims, 17 Drawing Sheets

Specification includes a Sequence Listing.

Counterclockwise rotation of homogeneous H-field by about 50°

(56) References Cited

U.S. PATENT DOCUMENTS

2001/0031467 A1     10/2001    Dapprich et al.
2012/0100546 A1*   4/2012    Lowery, Jr. ............ C12Q 1/689
                                                                       435/6.15

OTHER PUBLICATIONS

Litos et al. (Anal. Chem, 2007, 79, p. 395-402) (Year: 2007).*
Briggs et al. (Methods in Molecular Biology, 2011, vol. 772, Chapters, p. 145-154) (Year: 2011).*
Fei et al. (Rapid Commun Mass Spectrom, 2000, 14, 950-959) (Year: 2000).*
Torelli et al. (Small, 2014, No. 14, p. 2918-2926) (Year: 2014).*
Ganji et al., "Real-time imaging of DNA loop extrusion by condensin", Science, vol. 360, Issue 6384, 102-105, 2018.
Larson et al., "Liquid droplet formation by HP1α suggests a role for phase separation in heterochromatin", Nature, vol. 547, pp. 236-240, Jul. 13, 2017.
Rothemund, "Folding DNA to create nanoscale shapes and patterns", Nature, vol. 440, 297-302, Mar. 16, 2006.
Bauer et al., "Bridged cobalt amine complexes induce DNA conformational changes effectively", J Inorg Biochem, vol. 68, No. 2, pp. 129-135, 1997.

\* cited by examiner

Fig. 1

Uses For Targeted Long Read Sequences of a DNA or RNA Sample.

- Analysis of liquid biopsies, circulating tumor cells, microvesicles, exosomes or cell-free nucleic acids for precision medicine
- Immuno-oncology
- Treating sepsis
- Predicting birth defects
- Improving crop yields and disease resistance
- Forensics
- Transplantation tissue typing
- Human genome sequencing
- Transgenic organism development and quality control
- CRISPR Cas9-based gene editing and quality control
- Resolution of haplotypes in polyploid organisms
- Resolution of phylogeny in complex or repetitive genomic regions

Fig. 2

MANY METHODS EXIST FOR ISOLATING NUCLEIC ACID MATERIAL

- Many different sources for nucleic acid material exist, which impose vastly different requirements for the isolation of DNA or RNA isolated for example from animals, humans, plants, microorganisms, bacteria, archaea, fungi

- As a consequence some of the DNA isolation methods, there are different qualities and properties of isolated DNA that affect downstream procedure such as the nucleotide sequencing

- For many applications, it is important to protect the integrity of the original nucleic acid / DNA material as much as possible, including its chemical modifications such as methylation, so as to be able to identify the original nucleotide sequence information including the contiguous chromosomal sequence

SEQUENCE LISTING

<160> NUMBER OF SEQ ID NOS: 4

<210> SEQ ID NO 1
<211> LENGTH: 21
<212> TYPE: DNA
<213> ORGANISM: ARTIFICIAL SEQUENCE
<220> FEATURE:
<223> OTHER INFORMATION: SHORT SECTION OF SINGLE STRANDED DNA

<400> SEQUENCE: 1
ccagttgatt accacctacg t                                    21

<210> SEQ ID NO 2
<211> LENGTH: 21
<212> TYPE: RNA
<213> ORGANISM: ARTIFICIAL SEQUENCE

```
<220> FEATURE:
<223> OTHER INFORMATION: SHORT SECTION OF SINGLE STRANDED RNA

<400> SEQUENCE: 2
ccaguugauu accaccuacg u                                              21

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: SHORT SECTION OF SINGLE STRANDED NUCLEOTIDES

<400> SEQUENCE: 3
ccagutgatt accaccuacg u                                              21

<210> SEQ ID NO 4
<211> LENGTH: 13
<212> TYPE: DNA
<213> ORGANISM: ARTIFICIAL SEQUENCE
<220> FEATURE:
<223> OTHER INFORMATION: INTEGRATION HOST FACTOR TARGET SEQUENCE
<220> FEATURE:
<223> OTHER INFORMATION: ALL N TO BE ANY NUCLEOTIDE

<400> SEQUENCE: 4
watcaannnn ttr                                                       13
```

METHOD FOR CAPTURING LONG POLYNUCLEOTIDES FOR SEQUENCING SPECIFIC GNOMIC REGIONS

CROSS REFERENCE TO RELATED APPLICATION

This Non-Provisional Patent application claims the benefit of priority of U.S. Provisional Patent Application No. 62/763,015, filed May 30, 2018, which is incorporated herein by reference in its entirety.

GOVERNMENT INTEREST

This invention was made with Government support under grant 1R43HG009580-01 awarded by the National Institutes of Health (NIH). The Government has certain rights in the invention.

STATEMENT REGARDING SEQUENCE LISTING

The Sequence Listing associated with this application is hereby incorporated by reference into the specification. The text file is 2 KB, was created on Nov. 15, 2019, and was submitted to the non-provisional patent application file on compact disk in computer-readable-format. The name of the text file containing the Sequence Listing is "RSEQ sequence listing clean for Non-Prov application Ser. No. 16/501,730 Dapprich 191115.txt".

FIELD OF THE INVENTION

In general the field of the invention relates to methods of long DNA or/and long RNA extraction methods for use in DNA and RNA sequencing, also to methods of extracting long DNA or/and long RNA and sequencing the extracted long DNA and/or extracted long RNA.

BACKGROUND OF THE INVENTION

There are several basic prior art methods used in DNA extraction from a biological cell. The cell membrane of the cell containing the DNA is broken to expose the DNA along with the cytoplasm within (cell lysis). Lipids from the cell membrane and the nucleus are broken down with detergents and surfactants. Breaking proteins by adding a protease is an optional step. Breaking RNA by adding an RNase is an optional step. The solution containing the DNA is treated with concentrated salt solution to make debris such as broken proteins, lipids and RNA to clump together. Centrifugation of the solution containing the DNA separates the clumped cellular debris from the DNA. DNA needs to be then purified to remove the detergents, proteins, salts and reagents used during cell lysis step. Common procedures for DNA purification include using an ethanol precipitation using ice-cold ethanol or isopropanol. DNA is insoluble in these alcohols, and will aggregate together so that a DNA pellet may be obtained by centrifugation of the alcohol-DNA mixture. Precipitation of the DNA may be improved by increasing of ionic strength, usually by adding sodium acetate. Alternatively, a mixture of phenol and chloroform can be used as an extraction liquid in which the phenol is used to denature proteins in the lysed cell sample. After centrifugation of the sample, the denatured proteins remain in the organic phase while the aqueous phase contains the DNA mixed with chloroform and phenol residues from solution. Mini-column purification can be used which binds the DNA nucleic acids binds to a solid phase such as a silica depending on the pH and the salt concentration of the buffer. Cellular and histone proteins bound to the DNA can be removed either by adding a protease or by having precipitated the proteins with sodium or ammonium acetate, or extracted them with a phenol-chloroform mixture prior to the DNA-precipitation. After isolation, the DNA is dissolved in slightly alkaline buffer, usually in the TE buffer, or in ultra-pure water.

Until the early 1990s, histones were dismissed by most as inert packing material for eukaryotic nuclear DNA. However, it is now important to consider that the removal of the histone proteins can have significant effects on DNA stability and in the regulation of gene expression. Epigenetics is the study of heritable changes in gene function that do not involve changes in the DNA sequence and examples of mechanisms that produce epigenetic changes are DNA methylation and histone modification—each alters how genes are expressed without altering the underlying DNA sequence. Gene expression can be controlled through the action of repressor proteins that attach to silencer regions of the DNA. These epigenetic changes may last through cell divisions for the duration of the cell's life, and may also last for multiple generations even though they do not involve changes in the underlying DNA sequence of the organism. Most epigenetic changes only occur within the course of one individual organism's lifetime; however, these epigenetic changes can be transmitted to the organism's offspring through a process called transgenerational epigenetic inheritance. Moreover, if gene inactivation occurs in a sperm or egg cell that results in fertilization, this epigenetic modification may also be transferred to the next generation.

Specific epigenetic processes include paramutation, bookmarking, imprinting, gene silencing, X chromosome inactivation, position effect, DNA methylation reprogramming, transvection, maternal effects, the progress of carcinogenesis, many effects of teratogens, regulation of histone modifications and heterochromatin, and technical limitations affecting parthenogenesis and cloning. DNA damage can also cause epigenetic changes. DNA damage is very frequent, occurring on average about 60,000 times a day per cell of the human body. These damages are largely repaired, but at the site of a DNA repair, epigenetic changes can remain. In particular, a double strand break in DNA can initiate un-programmed epigenetic gene silencing both by causing DNA methylation as well as by promoting silencing types of histone modifications (chromatin remodeling—see next section). In addition, the enzyme Parp1 (poly(ADP)-ribose polymerase) and its product poly(ADP)-ribose (PAR) accumulate at sites of DNA damage as part of a repair process. This accumulation, in turn, directs recruitment and activation of the chromatin remodeling protein ALC1 that can cause nucleosome remodeling. Nucleosome remodeling has been found to cause, for instance, epigenetic silencing of DNA repair gene MLH1. DNA damaging chemicals, such as benzene, hydroquinone, styrene, carbon tetrachloride and trichloroethylene, cause considerable hypomethylation of DNA, some through the activation of oxidative stress pathways.

Prior art epigenetic research relies upon methods including chromatin immuno-precipitation with large-scale variants ChIP-on-chip and ChIP-Seq, fluorescent in situ hybridization, methylation-sensitive restriction enzymes, DNA adenine methyltransferase identification (DamID) and bisulfite sequencing. Covalent modifications of either DNA (e.g. cytosine methylation and hydroxymethylation) or of histone proteins (e.g. lysine acetylation, lysine and arginine methylation, serine and threonine phosphorylation, and lysine ubiquitination and sumoylation) play central roles in many types of epigenetic inheritance. Therefore, the word "epigenetics" is sometimes used as a synonym for these processes. However, chromatin remodeling is not always inherited, and not all epigenetic inheritance involves chromatin remodeling.

The addition of methyl groups to DNA, mostly at CpG sites, to convert cytosine to 5-methylcytosine has the result that while the 5-methylcytosine performs much like a regular cytosine, pairing with a guanine in double-stranded DNA, some areas of the genome are methylated more heavily than others, and highly methylated areas tend to be less transcriptionally active, through a mechanism not fully understood. Methylation of cytosine can also persist from the germ line of one of the parents into the zygote, marking the chromosome as being inherited from one parent or the other (genetic imprinting). DNA methylation frequently occurs in repeated sequences, and helps to suppress the expression and mobility of 'transposable elements': Because 5-methylcytosine can be spontaneously deaminated (replacing nitrogen by oxygen) to thymidine, CpG sites are frequently mutated and become rare in the genome, except at CpG islands where they remain un-methylated. Epigenetic changes of this type thus have the potential to direct increased frequencies of permanent genetic mutation. DNA methylation patterns are known to be established and modified in response to environmental factors by a complex interplay of at least three independent DNA methyl-transferases, DNMT1, DNMT3A, and DNMT3B, the loss of any of which is lethal in mice. DNMT1 is the most abundant methyltransferase in somatic cells, localizes to replication foci, and has a 10-40-fold preference for hemi-methylated DNA and interacts with the proliferating cell nuclear antigen (PCNA). By preferentially modifying hemi-methylated DNA, DNMT1 transfers patterns of methylation to a newly synthesized strand after DNA replication, and therefore is often referred to as the 'maintenance' methyltransferase. DNMT1 is essential for proper embryonic development, imprinting and X-inactivation. To emphasize the difference of this molecular mechanism of inheritance from the canonical Watson-Crick base-pairing mechanism of transmission of genetic information, the term 'Epigenetic templating' was introduced. Furthermore, in addition to the maintenance and transmission of methylated DNA states, the same principle could work in the maintenance and transmission of histone modifications and even cytoplasmic, structural heritable states. In addition, eukaryotic genomes have numerous nucleosomes. Nucleosome position is not random, and determine the accessibility of DNA to regulatory proteins. This determines differences in gene expression and cell differentiation. It has been shown that at least some nucleosomes are retained in sperm cells where many histones are replaced by protamines. The nucleosome positioning is to a degree inherited. There appears to be a relation between nucleosome positioning and DNA methylation and hydroxymethylation (Epigenetics, Wikipedia, 2018). Thus, there is a need not met by the prior art for carefully and accurately sequencing DNA so as to be able to identify specific DNA bases in a DNA strand that have been methylated.

Other epigenetic changes are mediated by the production of different splice forms of RNA, or by formation of double-stranded RNA (RNAi). Descendants of the cell in which the gene was turned on will inherit this activity, even if the original stimulus for gene-activation is no longer present. These genes are often turned on or off by signal transduction, although in some systems where syncytia or gap junctions are important, RNA may spread directly to other cells or nuclei by diffusion. A large amount of RNA and protein is contributed to the zygote by the mother during oogenesis or via nurse cells, resulting in maternal effect phenotypes. A smaller quantity of sperm RNA is transmitted from the father, but there is recent evidence that this epigenetic information can lead to visible changes in several generations of offspring (Epigenetics, Wikipedia, 2018). It has been found that methylation of mRNA impacts human energy homeostasis. The obesity-associated FTO gene demethylate N6-methyladenosine in RNA. Thus, there is a need not met by the prior art for carefully and accurately sequencing RNA so as to be able to identify specific chemically modified RNA bases in an RNA strand that have been methylated.

MicroRNAs (miRNAs) are members of non-coding RNAs that range in size from 17 to 25 nucleotides. miRNAs regulate a large variety of biological functions in plants and animals. As of 2013, approximately 2000 miRNAs have been discovered in humans and these can be found online in a miRNA database. Each miRNA expressed in a cell may target about 100 to 200 messenger RNAs that it downregulates. Most of the downregulation of mRNAs occurs by causing the decay of the targeted mRNA, while some downregulation occurs at the level of translation into protein. It appears that about 60% of human protein coding genes are regulated by miRNAs. Many miRNAs are epigenetically regulated. About 50% of miRNA genes are associated with CpG islands, that may be repressed by epigenetic methylation. Transcription from methylated CpG islands is strongly and heritably repressed. Other miRNAs are epigenetically regulated by either histone modifications or by combined DNA methylation and histone modification. Thus, there is a need not met by the prior art for carefully and accurately sequencing miRNA so as to identify specific chemically modified miRNA bases when sequencing an miRNA strand.

Bacterial DNA binding proteins are a family of small, usually basic proteins of about 90 amino acids in length and are called histone-like proteins. Since bacterial binding proteins have a diversity of functions, it has been difficult to define a common function for them. Thus they are referred to as histone-like protein that have many traits in common with eukaryotic cell histone proteins. Eukaryotic histones are known to package DNA to help the DNA to fit within the cell's nucleus, and the eukaryotic histone proteins are highly conserved structurally. An example of a bacterial histone-like protein is the HU protein found in *Escherichia coli*. HU is a dimer of closely related alpha and beta chains that in other bacteria can be a dimer of identical chains. HU-type proteins have been found in a variety of eubacteria, cyanobacteria and archaebacterial. HU proteins are also encoded in the chloroplast genome of some algae. The integration host factor (IHF) histone is a dimer of closely related chains which may be important in genetic recombination, genetic translational and genetic transcriptional control processes found in Enterobacteria and in viral proteins including the African swine fever virus protein A104R (or LMW5-AR). (see Bacterial DNA binding protein, Wikipedia, 2018). Histone-like proteins are also present in many Eubacteria, Cyanobacteria, and Archaebacteria where the histone-like proteins participate in DNA-dependent functions including an architectural role for maintaining the structural integrity of processes such as transcription, recombination, replication, and other DNA-dependent processes. Because the amino acid composition of HU resembled the eukaryotic histones, this prompted investigations into bacterial histone-like proteins.

It was found that the bacterial DNA binding protein during DNA replication stabilize the lagging DNA and interact with DNA polymerase III. There is a single-stranded DNA binding (SSB) protein that engages the x subunit of DNA polymerase III in environments of varying salt concentrations. At the DNA lagging strand site, DNA polymerase III removes nucleotides individually from the DNA binding protein. Thus in E. coli, SSB interactions with the x subunit of DNA polymerase III help to maintain the correct conformation of the DNA polymerase III so that the binding affinity of enzymes to ssDNA is increased. Furthermore, binding of SSB to DNA polymerase III at the replication fork prevents dissociation of SSB, and consequently increases the efficiency of DNA polymerase III to synthesize a new DNA strand.

In addition to stabilizing the bacterial DNA, the bacteria DNA binding protein H-NS (known as histone-like nucleoid-structuring protein) regulates gene expression. H-NS regulates DNA gene expression by repressing and by activating certain genes. H-NS binds to DNA with an intrinsic curvature. In E. coli, H-NS binds to a P1 promoter decreasing rRNA production during stationary and slow growth periods. RNA polymerase and H-NS DNA binding protein have overlapping binding sites. Thus it is imagined that H-NS regulates rRNA production by acting on the transcription initiation site. It has been found that H-NS and RNA polymerase both bind to the P1 promoter and form a complex. When H-NS is bound with RNA Polymerase to the promoter region, there are structural differences in the DNA that are accessible. It has also been found that H-NS can affect translation as well by binding to mRNA and causing its degradation. The RNA polymerase at the promoter is surrounded by curved DNA which wraps around the polymerase and the H-NS binds to the curved DNA so as to lock the RNA polymerase at the promoter and prevent transcription. Then needed are environmental signals and transcription factors to release the DNA bacterial binding protein's locking of the RNA polymerase so that transcription may proceed.

HU is another bacterial histone-like protein and it resembles the eukaryotic Histone H2B. HU with the assistance of a topoisomerase induces negative supercoiling into circular DNA. The HU protein has been assigned roles in DNA replication, recombination, and repair. HU protein have an α-helical hydrophobic core and two positively charged β-ribbon arms, The HU histone-like protein can bind with low affinity and non-specifically to dsDNA but can bind with high affinity to DNA regions altered to have nicks, junctions, gaps, forks, and overhangs. The β-ribbon arms bind to the minor groove of DNA in low affinity states; and then in high affinity states, part of the HU protein α-helical core interacts with the DNA as well. HU protein also binds to RNA and to DNA-RNA hybrids with the same affinity as supercoiled DNA. For example, HU can bind with high specificity to the mRNA of rpoS, a transcript for the stress sigma factor of RNA polymerase, and can stimulate translation of the protein. Additional to this RNA function, it was also demonstrated that HU binds DsrA, a small non-coding RNA that regulates transcription by repressing it. H-NS also can stimulate translation by increasing expression of rpoS. This suggests HU has multiple influences on transcription and translation in bacterial cells.

Another histone-like protein is Integration host factor (IHF). This is a nucleoid-associated protein found in gram negative bacteria. IHF is a heterodimer with α and β subunits that bind to 5'-WATCAANNNNTTR-3' (SEQ ID NO 4) DNA, bending it by approximately 160 degrees. The 13 arms of IHF have proline groups that stabilize the DNA kinks which help to compact DNA and permit DNA supercoiling. In experiments, the mode of binding to DNA depends on ion concentration in the medium. In high concentration KCl, solutions there is weak DNA bending. A sharper DNA bending occurs when the KCl concentration is less than 100 mM and if the IHF is not concentrated. IHF is found to be a co-factor for recombination of X, phage in to E. coli and recently appreciated as having a key role in CRISPR type I and type II systems. For example, IHF has a role in allowing the Cas1-Cas2 complex to integrate new spacers into the CRISPR sequence. The bending of the DNA by IHF is thought to alter spacing in the DNA major and minor grooves, so as to allow the Cas1-Cas2 complex to make contact with the DNA bases. This is a key function in the CRISPR system as new spacers area are added at beginning of the CRISPR sequence next to the leader sequence. This directing of integration of the new spacers by IHF ensures that spacers are added chronologically, and this allows for greater protection against recent viral infection. The functions of bacterial DNA-binding proteins are not limited to DNA replication. There are other pathways that these histone-like proteins impact. The H-NS is been known to have roles in chromosome organization and gene regulation. In addition H-NS indirectly regulates flagella functions by regulating messenger molecule Cyclic di-GMP, the biofilm regulatory protein CsgD, and the sigma factors, σ(S) and σ(F).

TABLE 1

Comparison of some DNA Binding Proteins

| DNA Binding Protein | Size | Structure | Binding Site | Effect |
|---|---|---|---|---|
| H-NS | 15.6 kDa | Exists in dimers to physically prevent RNA polymerase from binding to promoter | Binds to bent DNA, binds to P1 promoter in E. coli | Regulation of gene expression |
| HU | 10 kDa | Has a α-helical core and two positively charged β-ribbon arms | Binds non-specifically to dsDNA, binds to DsrA, a small non-coding RNA that regulates transcription | Induces negative supercoiling into circular DNA |
| IHF | 20 kDa | Is a αβαβ heterodimer | Binds to specific sequences of DNA | Creates kinks in DNA |

Further studies are aiming to characterize the ways this nucleoid-organizing protein affects the motility of the cell through other regulatory pathways. Bacterial DNA-binding proteins is used to study Salmonella enterica serovar Typhimurium, in which the T6SS genes are activated from a macrophage infection. When S. Typhimurium infects, their efficiency can be improved through a sense-and-kill mechanism with T6SS H-NS silencing. Assays are created that combine reporter fusions, electrophoretic mobility shift assays, DNase footprinting, and fluorescence microscopy to silence the T6SS gene cluster by the histone-like nucleoid structuring H-NS protein.

Histones are highly alkaline proteins found in eukaryotic cell nuclei that package and order the DNA into structural units called nucleosomes. Five major families of histones exist: H1/H5, H2A, H2B, H3, and H4. Histones H2A, H2B, H3 and H4 are known as the core histones, while histones H1/H5 are known as the linker histones. As the chief protein components of chromatin, histones function as spools around which DNA winds, and histones have a role in gene regulation. Without histones, the unwound DNA in chromosomes would be very long, for example, each human diploid cell has 1.8 meters of DNA to be wound on the 90 micrometers of chromatin so that when the diploid cells duplicate during mitosis, there is about 120 micrometers of chromosomes. Another way to describe this spooling is that the compacted DNA molecule due to its histone windings is 40,000 times shorter than an unpacked DNA molecule. Eukaryotic histones were first discovered through experiments in 0.4M NaCl. In these high salt concentrations, the eukaryotic histone protein is eluted from a DNA solution in which single stranded DNA is bound covalently to cellulose. Following elution, the protein readily binds DNA, indicating the protein's high affinity for DNA.

The histones undergo posttranslational modifications that alter their interaction with DNA and nuclear proteins. The H3 and H4 histones have long tails protruding from the nucleosome, which can be covalently modified at several places. Modifications of the tail include methylation, acetylation, phosphorylation, ubiquitination, SUMOylation, citrullination, and ADP-ribosylation. The core of the histones H2A and H2B can also be modified. A very large catalogue of histone modifications have been described, but a functional understanding of most is still lacking. Collectively, it is thought that histone modifications may underlie a histone code, whereby combinations of histone modifications have specific meanings. However, most functional data concerns individual prominent histone modifications that are biochemically amenable to detailed study Histone modifications act in diverse biological processes such as gene regulation, DNA repair, chromosome condensation (mitosis) and spermatogenesis (meiosis).

Posttranslational modifications that alter the interaction of histones with DNA include the following chemical modifications. Firstly, although the addition of one, two, or three methyl groups to lysine has little effect on the chemistry of the histone; methylation leaves the charge of the lysine intact and adds a minimal number of atoms so steric interactions are mostly unaffected, however, proteins containing Tudor, chromo or PHD domains, amongst others, can recognize lysine methylation with exquisite sensitivity and differentiate mono, di and tri-methyl lysine, to the extent that, for some lysine residues (e.g.: H4K20) mono, di and tri-methylation appear to have different meanings. Because of this, lysine methylation tends to be a very informative mark and dominates the known histone modification functions. Secondly, as with lysine methylation effects, the addition of methyl groups to arginine has similar effects, and some protein domains—e.g., Tudor domains—can be specific for methyl arginine instead of methyl lysine. Arginine is known to be mono- or di-methylated, and methylation can be symmetric or asymmetric, potentially with different meanings. Enzymes called peptidyl arginine deiminases (PADs) hydrolyze the imine group of arginine and attaches a keto group, so that there is one less positive charge on the amino acid residue. This process has been involved in the activation of gene expression by making the modified histones less tightly bound to DNA and thus making the chromatin more accessible. PADs can also produce the opposite effect by removing or inhibiting mono-methylation of arginine residues on histones and thus antagonizing the positive effect arginine methylation has on transcriptional activity.

Thirdly, the addition of an acetyl group has a major chemical effect on lysine as it neutralizes the positive charge. This reduces electrostatic attraction between the histone and the negatively charged DNA backbone, loosening the chromatin structure; highly acetylated histones form more accessible chromatin and tend to be associated with active transcription. Lysine acetylation appears to be less precise in meaning than methylation, in that histone acetyltransferases tend to act on more than one lysine; presumably this reflects the need to alter multiple lysine residues to have a significant effect on chromatin structure. The modification includes H3K27ac.

Fourthly, the addition of a negatively charged phosphate group to serine, threonine, and/or tyrosine is a phosphorylation that can lead to major changes in protein structure, and there is a well-appreciated role of phosphorylation in controlling protein function. It is not clear what structural implications histone phosphorylation has, although histone phosphorylation has functions as a post-translational modification in binding domains such as BRCT.

Many histone modifications are involved in control of transcription. Fifthly, two histone modifications are particularly associated with active transcription: trimethylation of H3 lysine 4 (H3K4me3); and the trimethylation of H3 lysine 36 (H3K36me3). Sixthly, three histone modifications are particularly associated with repressed genes: trimethylation of H3 lysine 27 (H3K27me3); the Di and tri-methylation of H3 lysine 9 (H3K9me2/3); and the trimethylation of H4 lysine 20 (H4K20me3).

Seventhly, marking sites of DNA damage are an important function for histone modifications: for example (1) phosphorylated H2AX (also known as gamma H2AX) is a marker for DNA double strand breaks and forms part of the response to DNA damage. H2AX is phosphorylated early after detection of DNA double strand break, and forms a domain extending many kilobases either side of the damage H3K56Acx is required for genome stability. H3K56 is acetylated by the p300/Rtt109 complex, but is rapidly deacetylated around sites of DNA damage. H3K56 acetylation is also required to stabilize stalled replication forks, preventing dangerous replication fork collapses. (Histone, Wikipedia, 2018).

Chromosome condensation is an important factor in DNA quality. Phosphorylation of H3 at serine 10 (phospho-H3S10)—the mitotic kinase aurora B phosphorylates histone H3 at serine 10, triggering a cascade of changes that mediate mitotic chromosome condensation. H3S10 phosphorylation has also been linked to DNA damage caused by R loop formation at highly transcribed sites. Phosphorylation H2B at serine 10/14 (phospho-H2BS10/14)— the phosphorylation of H2B at serine 14 in mammals is also linked to chromatin condensation, but for the purpose of mediating chromosome condensation during apoptosis.

It is a problem that the current knowledge about the human genome is limited due to many limitations in prior art methods of isolation of DNA and RNA and its capture for DNA and RNA sequencing. This imprecision causes bad data and prevents a needed level of confidence for accurate personalized medicine treatment of a patient. Treating a patient based upon the patient's single cells biopsy is the future. In the future the cells can be found in the patient's blood and the DNA or RNA sequencing is used to identify precisely what kind of metastatic cancer cell the cell represents. How is the ability of the doctor who needs to confidently determine if the biopsied cell is a normal cell or is an abnormal cell going to be possible if the cells being biopsied have a specific genetics that cannot be properly characterized in terms of their DNA or RNA sequences or their epigenetic modification. To accomplish proper genetics characterization will require accurate and higher resolution sequencing of long DNA and/or long RNA of the patient's cell. It is known that current sequencing technology suffers from false positive and/or false negative errors. It is also known that DNA and RNA extraction methods cause DNA and RNA significant damages as well as probably very significant DNA and RNA sequence modifications when the DNA and/or RNA is extracted from a biological and prepped for sequencing. Furthermore, there are many biochemical activities of histones that involve the DNA. Thus, it needs to be questioned as to how carefully histone proteins should be separated from the DNA that has been tightly spooled on them.

There are numerous problems with current DNA enrichment methods when DNA fragments of lengths greater than 1,000 bases, and especially of lengths greater than 10,000 bases. It is difficult to capture DNA fragments of lengths greater than 1,000 bases, and especially of lengths greater than 10,000 bases with high efficiency and high specificity. The problem may be due to genomic DNA and other nucleic acid material to becoming physically or topological entangled. This is a serious sequencing error uncertainty problem with unknown size implications. Simply stated it is a problem if irreversible and non-native connections between DNA strands arise during the DNA extraction processes are taking place for harvesting DNA from biological cells or commercial DNA samples. Then the DNA handling in a lab doing sequencing is fraught with error in accuracy and sensitivity and data reproducibility. So the DNA extraction processes needs to be careful to not accidentally connect DNA strands together and create artefactual DNA sequences during the extraction process with other DNA molecules. The lack of careful rigorous and error assessed long DNA sequencing procedure and poor capabilities in the prior art make it clear this is a major problem: long occurring and widespread. The solution to this problem is unmet by prior art DNA extraction methods currently applied to carefully prepare a DNA Sample source so that there can be DNA sequencing. Whereas DNA isolation, extraction, and capture methods may causes some unavoidable artifacts to an extent, if and when they occur, then the artifacts need to be discoverable, quantified as to severity and easily isolated/removed during the DNA extraction process. The DNA extraction process includes the DNA capture process or is the same. Thus, it is well known that DNA molecules frequently get fragmented during DNA extraction product calls. This fragmentation of the DNA is regardless of whether the protocols are intended to produce any genomic DNA material from a sample. The fragmentation occurs regardless of the DNA sequence and whether or not someone is attempting to perform targeted sequence capture of specific regions of interest.

Another problem is that typical DNA capture methods need to employee very long capture primers in order to produce a sufficient binding strength so as to be able to pull down large genomic DNA templates. The needed use of larger capture primers results in a significant loss of specificity and loss of method sensitivity with regard to sequencing the subtle sequence changes in the targeted sequence. It recognized in the prior art that is frequently impossible to distinguish between slight variations of sequences that might occur in a DNA target regions versus a non-targeted DNA region. Although it might help to be able to use relatively shorter DNA capture primers since they might be more specific and sensitive to small variations in a DNA sequence, however, prior art is unable to use known DNA capture methods with short DNA capture primers so as to efficiently pull down large genomic DNA molecules.

Another problem is that the methods that do produce large DNA segments with any reasonable capture efficiency are methods that tend to be highly complex, expensive, and difficult to operate and typically require the use of expensive equipment. Example capture methods in the prior art with problems include flow cytometry, laser capture microdissection, and pulsed field gel electrophoresis. These approaches are not reasonably scalable. These methods also have the problem that they cannot be part of integrated DNA sequencing methods that make use of automated sample preparation sequencing and DNA analysis processes.

Another problem is that prior art methods requiring short fragment capture are not able to isolate the target DNA regions containing unexpected DNA structural variations, insertions, unknown sequences, and/or rearrangements that are not anticipated and designed as one of the DNA capture primers. Therefore it is a serious error that crucial information about the natural DNA variability of a particular DNA sample can be never detected. Such false negative errors result in the missing of important DNA variations which are essential for producing a correct diagnosis or treatment recommendation for a patient whose DNA analysis might be critical for them, for example if the DNA needed to be extracted and sequenced comes from a patient's tumor biopsy. Thus, needed are more accurate and less expensive methods of region specific long DNA and RNA extraction methods for use in DNA and RNA sequencing.

BRIEF SUMMARY OF THE INVENTION

A method for capturing a polynucleotide comprising a DNA target segment from a population of polynucleotide molecules, the method comprising the steps of: providing a mixture comprising the population of the polynucleotide molecules, one or more polynucleo-tide primers, nucleotides, biotinylated nucleotides, a polymerase enzyme and a buffered liquid medium; denaturing the polynucleotide molecules in the mixture so as to create single stranded portions of the polynucleotide molecules which can be accessible to the polynucleotide primers hybridizing the polynucleotide primers to the polynucleotide comprising the DNA target segment; creating an extended polynucleotide primer by using the nucleotides, the biotinylated nucleotides and the polymerase enzyme as a means for labeling with biotin and increasing the extent of hybridization of the extended polynucleotide primer to the polynucleotide comprising the DNA target segment; adding streptavidin-labeled magnetic beads to the mixture; using a magnetic field to move the streptavidin-labeled magnetic beads relative to the buffered liquid medium as a means for increasing binding of the biotinylated nucleotides of the extended polynucleotide primer to the streptavidin-labeled magnetic beads; using either a rotation of the magnetic field relative to the mixture or a rotation of the mixture relative to the magnetic field for causing a streptavidin-labeled magnetic bead rotation in the buffered liquid medium as a means for performing the steps of increasing the binding of the biotinylated nucleotides of the extended polynucleotide primer to the streptavidin-labeled magnetic beads and increasing the winding of the biotinylated nucleotides of the extended polynucleotide primer onto the streptavidin-labeled magnetic beads, so as to increase the probability of capturing a long polynucleotide comprising a DNA target segment and so as to increase the probability of preventing damage to the long polynucleotide comprising a DNA target segment; and using the magnetic field to collect the streptavidin-labeled magnetic beads so as to capture the polynucleotide comprising the DNA target segment which is bound to the streptavidin-labeled magnetic beads.

Some embodiment of the present invention are methods which include one or more of the following. Some embodiments of invention have a preference wherein each magnetic bead has a plurality of organic molecule linkers wherein each linker is a streptavidin terminated linker, wherein each streptavidin terminated linker can bind to a biotinylated nucleotide base in a DNA sequence being formed during a DNA primer extension process, and wherein the biotinylated nucleotide base is added to the DNA sequence during primer extension process at a frequency which is about one biotinylated nucleotide per 10-30 nucleotide bases. In some embodiments the frequency is selected from the group consisting of one biotinylated nucleotide per 5 nucleotide bases of DNA primer extension, one biotinylated nucleotide per 6 nucleotide bases of DNA primer extension, one biotinylated nucleotide per 7 nucleotide bases of DNA primer extension, one biotinylated nucleotide per 8 nucleotide bases of DNA primer extension, one biotinylated nucleotide per 9 nucleotide bases of DNA primer extension, one biotinylated nucleotide per 10 nucleotide bases of DNA primer extension, one biotinylated nucleotide per 15 nucleotide bases of DNA primer extension, one biotinylated nucleotide per 20 nucleotide bases of DNA primer extension, one biotinylated nucleotide per 30 nucleotide bases of DNA primer extension, one biotinylated nucleotide per 40 nucleotide bases of DNA primer extension, one biotinylated nucleotide per 50 nucleotide bases of DNA primer extension, one biotinylated nucleotide per 60 nucleotide bases of DNA primer extension, one biotinylated nucleotide per 70 nucleotide bases of DNA primer extension, one biotinylated nucleotide per 80 nucleotide bases of DNA primer extension, one biotinylated nucleotide per 90 nucleotide bases of DNA primer extension, one biotinylated nucleotide per 100 nucleotide bases of DNA primer extension, and any combination thereof.

Some embodiments of invention use a homogenous magnetic field for moving the magnetic beads which have a linker such as streptavidin so that the magnetic beads can move to contact a DNA strand by a gentle bumping process which does not cause a formation of aggregated DNA fibers.

Some embodiments of invention use the homogeneous magnetic field for aligning magnetic beads and then for rotating the magnetic beads which have a linker such as streptavidin or another suitable linking means for forming a linkage to biotinylated nucleotides as they are added to the DNA during DNA primer extension.

Some embodiments of the present invention use each rotating magnetic bead to wind the DNA arising from a DNA primer extension for protecting the DNA produced by the primer extension process from shearing forces that may occur in the liquid medium containing the DNA primer extension.

Some embodiments of invention have a preference wherein the DNA primer extension process uses short capture primers that have a number of nucleotide bases selected from the group consisting of 5 bases, 6 bases, 7 bases, 8 bases, 9 bases, 10 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31q bases, 32 bases, 33 bases, 34 bases, 35 bases, 36 base, 37 bases, 38 bases, 39 base, 40 bases, 41 base, 42 bases, 43 bases, 44 bases, 45 bases, 46 bases, 47 bases, 48 bases, 49, bases, 50 bases and any combination thereof. Particularly preferred is using short capture primers of between about 12 to about 28 bases in length. More particularly preferred is using short capture primers that are between about 15 to about 25 bases in length.

Surprisingly, the method embodiments of the present invention can use short capture primers that are about 5-15 fold shorter in nucleotide base length than the nucleotide base length of prior art capture primers. More surprisingly, preferred embodiments of the present invention are methods which can pull down DNA much larger size than is possible by using prior art capture primers.

Some embodiments of the present invention involve methods of region-specific extraction and region-specific amplification either independently of or in combination with 3'-protected primers and primers that are longer than the regular random hexamers used in conventional WGA kits, and with a polymerase that is (A) strand displacing such as Φ29 DNA polymerase and/or (B) able to sustain potentially considerably higher temperatures such as BST 2.0 polymerase which is more thermostable than the Φ29 DNA polymerase.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

FIG. 1 in accordance with one embodiment of the present invention lists 8 uses for long-read sequence capture of a DNA and/or an RNA sample. These example applications are made more accurate and comprehensive when DNA enrichment is conducted with long read sequences, as opposed to short fragment enrichment, amplification and sequencing. A lot of complex regions in the genome cannot be accurately assembled with unenriched short read data and with short fragment enrichment methods.

FIG. 2 in accordance with one embodiment of the present invention shows many different methods exist for isolating nucleic acid material. The quality of the DNA material that can be obtained from a sample depends greatly on the initial storage and handling conditions both of the original sample, such as a blood or tissue buccal swab or cell line sample, as well as on the type of DNA or RNA extraction method that is used to prepare the material. For the purpose of long DNA fragment enrichment it is critical that both the initial 17 sample is stored and handled correctly and the DNA extraction process is selected and carried out in a way that maximally retains long molecular DNA segments. It is important as well that the isolated DNA is not allowed to become entangled during enrichment or at any step thereafter in order to avoid an increase in off-target capture during extraction.

FIG. 11 depicts the relative magnetic motion of the magnetic bead 1105 that is achieved by an inhomogeneous gradient of magnetic field lines 1108 generated by the magnet 1110. The motion of the magnetic particle 1105 is directed towards the magnet surface 1111 as indicated by the thick black arrow 1109. The gradient magnetic field lines 1108 are indicated by dashed lines converging towards the surface 1111 of the magnet 1110. By generating such relative motion of the magnetic bead through the solution, the probability that a biotin tag 1102 will encounter a streptavidin moiety 1106 on the bead surface is increased. As a result, the overall capture efficiency for genomic template molecules that contain extended RSE primers with biotin tags is greatly enhanced compare two situations where no relative motion of the magnetic bead through solution is generated. The relative motion is called active magnetic mixing when it is done through an inhomogeneous magnetic field, or through a rotating homogeneous magnetic field that will create no translation of low movement of the magnetic particles but results in the formation of magnetic chains and fibers that will rotate following the rotating magnetic homogeneous field like propellers but without any translational movement toward the magnet. Alternatively the relative magnetic motion of the beads through the solution can also be achieved by non-magnetic means, for instance by centrifugation.

FIG. 16 at bottom, labeled 2, in accordance with one embodiment of the present invention depicts the use of separate origami oligo nucleotides that are used independently from the RSE capture primers. In this case the genomic template 1607 has specific target regions indicated by 1605 and 1606 that are used to design complimentary hybrid oligonucleotides that contain the respective complementary sequences 1608 and 1609. There are typically many of specific target sequences that ultimately located thousands of tens of thousands of bases apart from each other that I used to design the complementary origami oligonucleotides, and all of those are then used to pull together the targeted genomic template 1610 into a much more compact and looped structure through condensation with origami oligonucleotides 1611, resulting in a robust and compact structure depicted in 1612. For further details for enabling these embodiments of the invention see Rothemund 2016. For supplemental enablement details see methods published at dna.caltech.edu/DNApublications-Rothemund.html.

DETAILED DESCRIPTION OF THE INVENTION

Figure 3:
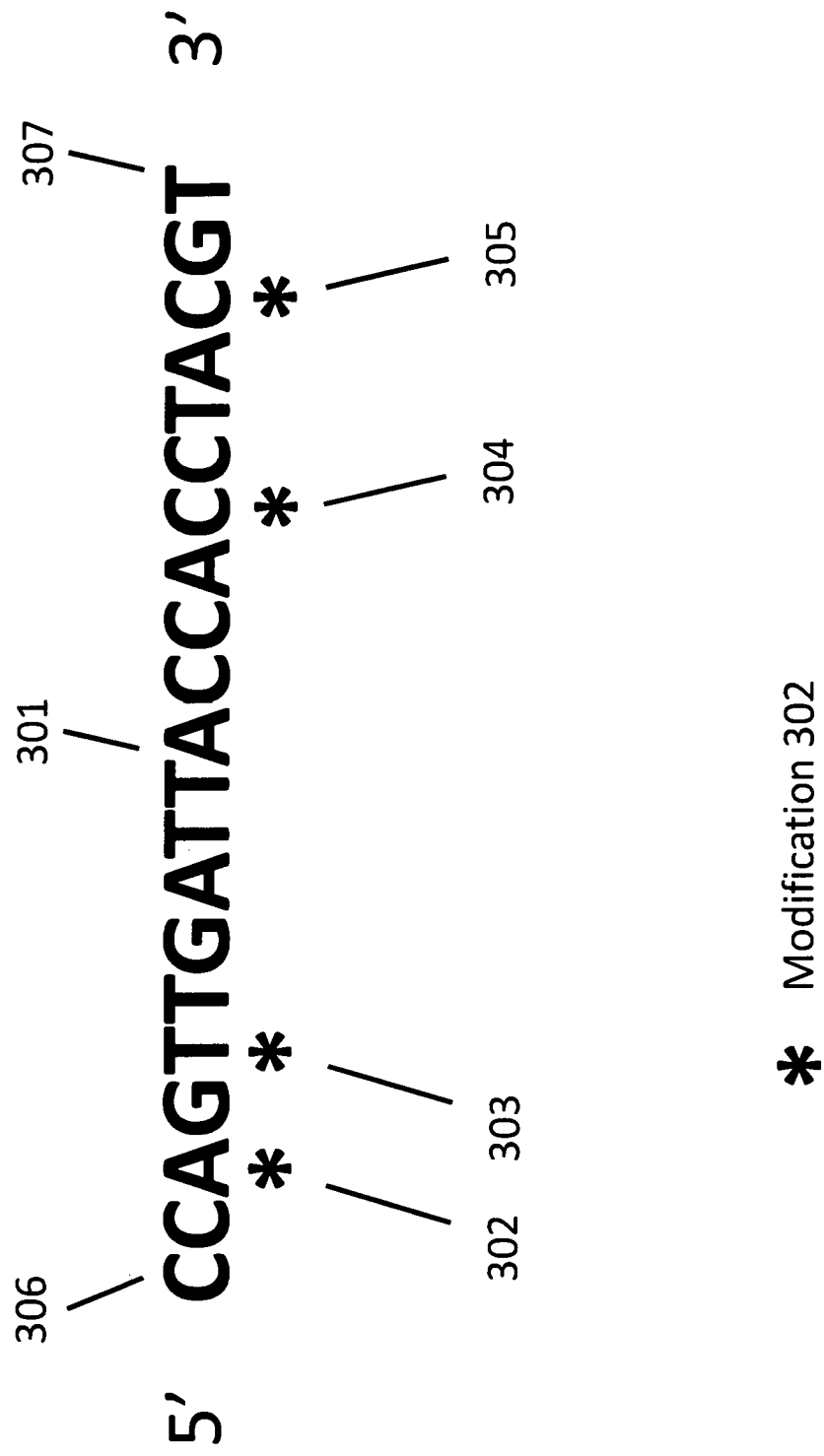
FIG. 3 in accordance with one embodiment of the present invention depicts in a highly schematic form, a short section of a single stranded DNA 301 CCAGTTGATTACCACC-TACGT (SEQ ID NO 1) with a 5' end nucleotide cytosine base 306, a modified adenine nucleotide base 302, a modified thymidine nucleotide base 303, a modified cytosine nucleotide base 304, and a modified cytosine nucleotide base 305. The 3' end of the single stranded DNA 301 is a thymidine nucleotide 307

The present invention comprises methods for making region-specific long DNA and/or long RNA extractions for use in DNA and/or RNA sequencing of the region-specific long DNA and/or long RNA extracts. Some embodiments of the present invention comprise a method of extracting and preparing DNA and or RNA for DNA and or RNA sequencing, the method comprising the steps of: (1) incorporating multiple biotins during DNA primer extension so as to stabilize the DNA extension; (2) using of active magnetic mixing (as opposed to an electrophoretic method) for avoiding DNA shearing; (3) using a plurality of chemically modified biotins and other modified bases, various linkers, various spacers, on a multiple DNA nucleotides as a means for binding a multiple number the bases of the DNA extension to just one magnetic bead so as to causes cooperative localization effects upon the DNA extension; (4) causing the magnetic bead to which the DNA is bound at multiple sites to the one bead to undergo a rotation; (5) rotating magnetic field around the magnetic bead so as to cause a bead rotation for winding the DNA attached to the bead via (biotin linkers, other modified bases, other linkers, other spacers); and (6) winding up of the DNA around the bead as a means for protecting the DNA to be prepared for DNA sequencing from shearing forces that could cause DNA breaking. A free DNA strand in a liquid suspension is susceptible to breaking when the DNA in the liquid undergoes tension or twisting due to a flowing, whirl-pooling, or other turbulent flowing of the liquid by any means. Some embodiments of the present invention involve methods of region-specific extraction and region-specific amplification either independently of or in combination with 3'-protected primers and primers that are longer than the regular random hexamers used in conventional WGA kits, and with a polymerase that is (A) strand displacing (like Φ29 DNA polymerase) and (B) also able to sustain potentially considerably higher temperatures.

Region-specific extraction and region-specific amplification has three utilities. By using the higher specificity of longer DNA primers (e.g. 15 nucleotide bases or longer) the DNA primers can be used to selectively hybridize to specific genomic regions of interest at an elevated temperatures such as 40° C. to 60° C. at which temperature hybridization of shorter primers cannot be achieved. The temperature range during the hybridization to specific genomic regions of interest is a temperature range selected from the group consisting of 20° C. to about 90° C., 25° C. to 80° C., 30°

C. to 70° C., 35° C. to 65° C., 40° C. to 60° C., 45° C. to 65° C., 45° C. to 60° C., 50° C. to 60° C., 55° C. to 65° C., 55° C. to 60° C., and any combination thereof.

Some embodiments of invention have a preference wherein the DNA primer extension process uses short capture primers that have a length (in terms of the number of nucleotide bases in the primer) which is selected from the group consisting of 5 bases, 6 bases, 7 bases, 8 bases, 9 bases, 10 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31q bases, 32 bases, 33 bases, 34 bases, 35 bases, 36 base, 37 bases, 38 bases, 39 base, 40 bases, 41 base, 42 bases, 43 bases, 44 bases, 45 bases, 46 bases, 47 bases, 48 bases, 49, bases, 50 bases and any combination thereof. For some embodiments of the present invention the short capture primers are preferably between about 12 to about 28 bases in length or between about 15 to about 25 bases in length.

Surprisingly, the method embodiments of the present invention can use short capture primers that are about 5-15 fold shorter in nucleotide base length than the nucleotide base length of prior art capture primers. More surprisingly, preferred embodiments of the present invention are methods which can pull down DNA much larger size than is possible by using prior art capture primers. By shorter primers, the inventors mean for example, the use of random hexamer primers used at lower temperatures (such RT or about 37° C.), as used in typical whole genome amplification (WGA) reaction protocols. The purpose of WGA is for the random hexamer primers to bind literally everywhere so that ideally every type and sequence of DNA is amplified. By using longer primers that are designed to be specific to a target region and hybridizing them at higher temperature, the binding of shorter primers (including any portions of longer primers, such as their 3'-ends that might match to another sequence but which is not targeted) is inhibited, as a means for selectively amplifying genomic DNA target segments and regions. Importantly and surprisingly, the nature of the multiple strand displacement (MDA) process makes it possible for amplifying unknown sequence sections that are contained within the sections that can be directly targeted by the targeting primers. This process, which may be termed a region-specific amplification (RSA), is surprisingly both specifically enriching an extended target region and maintaining and providing DNA template material for sequencing of any unexpected variation that may occur throughout the targeted region. Furthermore, the present invention advantageously provides redundancy and robustness through the process of using multiple RSA primers and an enzyme with a long processivity (50 kb or more reported) is useful for reliably detecting large scale and unexpected changes in the template sequence. Processivity means the ability of an enzyme to stay attached and work on a DNA template for extended distances without dissociating from the DNA template.

Large scale and unexpected changes in the DNA template sequence may include structural variations (SV's), chromosomal rearrangements, insertions, and deletions that commonly occur for instance in cancer cells and circulating tumor cells. Structural variation (also known as genomic structural variation) is the variation in the organizational structure of an organism's chromosome and consists of many kinds of variation in the genome of one species, and usually includes microscopic and submicroscopic types, such as deletions, duplications, copy-number variants, insertions, inversions and translocations. Typically a structure variation affects a DNA sequence length about 1 kb to 3 Mb, which is larger than SNPs and smaller than a chromosome abnormality. The definition of structural variation says nothing about frequency or phenotypical effects. Many structural variants are associated with genetic diseases. SVs are more difficult to detect than SNPs. Approximately 13% of the human genome are defined as structurally variant in the normal population, and there are at least 240 genes that exist as homozygous deletion polymorphisms in human populations, suggesting these genes are dispensable in humans. Structural variations may comprise millions of nucleotides of heterogeneity within every genome, and are thought to have an important role in human diversity and disease susceptibility (see Structural Variation, Wikipedia, 2018).

The application of this RSA strategy and the following two variations is therefore of value to applications in immuno-oncology and other forms of cancer that are severely hampered by the ability to robustly and reliably very difficult and potentially rapidly changing regions of the genome. These may be driven by the tendency of the tumor to try and evolve and outrun the immune system to deviate considerably from the 'normal' expected reference genomes that are available, which in turn makes it very difficult and sometimes impossible to find suitable reference sequences for amplification or capture probes or primers to reliably and comprehensively represent any changes that an evolved tumor genome (either of a single cell or of a group of cells in the body) may have acquired. Clearly this is an advantage over PCR and other amplification methods that rely on specific primers that must bind in order to obtain a product. With PCR, if there are unexpected mutations or other forms of variation that prevent the primers from binding properly, there will be no amplification product of the unexpected mutations or other forms of genetic variation.

For the present invention, methods which use RSA with selected primers and strand displacing amplification avoid problems of a PCR process which depends upon using specific primers. RSA primers can be synthesized either conventionally in columns (IDTDNA) or via light-directed synthesis microarray and can be protected near the 3'-end for instance by thiophosphate groups or other means to avoid the degradation of the RSA primers by exonucleolytic activity of the polymerase used. A modified polymerase without an exonucleolytic function can be used without the need for a protection of primers against 3'-end digestion.

For embodiments of the present invention, the RSE (Region-specific extraction) can be performed by using a strand-displacing enzyme such as Φ29 DNA polymerase or BST and incorporating biotinylated nucleotides. The Φ29 DNA polymerase is an enzyme from the bacteriophage Φ29 and is used for multiple displacement DNA amplification procedures because this polymerase has no intrinsic helicase activity, but can carry out an equivalent function by way of its strong binding to single stranded DNA, particularly in preference to double stranded nucleic acid. This is the property of this enzyme that makes is favorably applicable to Multiple Displacement Amplification. This enzyme facilitates the "debranching" of double stranded DNA. The enzyme has many desirable properties for whole genome amplification (WGA): (1) a high processivity, (2) a proofreading activity that is 1 or 2 orders of magnitude less error prone than Taq polymerase, (3) generates large fragments, over 10 kb, (4) produces more DNA than PCR-based methods, by about an order of magnitude, (5) requires a minimal amount of template, e.g. 10 ng suffices, (6) has a novel replication mechanism; multiple-strand displacement amplification, (7) random primers (e.g. hexamers) can be used so there is no need to design specific primers/target specific regions, (8) there is no need for thermal cycling, and (9) there is good coverage and a reduced amplification bias when compared to PCR-based approaches. (See Φ29 DNA polymerase, Wikipedia, 2018). The BST polymerase derived from the bacteria *Geobacillus stearothermophilus* has a helicase-like activity, making it able to unwind DNA strands. Its optimum functional temperature is between 60° C. and 65° C. and it is denatured at temperatures above 70° C. These features make it useful in loop-mediated isothermal amplification (LAMP). LAMP is similar to the polymerase chain reaction (PCR) but does not require the high temperature (96° C.) step required to denature DNA (*Geobacillus stearothermophilus*, Wikipedia, 2018).

RSE results depend on the duration of the protocol and upon a combination of choices selected from the group consisting of (a) choice of polymerase, (b) choice of polymerase concentration, (c) choice of incubation temperature given polymerase viability at the elevated temperatures, (d) choice of the DNA capture primer concentration, (e) choice of the spacing and location of DNA capture primers, (f) choice of protocol design as to the location on the forward and or reverse strand, and (g) choice of the buffer conditions, and any combination of choices thereof. By choosing the RSE reaction protocol conditions, the RSE process can be steered to either perform 'just' a labeling of the original template genomic DNA with 'one round' of biotinylated nucleotides without significant strand displacing events of any attached and extended RSA primers. This mode of RSE is preferred for preferentially pulling out the original genomic template by means of the biotinylated 'handles' attached by the RSA process. For instance this mode is valuable when the methylation or extended length of the original genomic template is of primary interest and the extended portion of the primers is only a handle to obtain such original genomic template molecules.

Alternatively, in some invention embodiments, the RSE protocol is allowed to run for extended times in order to truly start and undergo the exponential amplification process that is typical for WGA (which here remains limited to the target region of interest rather than the 'whole DNA' or 'whole genome'). In the latter mode, the time is chosen longer and the primer spacing is closer, therefore resulting in a frequent strand displacing events that start the amplification process. This mode is advantageous for application of the present invention in which a large and specific and robust amplification of the target regions is needed. This may occur when the present invention is used in forensic applications where very little genetic material is available. Elevated temperatures are useful for specificity but may seem incompatible with the choice of some enzymes typically used for WGA, such as Φ29 polymerase. However, Φ29 polymerase is perfectly viable for limited times at elevated temperatures, recognizing the fact that the polymerase will eventually stop working at temperatures that are not suitable for its long-term availability and that its error rate typically increases when operating at elevated temperatures. Typical temperatures recommended for WGA kits are 30° C. for overnight activity. It is feasible to run reactions with Φ29 polymerase at temperatures of 40° C.-50° C. for shorter times than recommended in typical WGA protocols provided changes are made to buffer conditions.

Primers do not necessarily have to be 3'-exo protected although this is preferable to increase their specificity. However, if the primers are not 3'-protected, then some of the primers will bind to positions that are only partially matched and the partially matched primers may be at least partially digested by the 3'- to 5'-exonucleolytic activity of the polymerase. This might lead to unspecific binding in case the primer is partially biding (i.e. near the 5'-end) and subsequently displaced from the template that it bound to. However this is rather unlikely due to kinetic constraints of the speed and processivity of the polymerase. A polymerase can polymerize or digest a section of 15-25 bases, which is a typical and preferred primer length, in a fraction of a second. However, it is unlikely that a non-specifically bound primer will be displaced by a second non-specifically bound primer that can then hybridize to become long enough to be found by a polymerase which could bind to it and use it to do a DNA extension upstream of the second non-specifically bound primer.

For the present invention, it is preferred to use non-3'-protected primers. Some embodiments of invention have a preference wherein the DNA primer extension process uses short capture primers that have a length (in terms of the number of nucleotide bases in the primer) which is selected from the group consisting of 5 bases, 6 bases, 7 bases, 8 bases, 9 bases, 10 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31q bases, 32 bases, 33 bases, 34 bases, 35 bases, 36 base, 37 bases, 38 bases, 39 base, 40 bases, 41 base, 42 bases, 43 bases, 44 bases, 45 bases, 46 bases, 47 bases, 48 bases, 49, bases, 50 bases and any combination thereof. For some embodiments of the present invention the short capture primers are preferably between about 12 to about 28 bases in length or between about 15 to about 25 bases in length.

Processivity is the average number of nucleotides added by a polymerase enzyme, such as DNA polymerase, per association event with the template strand. In other words, processivity is an enzyme's ability to catalyze "consecutive reactions without releasing its substrate. Because the binding of the polymerase to the template is the rate-limiting step in DNA synthesis, the overall rate of DNA replication during S phase of the cell cycle is dependent on the processivity of the DNA polymerases performing the replication. DNA clamp proteins are integral components of the DNA replication machinery and serve to increase the processivity of their associated polymerases. Some polymerases add over 50,000 nucleotides to a growing DNA strand before dissociating from the template strand, giving a replication rate of up to 1,000 nucleotides per second. Polymerases interact with the phosphate backbone and the minor groove of the DNA, so their interactions do not depend on the specific nucleotide sequence. The binding is largely mediated by electrostatic interactions between the DNA and the "thumb" and "palm" domains of the metaphorically hand-shaped DNA polymerase molecule. When the polymerase advances along the DNA sequence after adding a nucleotide, the interactions with the minor groove dissociate but those with the phosphate backbone remain more stable, allowing rapid re-binding to the minor groove at the next nucleotide. As mentioned, interactions with the DNA are also facilitated by DNA clamp proteins, which are multimeric proteins that completely encircle the DNA, with which they associate at replication forks. Their central pore is sufficiently large to admit the DNA strands and some surrounding water molecules, which allows the clamp to slide along the DNA without dissociating from it and without loosening the protein-protein interactions that maintain the toroid shape. When associated with a DNA clamp, DNA polymerase is dramatically more processive; without the clamp most polymerases have a processivity of only about 100 nucleotides. The interactions between the polymerase and the clamp are more persistent than those between the polymerase and the DNA. Thus, when the polymerase dissociates from the DNA, it is still bound to the clamp and can rapidly re-associate with the DNA (See Processivity, Wikipedia, 2018).

Another embodiment of the present invention include methods for combining RSE and RSA. The same primers as described above can be used in this combination RSE and RSA method, including running the combination method in a suitable apparatus. The primers can be synthesized via light on arrays and produced in parallel at low cost, or they can be synthesized and optionally purified by conventional means (solid surface columns/chromatography). In the combined process, the process described in the Dapprich, Murphy, and Korfhage U.S. Pat. No. 8,465,925 is preferentially carried out at elevated temperatures such as 40° C.-50° C., and with a heat stable polymerase, such as BST. It is acceptable that the polymerase has 3'-exonucleolytic activity, as explained above. The reagents for these polymerase reactions can be provided in a miniaturized format, mixed, and incubated on suitable sub-features of a miniaturized apparatus such as the Voltrax™ apparatus. Thus it is contemplated that the present invention provides important method embodiments that can be conducted using a Voltrax™ apparatus.

Some embodiments of the present invention include methods for performing a pre-extraction to get rid of components that are unwanted before the 'real' RSE or RSA or RSE & RSA. Some embodiments of the invention use no primers at all to tag all unwanted free 3'-ends that are extendable and may contribute to off-target capture, use sheared Cot-1 DNA as primers to remove repeat elements, use potentially short (hexamer or longer) primers designed against typical repeat elements to selectively pull out repeats if desired.

Some embodiments of the present invention include methods for performing pre-extension with terminating nucleotides (ddNTPs) to repair any strand breaks and unwanted free 3'-ends that are extendable and may contribute to off-target capture, perform end repair (for instance with kits such as PreCR™ and others, see NEB)

Some embodiments of the present invention include methods for using non-extendable blocking oligonucleotide ("oligos") that are preferentially longer or that have a higher GC (GC means Guanosine, Cytosine) content than the typical primers used for RSE. Longer or higher GC content primers bind more strongly to the repeat elements and will discourage any RSE primers from binding during the hybridization, enzymatic elongation and extraction steps. In this way cross-hybridization of similar repeat elements located on different chromosomes can be prevented. If such cross-hybridization is not controlled then the off target capture (off-target capture is when there is a binding of single stranded repeat elements of one chromosomal DNA target segment by annealing to a fragment from a non-targeted segments that contains a similar repeat sequence). Given the frequency with which such repeat elements occur in many genomes (e.g. many types of SINE, LINE, Transposons) cross hybridization is relatively common problem that needs to be addressed in RSE.

Some embodiments of the present invention include methods for performing the binding, washing and elution steps at elevated temperatures to increase specificity.

Some embodiments of the present invention include methods for purposely shearing or cutting genomic DNA to reduce the likelihood of cross hybridization based on the concept that a smaller fragment of a cross-hybridization targeted has a smaller likelihood of having a repeat elements (included in it overhanding sequences, but of course this restricts the overall availability of long segments).

Some embodiments of the present invention include methods for using butting primers to enhance kinetics and specificity of binding. This has the benefit that the two butting short oligonucleotides cooperatively bind with much greater speed and stability than can single primers. This method is applicable to enhance both to RSE and RSA. Some embodiments of the present invention include methods for using butting primers as a design to enhance kinetics and efficiency of capture. If the underlying sequence has high specificity, then both or more than two butting primers may be synthesized without any 3-'end protection. Of course there is the risk that one of the primers may also bind to an off-target sequence. If no two or more primers can be found that are all individually specific to the target sequence, any primers that are not to be extended (but that are supposed to guide the extendable primer to the right place) can be 3'-end protected. This is a method for avoiding binding to other non-targeted locations of the genome so that consequently such sequences are not "pulled out."

Some embodiments of the present invention include methods for using an enzyme linked to the primer for increasing the specificity so that ideally only primers get extended but not nicks or other extendable sections but where no primer is bound.

Some embodiments of the present invention include methods for using magnetic beads of a suitable bead diameter and a suitable number of bead rotations for winding around the bead surface the DNA that has become linked to the bead during primer extension. For example, 1 um ("urn" mean micron) beads which have a 3 urn circumference can wind up a DNA strand of hypothetical length 10 kb which is 3.4 um microns long needs only one winding turn by the 1 um bead to spool 10 kb of DNA nucleotides. For example, a DNA strand of hypothetical length 50 kb which is 17 um would need five winding turns on the 1 urn bead. A DNA strand of hypothetical length 500 kb which is 34 urn would need 50 winding turns by the 1 urn bead. It is an important embodiment of the present invention that fiber guides can be generated by using a rotating magnetic field and used for 'spooling' very long DNA on the magnetic bead rotating in the rotating magnetic field. The same process can be reversed for getting the DNA off the beads again.

Other modifications of the present invention include the following methods. (1) Enzymatic extension can create longer handle with more biotins and better stabilization of the genomic DNA than a biotinylated probe that is NOT enzymatically extended. (2) GB can space their primers much further apart and need less knowledge of DNA target sequence. (3) Pre-extraction can be used to pull out broken DNA by doing extension without primers—extending broken 3' ends. (4) Short primers specific to repeats (e.g. 6 base pairs long) can be used to remove repeats and one can go down to very short primers with lower annealing temperatures. (5) There is the choice to use non-magnetizable beads (paramagnetic) in the embodiments of the present invention where the magnetic bead needs to be moved to the DNA or to spool (wind) up the DNA on the bead as the bead rotates. (6) There is the option of using multiple primers along the length of the DNA extension process. (7) When primers are short it is easy to find good primer binding sites in most genomic regions, even in regions where the DNA sequence is highly repetitive. (8) Careful control of conditions to minimize DNA breakage and mechanical shearing is a major attribute of the methods of the present invention. The present invention can combine many innovations: (1) Bead rotation, (2) Active magnetic mixing, (3) DNA origami, and the combination of these three.

Some embodiments of the present invention use small beads to self-assemble on DNA ends as a means for feeding the DNA for sequencing into an Oxford Nanopore sequencing device. It is contemplated that this method can also be used for sequencing RNA, mRNA, and miRNA.

Some embodiments of the present invention use Isothermal RSE with Φ29 polymerase or BST polymerase for higher specificity. BST 2.0 polymerase is more thermostable than Φ29 polymerase which is currently used in nearly all 'whole genome amplification' (WGA) kits. Using thermostable polymerases, such as BST polymerase allows for longer oligonucleotide primers to be used as primers at higher temperatures of 50° C.-60° C., rather than the 30° C. typically used for WGA. The use of the longer primer makes the DNA amplification more specific. It is possible to run the Φ29 polymerase at elevated temperatures (up to about 40° C.) for a limited time as the Φ29 polymerase loses its activity due to heat denaturation. BST and other strand-displacing polymerases are more resistant to higher temperatures. Additionally, the use of strand duplex stabilizing modifications, buffer conditions or added chemical or biochemical reagents, or a combination thereof, makes even shorter (hexamers, or 5-10 base oligos) more specific to the target sequence(s) to which they are supposed to anneal, while discouraging the annealing to other sequences that are similar but not identical. One example is Super T™ (5-hydroxybutynl-2'-deoxyuridine), a duplex-stabilizing modified base that increases oligonucleotide melting temperature. Oligonucleotides containing Super T™ can be extended normally by polymerases, including Taq polymerase, making Super T™ a useful modified base for designing short primers or probes for low-complexity, A-T rich sequences. See "Selective Whole-Genome Amplification Is a Robust Method That Enables Scalable Whole-Genome Sequencing of *Plasmodium vivax* from Unprocessed Clinical Samples" by Cowell AN[1] MBio. 2017 Feb. 7; 8(1). pii: e02257-16. doi: 10.1128/mBio.02257-16. This application incorporates by reference in its entirety this article where Selective Whole-Genome Amplification Is a Robust Method That Enables Scalable Whole-Genome Sequencing of *Plasmodium vivax* from Unprocessed Clinical Samples. Cowell AN' MBio. 2017 Feb. 7; 8(1). pii: e02257-16. doi: 10.1128/mBio.02257-16.

Some embodiments of the present invention use "Helper oligonucleotides" for improving capture efficiency. In RSE (region-specific extraction), longer primers provide better extraction yields than short primers because they are less prone to be thermodynamically displaced from their template sequence (which usually is denatured genomic DNA) through 'breathing' and subsequent reannealing of the denatured DNA template. DNA loop-formation and loop-stabilizing agents, protective proteins or other protective agents that help coil, loop, condense, store, wind up, coat DNA before or after it has been tagged with biotins or other tag molecules also increase the ability of the annealed primer-template duplex, thereby lead to a greater rate of biotinylation and a resulting higher extraction yield. Examples are: single strand binding (SSB) proteins, histones or histone-like proteins, HU/HF proteins, other proteins binding to nucleic acids as identified by electrophoretic mobility shift assays (EMSA), Cot-1 DNA, or combinations thereof. Modifications of the primers or oligonucleotides or helper oligonucleotides also increase the ability of the annealed primer-template duplex, thereby lead to a greater rate of biotinylation and a resulting higher extraction yield. Examples of suitable modifications are locked nucleic acids (LNAs) or peptide nucleic acids (PNAs), 5-hydroxybutynl-2'-deoxyuridine, and others, or combinations thereof. Examples are also combinations of the agents and modifications of primers or oligonucleotides mentioned above.

Short (10-15 bases, or 15-20 bases, but also 20-25 bases in length) primers typically have a better ability to distinguish between slight sequence variations within the target sequence to which the primers anneal.

Primers that butt up against each other also provide better extraction yield and can at the same time be used to enhance the selective extraction of the targeted sequence for an improved distinction between similar alleles/haplotypes and sequences containing different polymorphisms (such as SNPs) or paralogous sequence variants (PSVs). This is done through the use of short 3'-end primers (such primers with a length preferably between 5 and 10 bases or between 10 and 15 bases, but also between 5 and 10 bases, or between 15 and 20 bases, and between 20 and 25 bases) with an extendable 3'-end an in combination with one or more secondary 'helper' oligonucleotides that are designed to hybridize immediately upstream, in other words directly before the extendable primer. The secondary helper oligonucleotides have a length preferably between 15 and 20 bases or between 20 and 25 bases, but they can also have lengths between 5 and 10 bases or between 10 and 15 bases, as well as longer than 25 bases.

The secondary helper oligonucleotides are preferably protected at their 3'-ends from both enzymatic elongation and digestion through the use of suitable chemical modifications, such as phoshorothioate bonds, inverted dTs, Dideoxy-C(ddC), or a combination thereof. The phosphorothioate bond substitutes a sulfur atom for a non-bridging oxygen in the phosphate backbone of an oligonucleotide, which renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds throughout the entire oligo will help reduce attack by endonucleases as well. Inverted dT can be incorporated at the 3'-end of an oligo, leading to a 3'-3' linkage which inhibits both degradation by 3' exonucleases and extension by DNA polymerases. Dideoxycytidine (ddC) is a 3' chain terminator that prevents 3' extension by DNA polymerases.

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

FIG. 1 in accordance with one embodiment of the present invention lists 8 uses for long-read sequence capture of a DNA and/or an RNA sample. These example applications are made more accurate and comprehensive when DNA enrichment is conducted with long read sequences, as opposed to short fragment enrichment, amplification and sequencing. A lot of complex regions in the genome cannot be accurately assembled with unenriched short read data and with short fragment enrichment methods.

FIG. 2 in accordance with one embodiment of the present invention shows many different methods exist for isolating nucleic acid material. The quality of the DNA material that can be obtained from a sample depends greatly on the initial storage and handling conditions both of the original sample, such as a blood or tissue buccal swab or cell line sample, as well as on the type of DNA or RNA extraction method that is used to prepare the material. For the purpose of long DNA fragment enrichment it is critical that both the initial sample is stored and handled correctly and the DNA extraction process is selected and carried out in a way that maximally retains long molecular DNA segments. It is important as well that the isolated DNA is not allowed to become entangled during enrichment or at any step thereafter in order to avoid an increase in off-target capture during extraction.

FIG. 3 in accordance with one embodiment of the present invention depicts in a highly schematic form, a short section of a single stranded DNA 301 with a 5' end nucleotide cytosine base 306, a modified adenine nucleotide base 302, a modified thymidine nucleotide base 303, a modified cytosine nucleotide base 304, and a modified cytosine nucleotide base 305. The 3' end of the single stranded DNA 301 is a thymidine nucleotide 307

Figure 4:
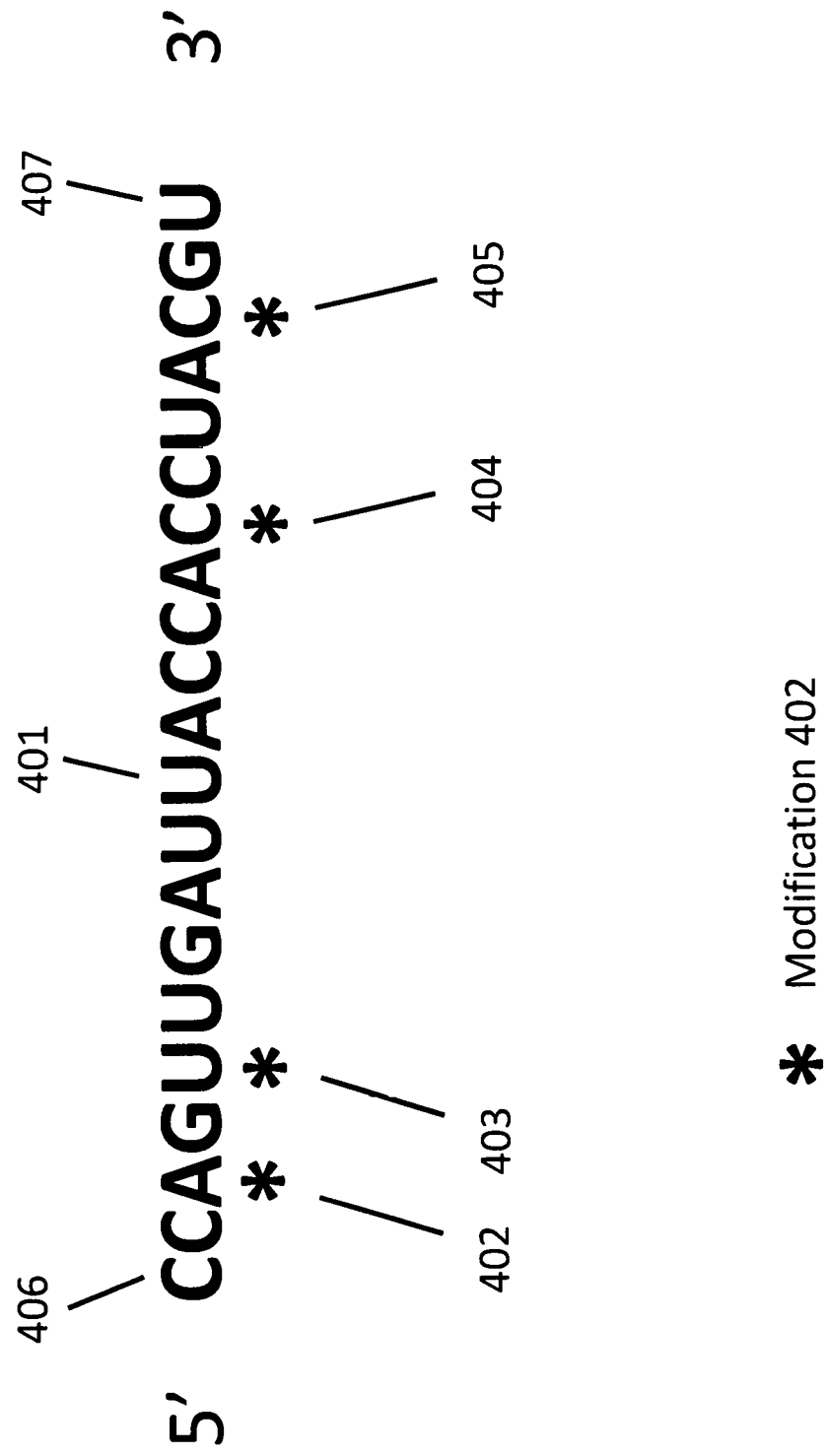
FIG. 4 in accordance with one embodiment of the present invention depicts in a highly schematic form, a short section of a single stranded RNA 401 CCAGUUGAUUACCACC-UACGU (SEQ ID NO 2) which bears similarities to short section of a single stranded DNA 301 in FIG. 3. Short single strand 401 differs from short single strand 301 by the former having a uracil nucleotide base instead of a thymidine nucleotide base 403 and a uracil nucleotide base 407 instead of a thymidine nucleotide base 307. The 5' end of both single DNA strand 301 in FIG. 3 and the 5' end 406 of single DNA strand 401 are both a nucleotide cytosine base 306, 406. The modified adenine nucleotide base 302 and 402 are the same, as are the modified cytosine nucleotide base 304, and 404.

FIG. 4 in accordance with one embodiment of the present invention depicts in a highly schematic form, a short section of a single stranded DNA 401 which bears some many similarities to short section of a single stranded DNA 301 in FIG. 3. Short single strand 401 differs from short single strand 301 by the former having a uracil nucleotide base instead of a thymidine nucleotide base 403 and a uracil nucleotide base 407 instead of a thymidine nucleotide base 307. The 5' end of both single DNA strand 301 in FIG. 3 and the 5' end 406 of single DNA strand 401 are both a nucleotide cytosine base 306, 406. The modified adenine nucleotide base 302 and 402 are the same, as are the modified cytosine nucleotide base 304, and 404.

Figure 5:
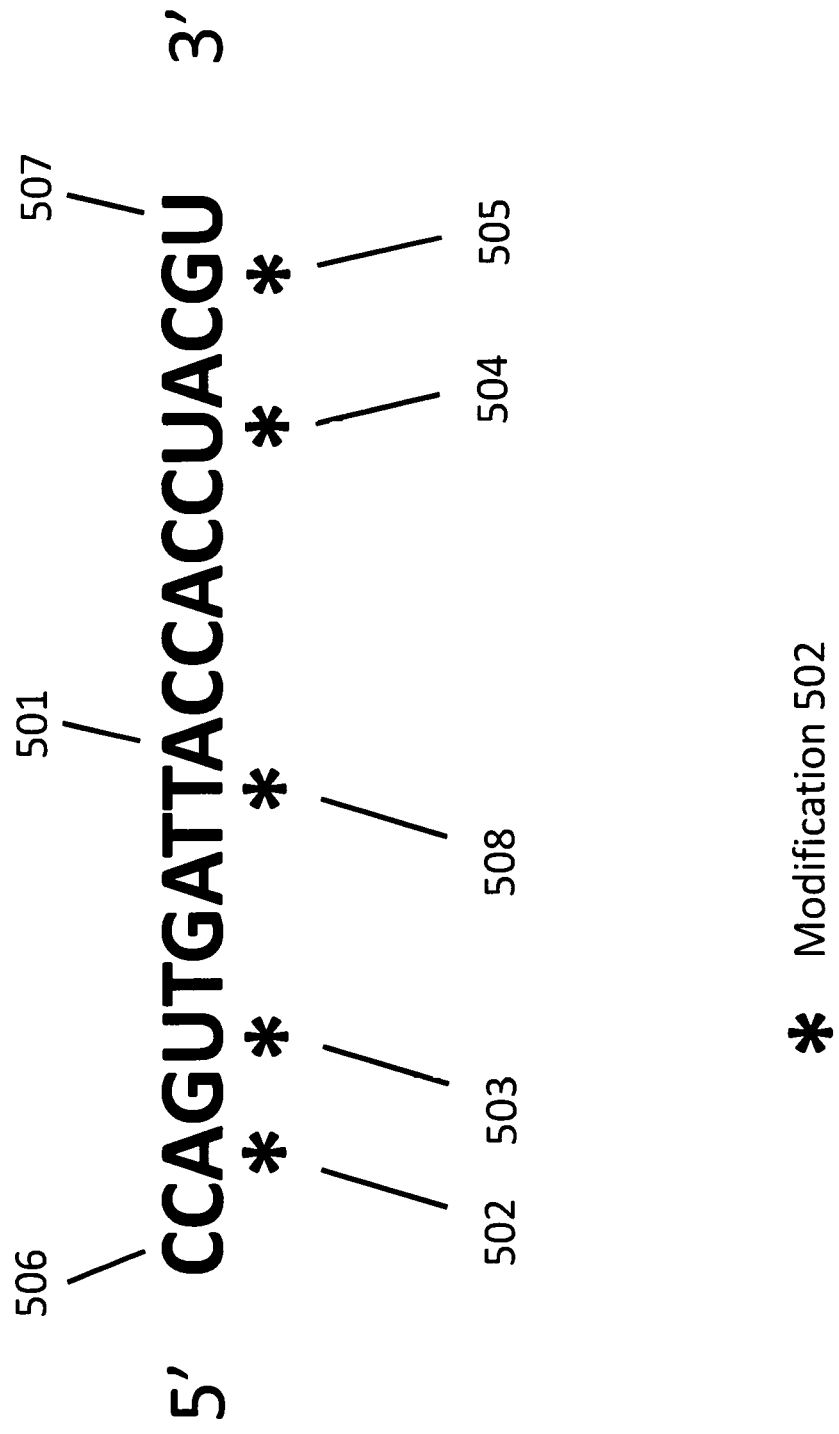
FIG. 5 in accordance with one embodiment of the present invention depicts in highly schematic form, an example capture primer 501 CCAGUTGATTACCACCUACGU (SEQ ID NO 3) with 5' end cytosine nucleotide base 506 and 3' end uracil nucleotide base 507. Modified nucleotide bases are numbered 502, 503, 504, 505, and 508.

FIG. 5 in accordance with one embodiment of the present invention depicts in highly schematic form, an example capture primer 501 with 5' end cytosine nucleotide base 506 and 3' end uracil nucleotide base 507. Modified nucleotide bases are numbered 502, 503, 504, 505, and 508.

Figure 6:
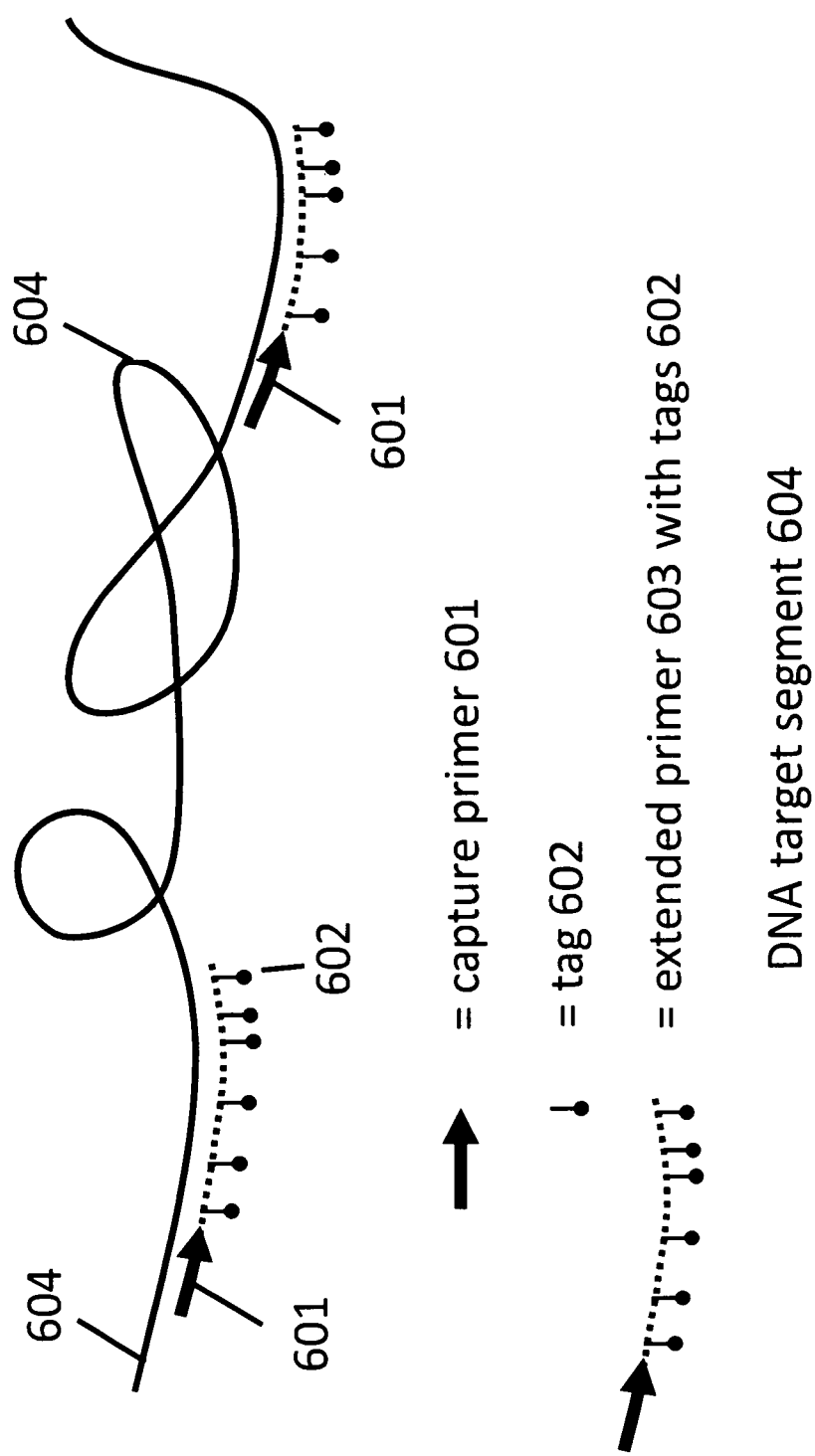
FIG. 6 in accordance with one embodiment of the present invention depicts a capture primer 601 that has been enzymatically extended as extended primer 603 with tags 602 after binding to a genomic DNA template molecule 604. Depicted are two specific RSE capture primers 601 hybridized to specific sequences in the genomic template 604. Optionally a primer can be an extendable 3'-end of a double-stranded DNA molecule, wherein the 3'-end can be enzymatically extended with a 5'-overhang of the double-stranded DNA molecule acting as the genomic template for the incorporation of at least one nucleotide or biotinylated nucleotide.

FIG. 6 in accordance with one embodiment of the present invention depicts a capture primer 601 that has been enzymatically extended as extended primer 603 with tags 602 after binding to a genomic DNA template molecule 604. Depicted are two specific RSE capture primers 601 hybridized to specific sequences in the genomic template 604. Optionally a primer can be an extendable 3'-end of a double-stranded DNA molecule, wherein the 3'-end can be enzymatically extended with a 5'-overhang of the double-stranded DNA molecule acting as the genomic template for the incorporation of at least one nucleotide or biotinylated nucleotide.

Figure 7:
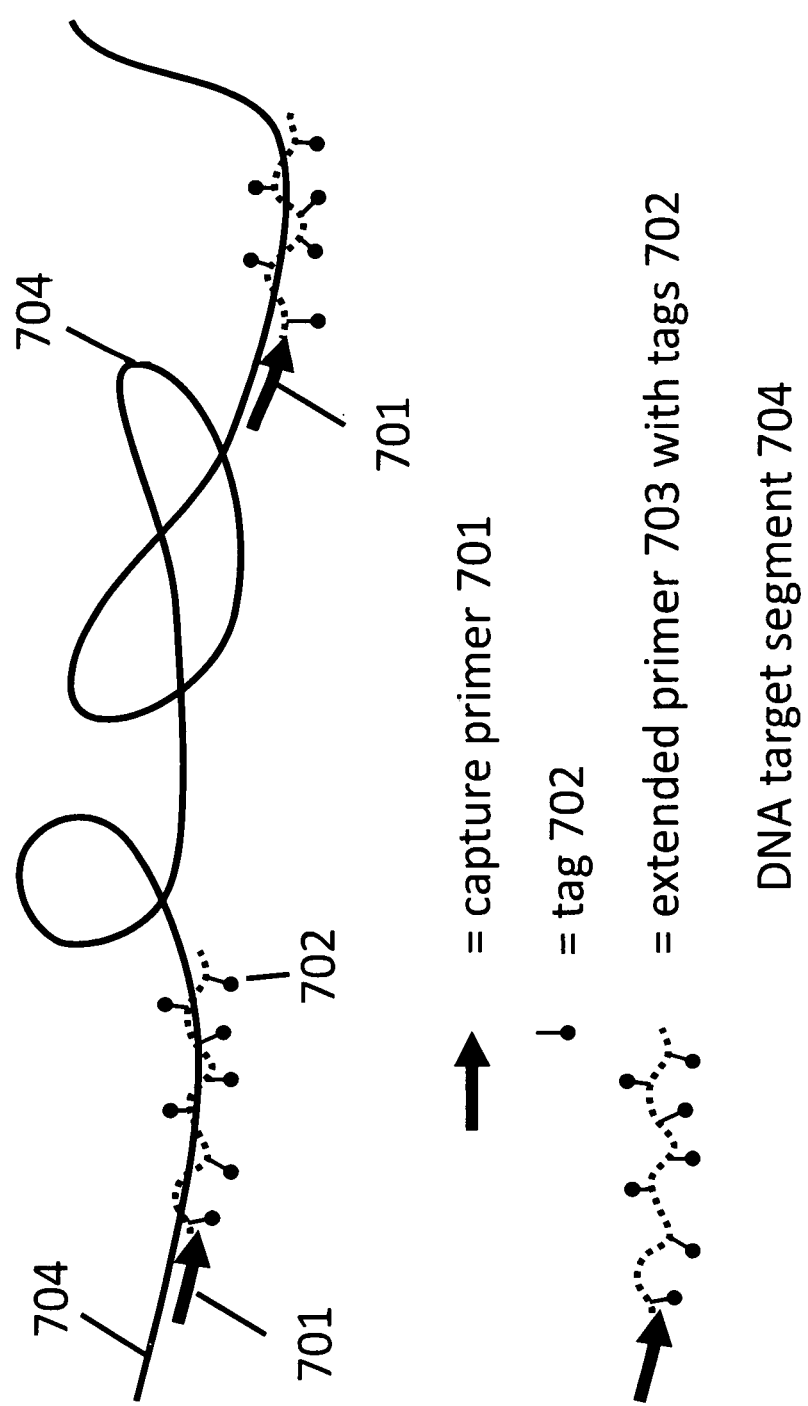
FIG. 7 in accordance with one embodiment of the present invention shows a capture primer 701, the extended primer 703 with the tags 702 is wrapped around the genomic template due to the double helix forming nature of DNA and RNA, and a DNA target segment 704.

FIG. 7 in accordance with one embodiment of the present invention shows a capture primer 701, the extended primer 703 with the tags 702 is wrapped around the genomic template due to the double helix forming nature of DNA and RNA, and a DNA target segment 704.

Figure 8:
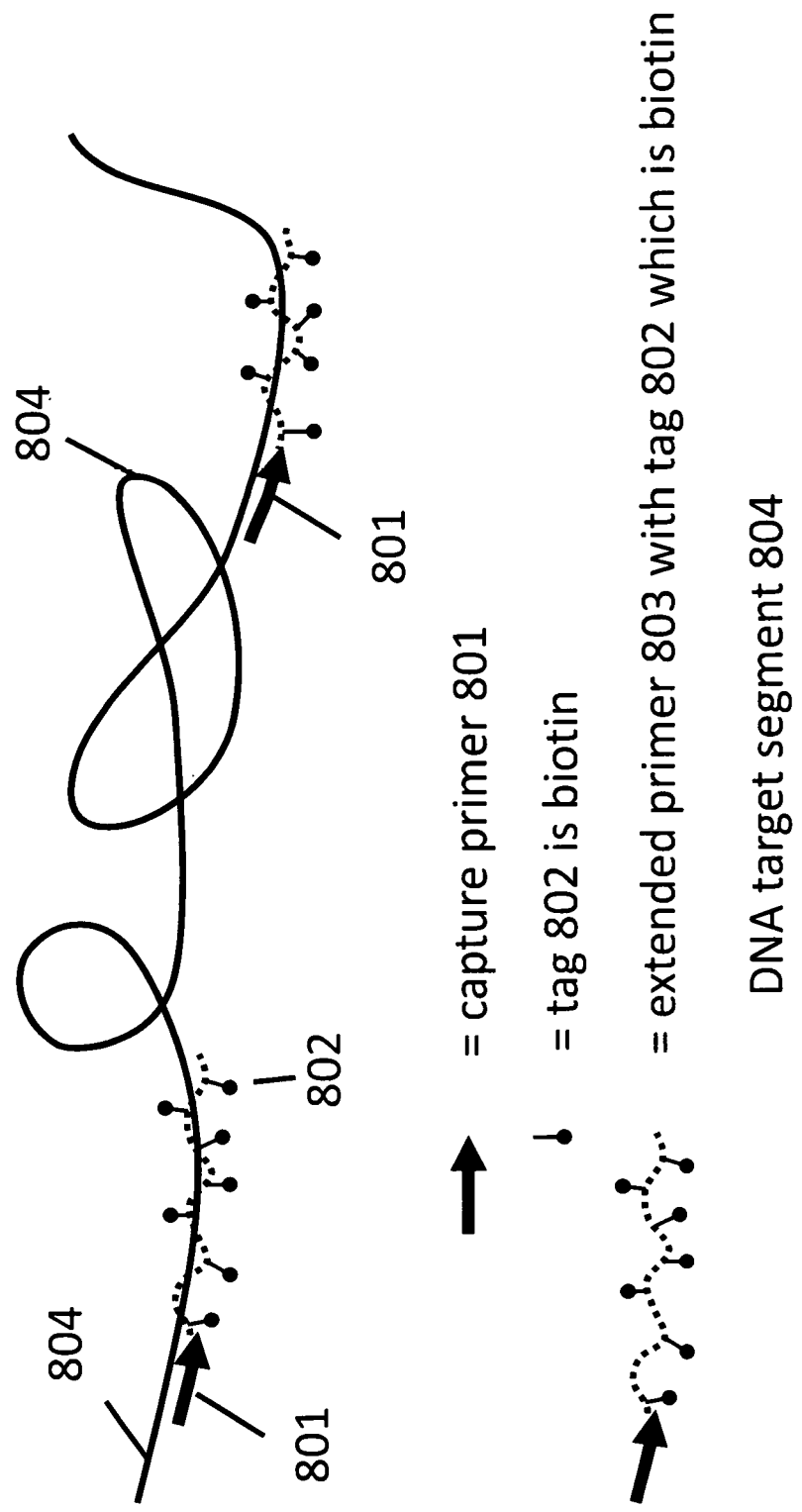
FIG. 8 in accordance with one embodiment of the present invention shows a capture primer 801, the genomic template molecule 804 with extended RSE capture primers 803 that are elongated and wrapped around the template strand including the incorporated tags 802 which are biotin.

FIG. 8 in accordance with one embodiment of the present invention shows a capture primer 801, the genomic template molecule 804 with extended RSE capture primers 803 that are elongated and wrapped around the template strand including the incorporated tags 802 which are biotin.

Figure 9:
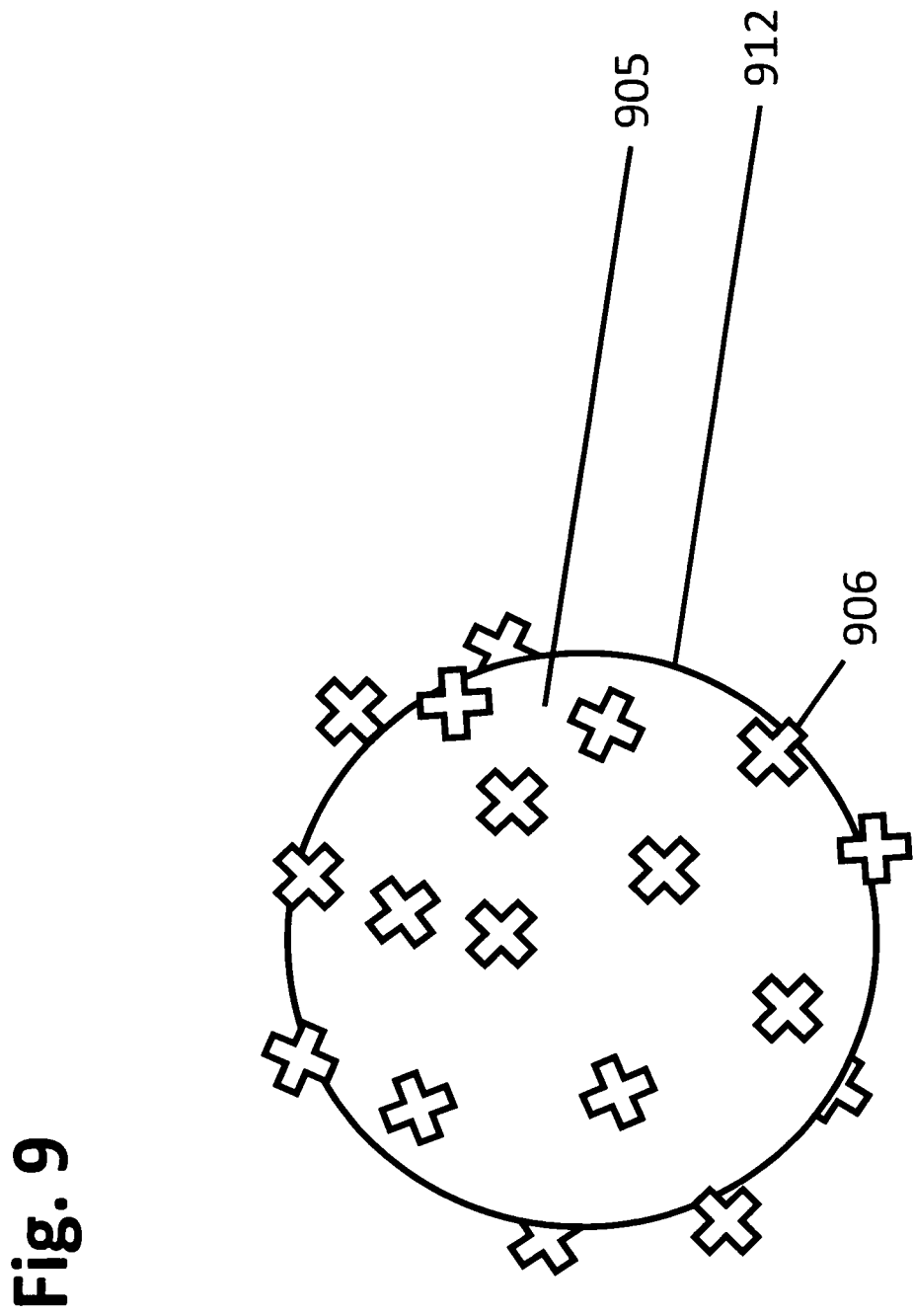
FIG. 9 in accordance with one embodiment of the present invention depicts a magnetic nanoparticle or bead 905 that contains multiple streptavidin moieties 906 that are bound to the bead surface 912.

FIG. 9 in accordance with one embodiment of the present invention depicts a magnetic nanoparticle or bead 905 that contains multiple streptavidin moieties 906 that are bound to the bead surface 912.

Figure 10:
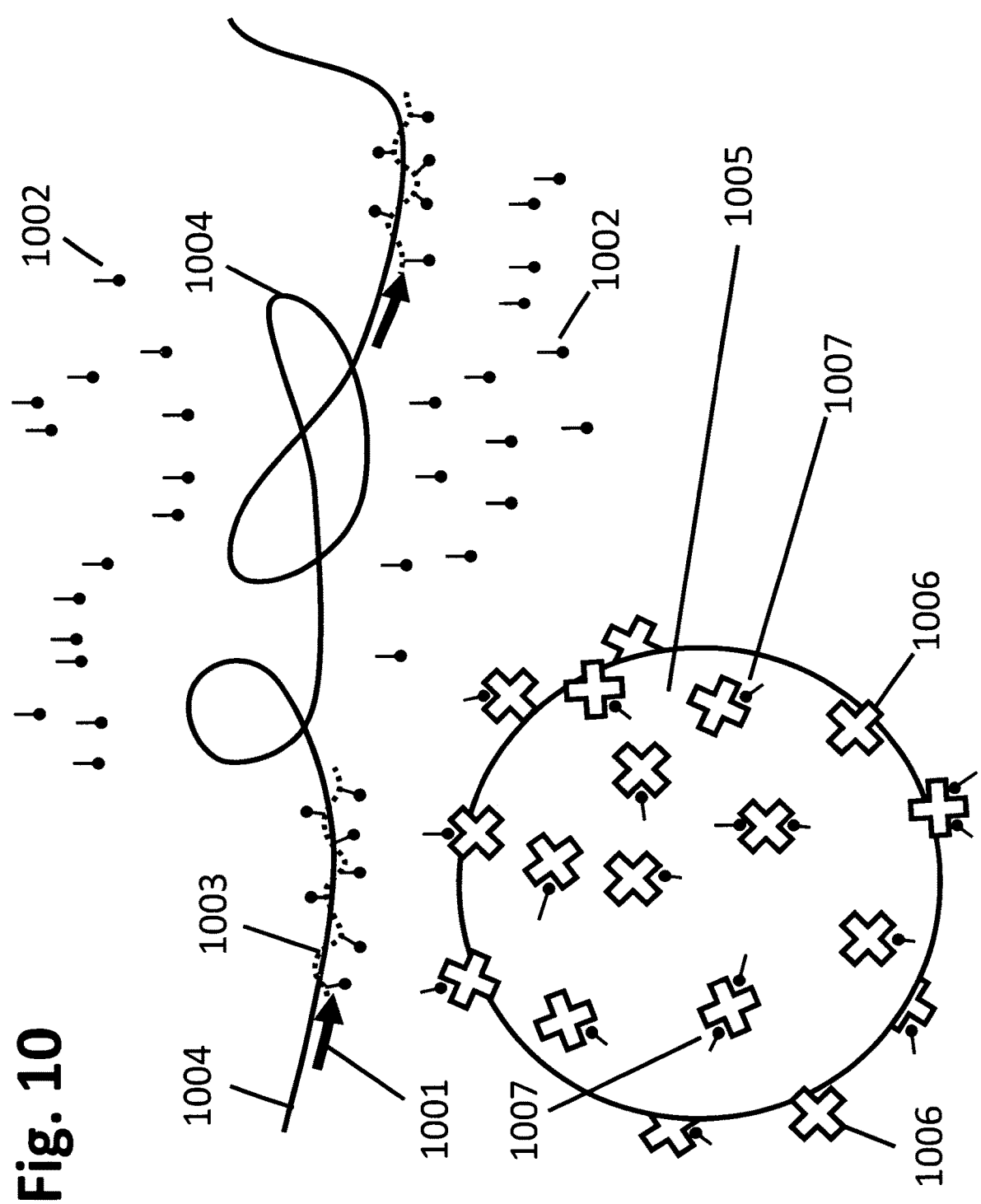
FIG. 10 in accordance with one embodiment of the present invention depicts a streptavidin coated magnetic bead 1005 in the presence of a genomic template 1004 with two bound and extended RSE capture primers 1001 containing multiple incorporated biotin tags 1002 in the extended portion 1003 of the primers. In addition to the biotin tags that are incorporated into the extended RSE primers, there are free biotin tags in solution 1002. These free biotin tags diffuse much more quickly due to the smaller size when compared to the extended biotin elated tags on the genomic DNA template. The probability of the free biotin tags 1002 contacting the streptavidin moieties 1006 on the magnetic bead and binding to them is much greater than the probability of the incorporated biotin tags 2 find to the streptavidin on the magnetic beads through diffusion alone. The bound free biotin 1007 consequently block a large number of the available biotin binding sites on these trapped streptavidin moieties on the magnetic beads, making them no longer available for binding to the biotin tags that are incorporated into the extended RSE primer that is bound to the targeted genomic template molecule.

FIG. 10 in accordance with one embodiment of the present invention depicts a streptavidin coated magnetic bead 1005 in the presence of a genomic template 1004 with two bound and extended RSE capture primers 1001 containing multiple incorporated biotin tags 1002 in the extended portion 1003 of the primers. In addition to the biotin tags that are incorporated into the extended RSE primers, there are free biotin tags in solution 1002. These free biotin tags diffuse much more quickly due to the smaller size when compared to the extended biotin elated tags on the genomic DNA template. The probability of the free biotin tags 1002 contacting the streptavidin moieties 1006 on the magnetic bead and binding to them is much greater than the probability of the incorporated biotin tags 2 find to the streptavidin on the magnetic beads through diffusion alone. The bound free biotin 1007 consequently block a large number of the available biotin binding sites on these trapped avidin moieties on the magnetic beads, making them no longer available for binding to the biotin tags that are incorporated into the extended RSE primer that is bound to the targeted genomic template molecule.

Figure 11:
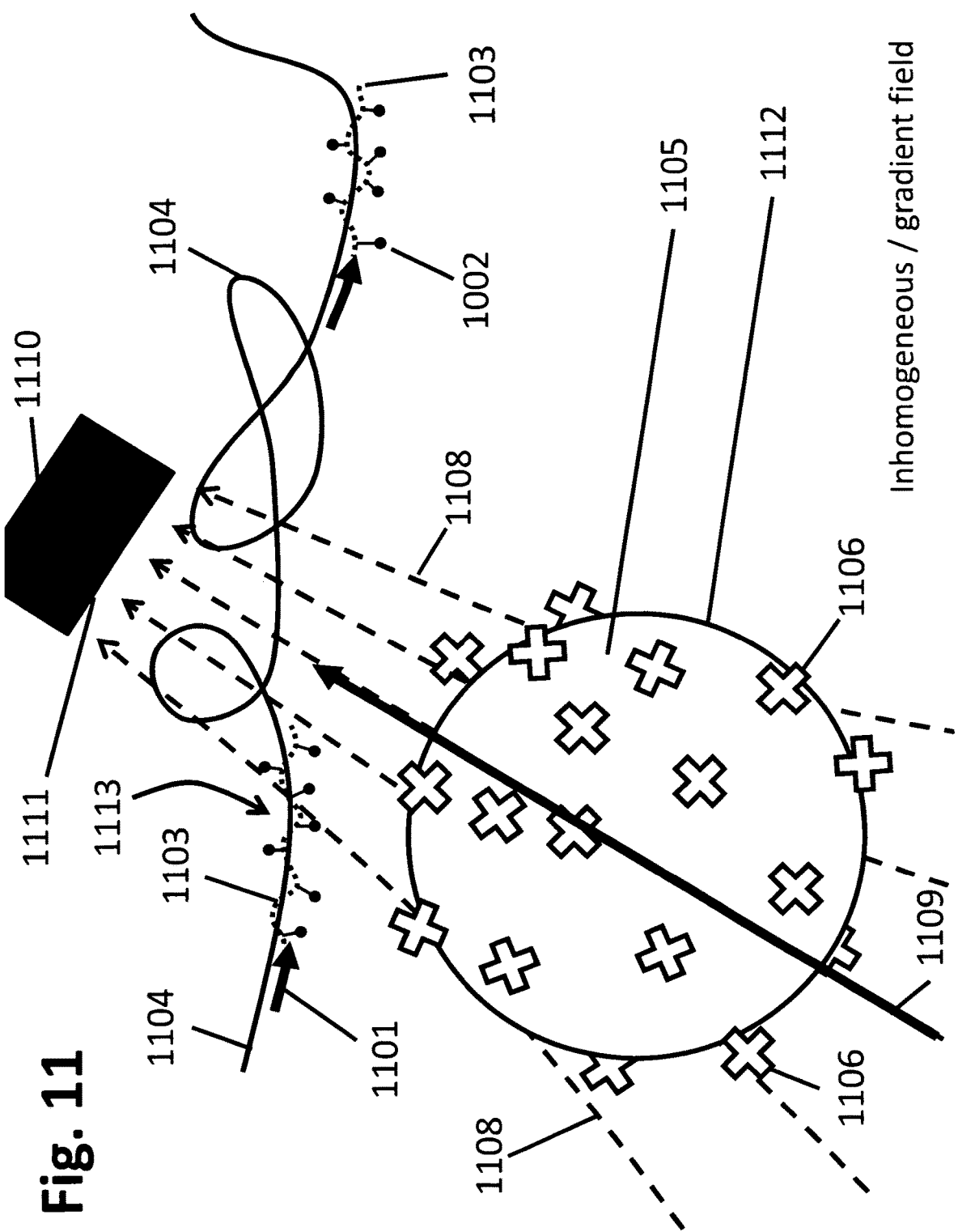
FIG. 11 in accordance with one embodiment of the present invention depicts relative magnetic motion of a streptavidin 1106 coated magnetic bead 1105 in the presence of a genomic template 1104 with two bound extended RSE capture primers 1101 containing multiple incorporated biotin tags 1102 in the extended portion 1103 and 1113 of the two primers.

FIG. 11 in accordance with one embodiment of the present invention depicts relative magnetic motion of a streptavidin 1106 coated magnetic bead 1105 in the presence of a genomic template 1104 with two bound extended RSE capture primers 1101 containing multiple incorporated biotin tags 1102 in the extended portion 1103 and 1113 of the two primers. FIG. 11 depicts the relative magnetic motion of the magnetic bead 1105 that is achieved by an inhomogeneous gradient of magnetic field lines 1108 generated by the magnet 1110. The motion of the magnetic particle 1105 is directed towards the magnet surface 1111 as indicated by the thick black arrow 1109. The gradient magnetic field lines 1108 are indicated by dashed lines converging towards the surface 1111 of the magnet 1110. By generating such relative motion of the magnetic bead through the solution, the probability that a biotin tag 1102 will encounter a streptavidin moiety 1106 on the bead surface is increased. As a result, the overall capture efficiency for genomic template molecules that contain extended RSE primers with biotin tags is greatly enhanced compare two situations where no relative motion of the magnetic bead through solution is generated. The relative motion is called active magnetic mixing when it is done through a in homogeneous mechanic field, or through a rotating homogeneous magnetic field that will create no translation of low movement of the magnetic particles but results in the formation of magnetic chains and fibers that will rotate following the rotating magnetic homogeneous field like propellers but without any translational movement toward the magnet. Alternatively the relative magnetic motion of the beads through the solution can also be achieved by non-magnetic means, for instance by centrifugation.

Figure 12:
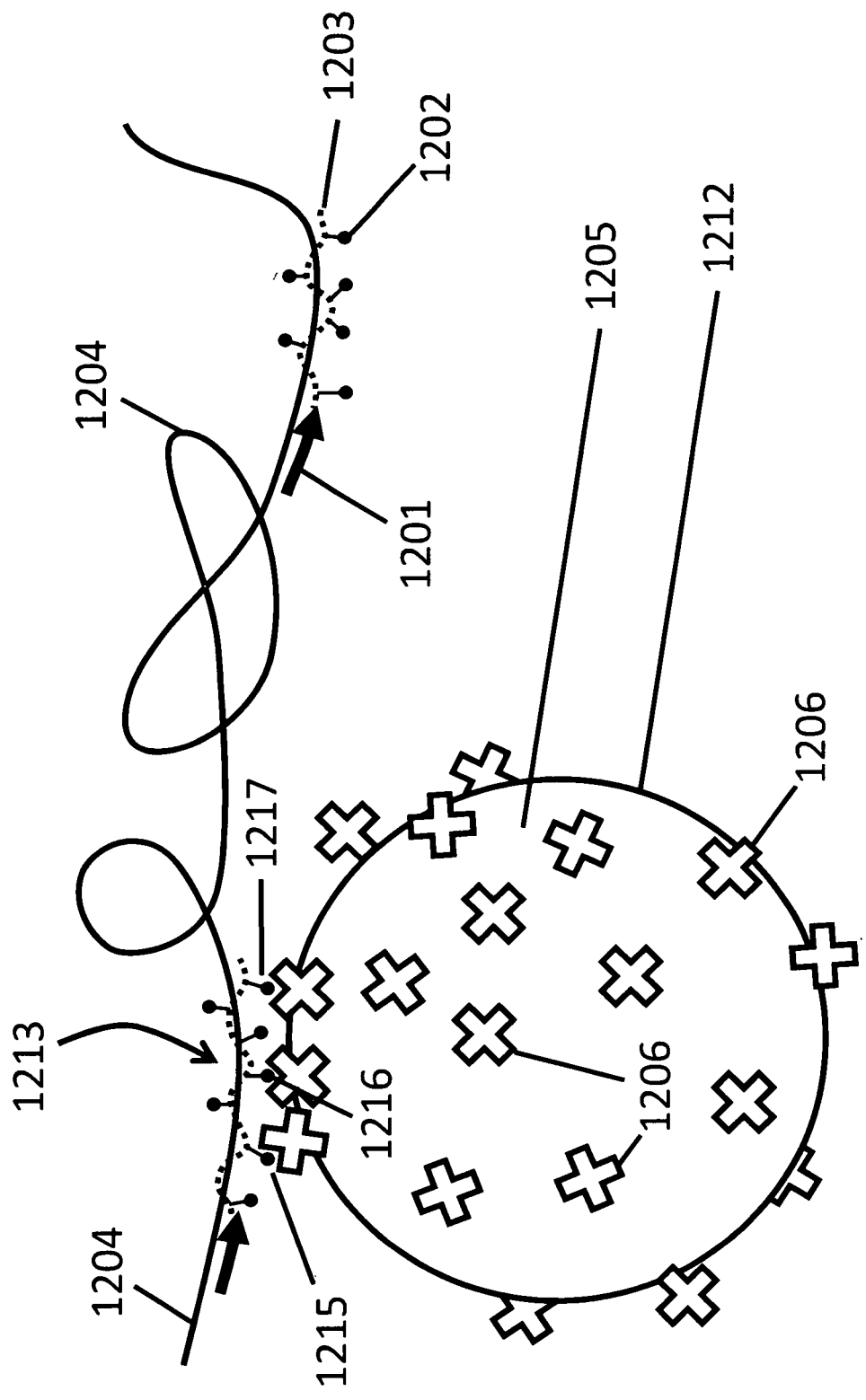
FIG. 12 in accordance with one embodiment of the present invention depicts a streptavidin 1206 coated magnetic bead 1205 in the presence of a genomic template 1204 with two extended RSE capture primers 1201 containing multiple incorporated multiple biotin tags 1202 of the extended RSE primer 1203 binding to multiple streptavidin moieties 1206 located on the magnetic particle 1205. The extended biotin alighted primer one two or three is wrapped around the genomic template 1204, as depicted by arrow 1213. Multiple biotin tags bind to different streptavidins, indicated here with numbers 1215, 1216, and 1217. As a result, the section 1213 of the genomic template 1204 located between the biotin tags bound to the streptavidin's 1215 and 1217 becomes topologically locked to the surface of the magnetic particle. This results in an almost covalent binding strength that enables the present method to isolate extremely long genomic template molecules with very high capture efficiency.

FIG. 12 in accordance with one embodiment of the present invention depicts a streptavidin 1206 coated magnetic bead 1205 in the presence of a genomic template 1204 with two extended RSE capture primers 1201 containing multiple incorporated multiple biotin tags 1202 of the extended RSE primer 1203 binding to multiple streptavidin moieties 1206 located on the magnetic particle 1205. The extended biotin alighted primer one two or three is wrapped around the genomic template 1204, as depicted by arrow 1213. Multiple biotin tags bind to different streptavidins, indicated here with numbers 1215, 1216, and 1217. As a result, the section 1213 of the genomic template 1204 located between the biotin tags bound to the streptavidins 1215 and 1217 becomes topologically locked to the surface of the magnetic particle. This results in an almost covalent binding strength that enables the present method to isolate extremely long genomic template molecules with very high capture efficiency.

Figure 13:
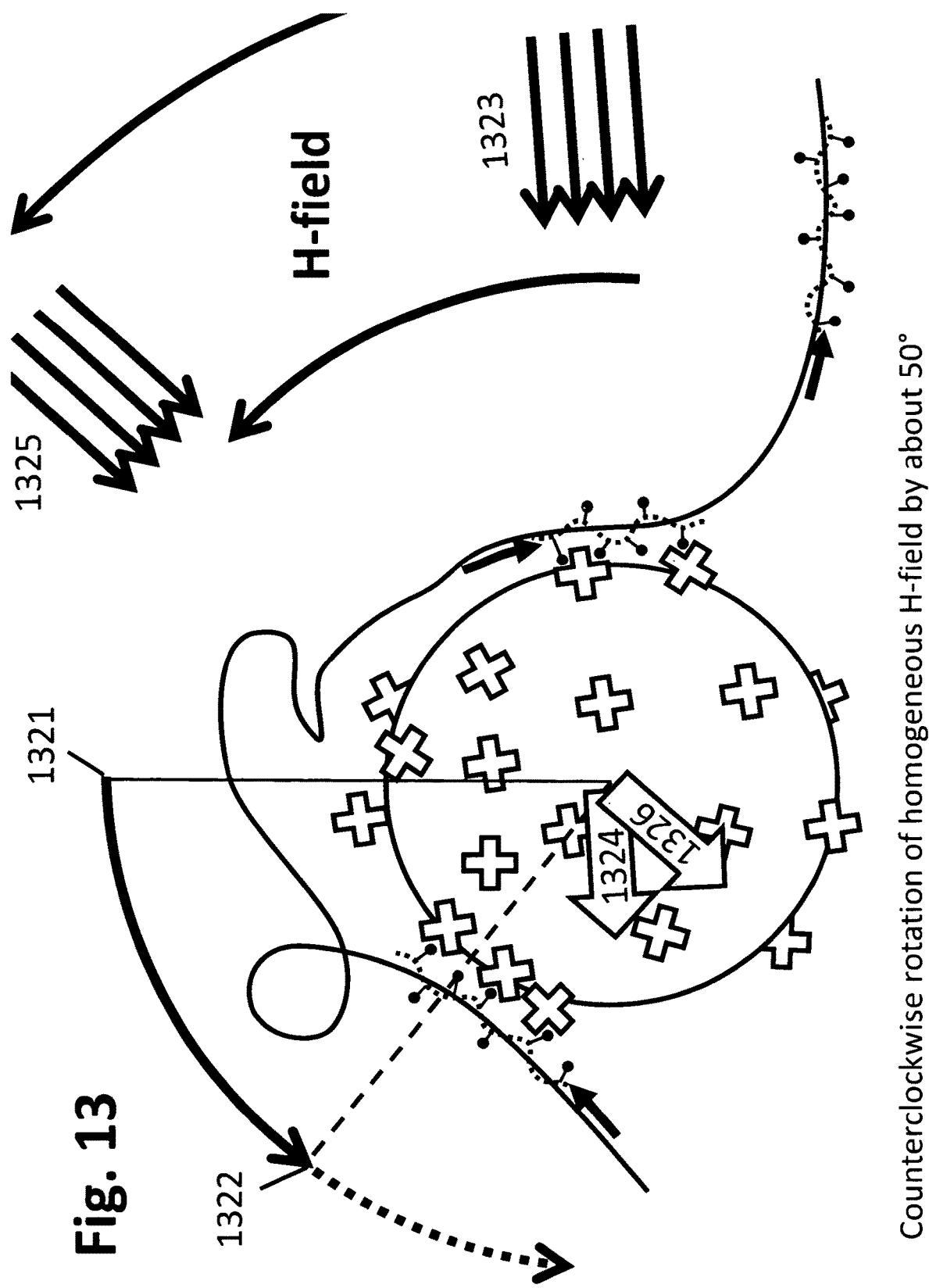
FIG. 13 in accordance with one embodiment of the present invention depicts a rotation of the magnetic beads through an external homogeneous magnetic field, indicated by the letter H and parallel arrows. 1323 pics the magnetic field before the rotation and 1325 to fix the bead after the rotation of about 50 degrees counterclockwise. As a result, the position of the magnetic bead shifts from position 1321 to 1322 and its internal magnetic moment from 1326 to 1324, as indicated by hollow white arrows in the center of the magnetic bead. The rotation of the particle in the magnetic field results in a greater likelihood of additional binding of other extended and biotin labeled primers to its surface, as well as in a winding up of the genomic template molecule that has been labeled with multiple RSE capture primers. As a further result, the overall binding affinity of the label genomic template to the bead is increased and the template is more tightly wound around to the bead, thereby reducing the likelihood of it getting damaged in subsequent process steps during the extraction protocol. The rotation of the magnetic bead therefore results in an overall higher capture efficiency of longer length genomic template molecules as compared to capture when no rotation of the beads is performed.

FIG. 13 in accordance with one embodiment of the present invention depicts a rotation of the magnetic beads through an external homogeneous magnetic field, indicated by the letter H and parallel arrows. 1323 depicts the magnetic field before the rotation and 1325 to fix the bead after the rotation of about 50 degrees counterclockwise. As a result, the position of the magnetic bead shifts from position 1321 to 1322 and its internal magnetic moment from 1326 to 1324, as indicated by hollow white arrows in the center of the magnetic bead. The rotation of the particle in the magnetic field results in a greater likelihood of additional binding of other extended and biotin labeled primers to its surface, as well as in a winding up of the genomic template molecule that has been labeled with multiple RSE capture primers. As a further result, the overall binding affinity of the label genomic template to the bead is increased and the template is more tightly wound around to the bead, thereby reducing the likelihood of it getting damaged in subsequent process steps during the extraction protocol. The rotation of the bead therefore results in an overall higher capture efficiency of longer length genomic template molecules as compared to capture when no rotation of the beads is performed.

Figure 14:
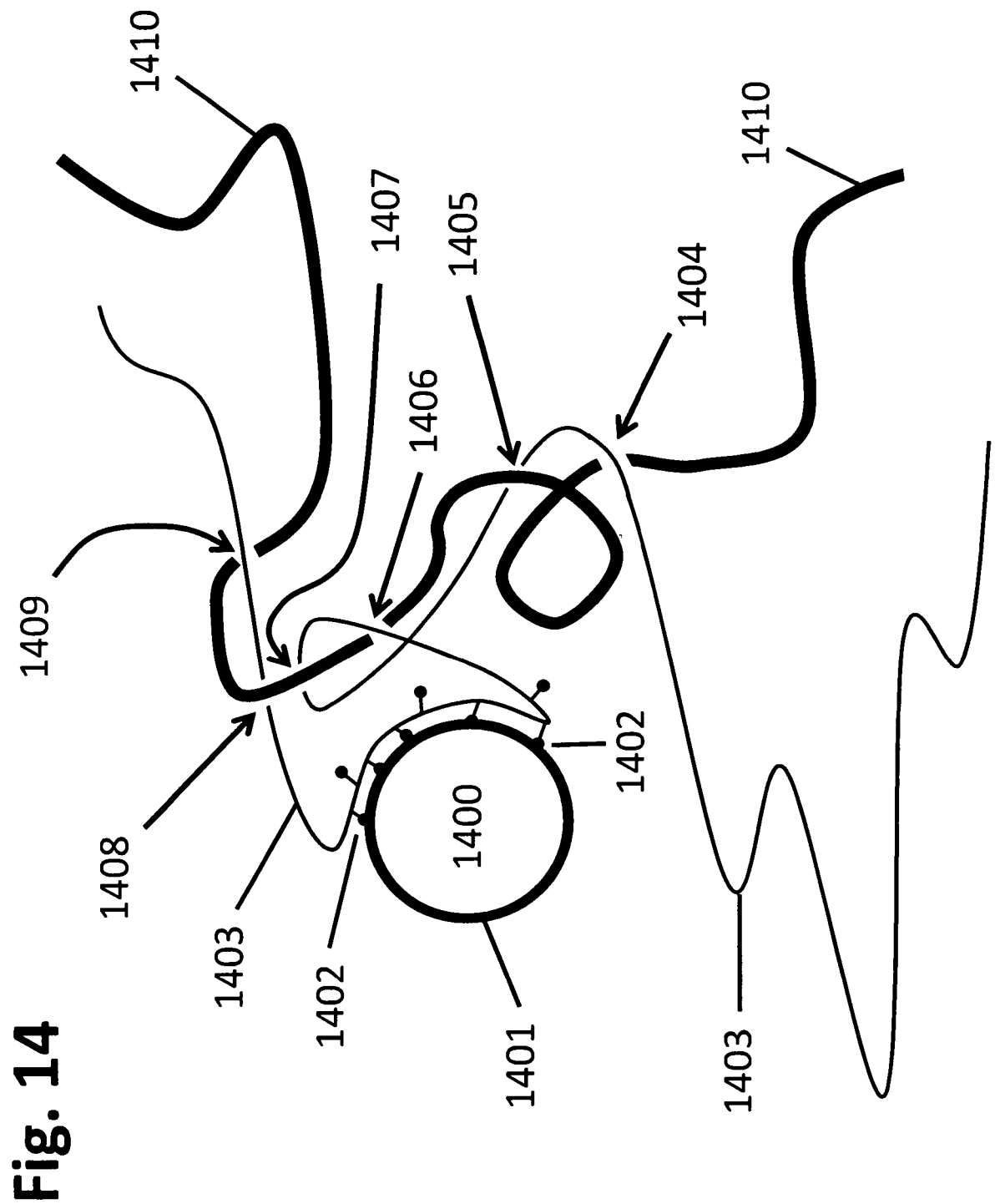
FIG. 14 in accordance with one embodiment of the present invention depicts a magnetic bead 1400 with surface 1401 that is bound with multiple biotin tags 1402 to a genomic template 1403 and the presence of a non-targeted genomic template molecule 1410 depicted in bold. Due to the random nature of DNA and its length it is likely that both On-target molecules and off-target molecules of the template genomic DNA are entangled to some degree with each other, as indicated by several crossing-over positions between the target of genomic template molecule 1403 and the non-targeted molecule 1410 at positions indicated by the arrows 1404, 1405, 1406, 1407, 1408, 1409. If the magnetic particle is removed from solution, and especially if it is moved towards the right where the non-targeted but entangled DNA template fragment is present in the picture, it is likely that the non-targeted genomic template will get isolated inadvertently along with the targeted genomic template 1403 that is directly bound to the magnetic particle through the extended and biotin tagged primer, therefore resulting in increased contributions of off-target material. Such an entanglement of off-target material with targeted DNA regions is especially likely if they DNA fragments are very long and if the template extraction is carried out in high concentrations of DNA. Any prior entanglement of the DNA during the DNA isolation procedure from the original sample can also dramatically increase the amount of off-target that is carried along during the extraction process. This is specially can occur if the genomic template DNA is at any point allowed to dry out or precipitate, in which case the entanglement between unrelated strands becomes almost impossible to reverse.

FIG. 14 in accordance with one embodiment of the present invention depicts a magnetic bead 1400 with surface 1401 that is bound with multiple biotin tags 1402 to a genomic template 1403 and the presence of a non-targeted genomic template molecule 1410 depicted in bold. Due to the random nature of DNA and its length it is likely that both On-target molecules and off-target molecules of the template genomic DNA are entangled to some degree with each other, as indicated by several crossing-over positions between the target of genomic template molecule 1403 and the non-targeted molecule 1410 at positions indicated by the arrows 1404, 1405, 1406, 1407, 1408, 1409. If the magnetic particle is removed from solution, and especially if it is moved towards the right where the non-targeted but entangled DNA template fragment is present in the picture, it is likely that the non-targeted genomic template will get isolated inadvertently along with the targeted genomic template 1403 that is directly bound to the magnetic particle through the extended and biotin tagged primer, therefore resulting in increased contributions of off-target material. Such an entanglement of off-target material with targeted DNA regions is especially likely if they DNA fragments are very long and if the template extraction is carried out in high concentrations of DNA. Any prior entanglement of the DNA during the DNA isolation procedure from the original sample can also dramatically increase the amount of off-target that is carried along during the extraction process. This is specially can occur if the genomic template DNA is at any point allowed to dry out or precipitate, in which case the entanglement between unrelated strands becomes almost impossible to reverse.

Figure 15:
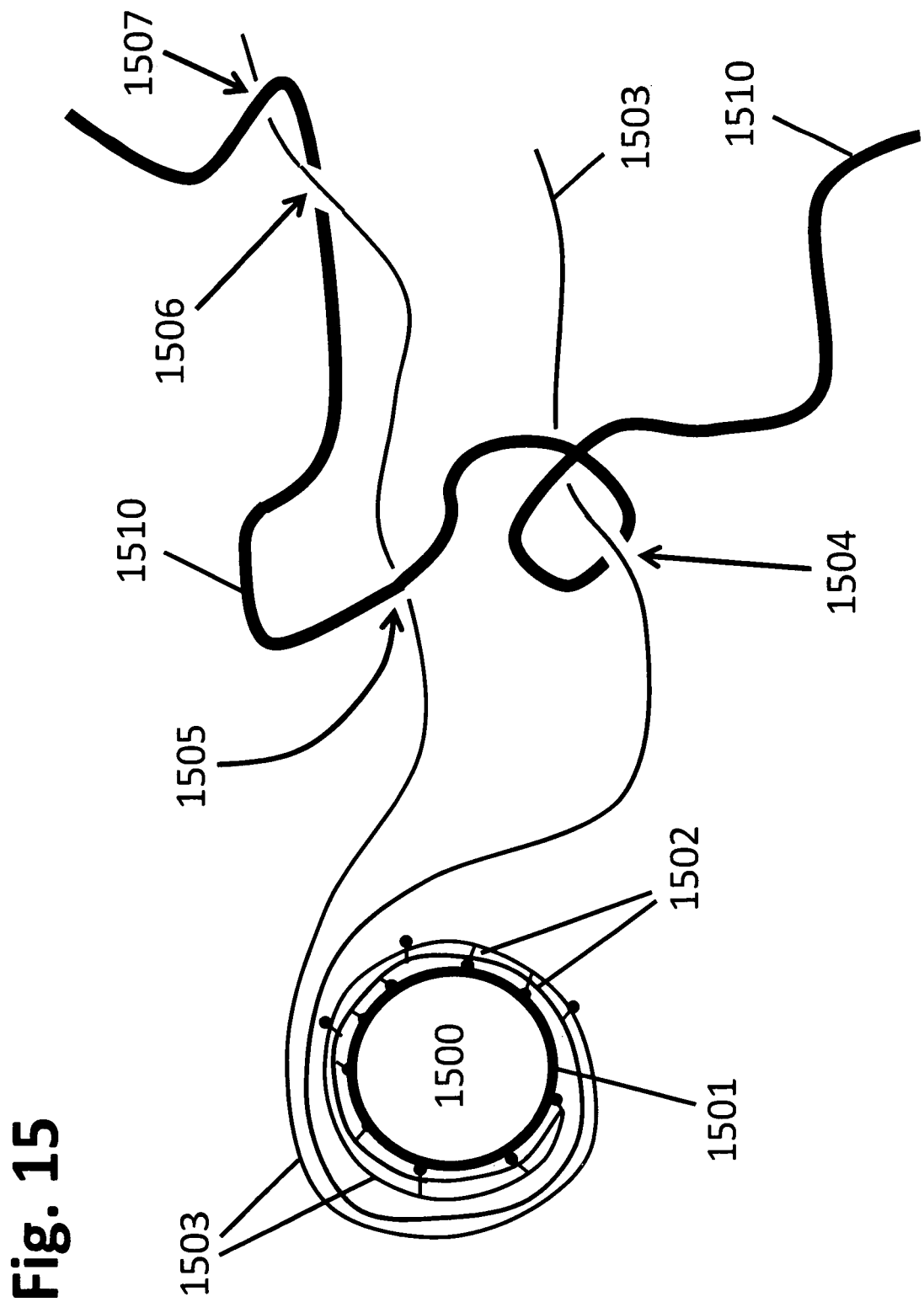
FIG. 15 in accordance with one embodiment of the present invention depicts the same situation in case of a magnetic bead 1500 that has been rotated several times counterclockwise. As a result, the targeted genomic template 1503 and the bound and extended primers with the incorporated biotin tags 1502 are bound at many positions to the surface 1501 of the bead. Due to the rotation of the magnetic bead and the successive binding of neighboring capture primers located on the same genomic target template 1503, the genomic template is linearly pulled through the solution, thereby reducing the likelihood of potential entanglements 1504, 1505, 1506, and 1507 between genomic target template 1503 and non-targeted DNA strand 1510.

FIG. 15 in accordance with one embodiment of the present invention depicts the same situation in case of a magnetic bead 1500 that has been rotated several times counterclockwise. As a result, the targeted genomic template 1503 and the bound and extended primers with the incorporated biotin tags 1502 are bound at many positions to the surface 1501 of the bead. Due to the rotation of the magnetic bead and the successive binding of neighboring capture primers located on the same genomic target template 1503, the genomic template is linearly pulled through the solution, thereby reducing the likelihood of potential entanglements 1504, 1505, 1506, and 1507 between genomic target template 1503 and non-targeted DNA strand 1510.

Figure 16:
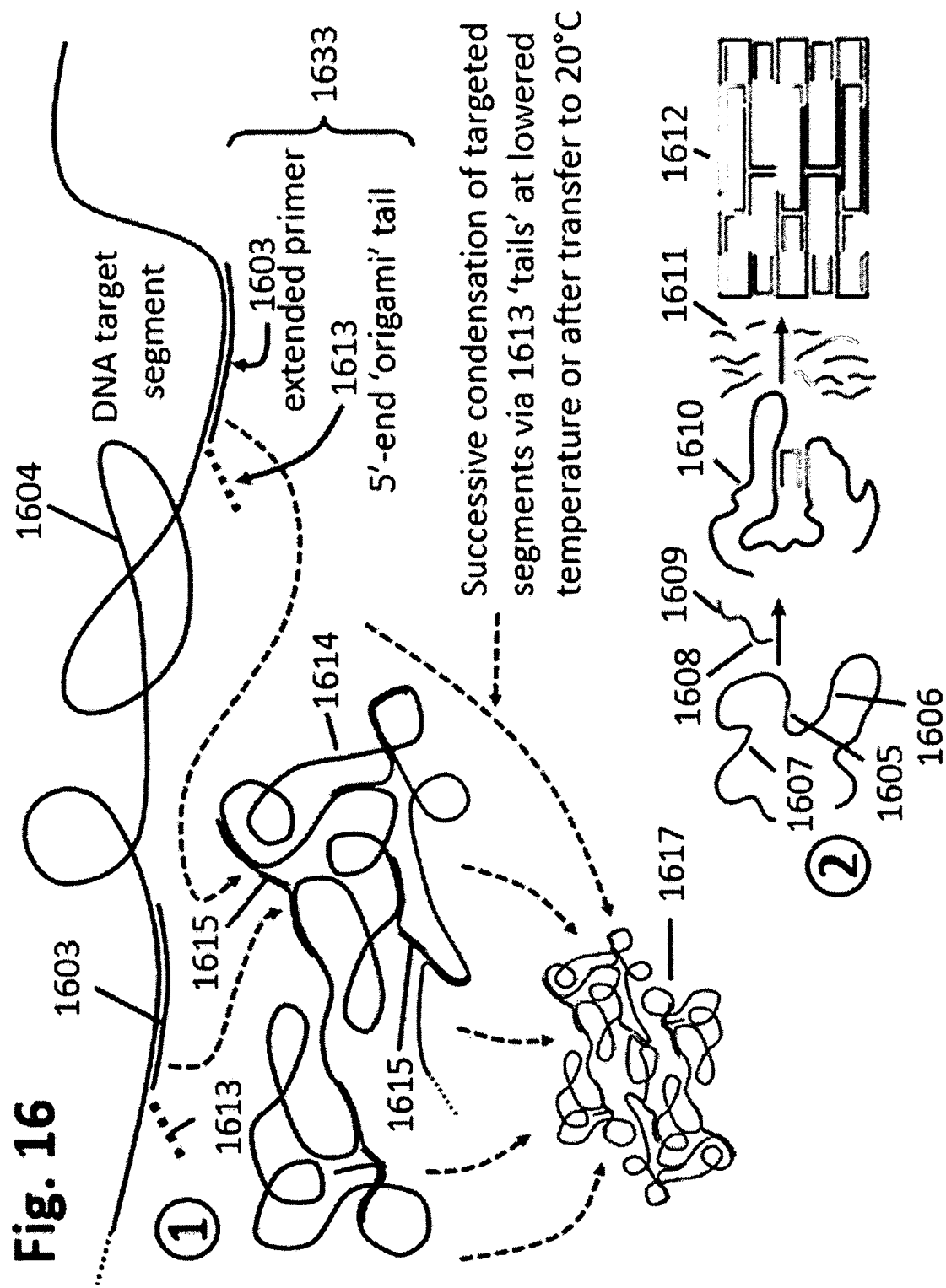
FIG. 16 at top, labeled 1, in accordance with one embodiment of the present invention depicts a genomic DNA target segment 1604 that is targeted with capture primers 1603 contain incorporated biotin tags as well as a so-called origami tail 1613 located at the five prime end of the capture primers. The origami tail 1613 does not hybridize to the DNA sequence directly in front of the capture primer binding sequence. Instead it is intended to find two other, complimentary origami tails that are connected to other extended RC capture primers for the purpose of bringing such labeled genomic template molecules 1614, together and thereby condensing the targeted molecule 1617 by forming multiple cross-linking bridges 1615 that are all bound to the same targeted DNA molecule. Labels 1615 indicate examples where 2 of the origami tails have hybridized to each other and as a consequence bring together sections of the genomic template molecule 1604 that would normally be separated by thousands or tens of thousands of bases. The hybridization temperature between origami tails 1613 is preferably chosen to be considerably lower than the hybridization and extension temperature used for the capture primers 1603. A typical hybridization and extension temperature for the capture primers is 64° C., or as the favorable temperature for hybridization of the origami tails is 20° C. or 30° C. (° C. means degrees Celsius). As a result the DNA target segment 1604 is transformed from a highly vulnerable and extended long molecule into a more compact form depicted by label 1617. Such condensed DNA target segments can be preferably created under dilute conditions to reduce the risk of any entanglement of off-target DNA molecules and are then much more robust for subsequent magnetic capture and handling so that long DNA lengths are preserved throughout the extraction and washing protocol. Label 1633 indicates the hybrid molecule consisting of extended capture primer 1603 and the attached origami tail 1613.

FIG. 16 at top, labeled 1, in accordance with one embodiment of the present invention depicts a genomic DNA target segment 1604 that is targeted with capture primers 1603 contain incorporated biotin tags as well as a so-called origami tail 1613 located at the five prime end of the capture primers. The origami tail 1613 does not hybridize to the DNA sequence directly in front of the capture primer binding sequence. Instead it is intended to find two other, complimentary origami tails that are connected to other extended RC capture primers for the purpose of bringing such labeled genomic template molecules 1614, together and thereby condensing the targeted molecule 1617 by forming multiple cross-linking bridges 1615 that are all bound to the same targeted DNA molecule. Labels 1615 indicate examples where 2 of the origami tails have hybridized to each other and as a consequence bring together sections of the genomic template molecule 1604 that would normally be separated by thousands or tens of thousands of bases. The hybridization temperature between origami tails 1613 is preferably chosen to be considerably lower than the hybridization and extension temperature used for the capture primers 1603. A typical hybridization and extension temperature for the capture primers is 64° C. or as the favorable temperature for hybridization of the origami tails is 20° C. or 30° C. (° C. means degrees Celsius). As a result the DNA target segment 1604 is transformed from a highly vulnerable and extended long molecule into a more compact form depicted by label 1617. Such condensed segments can be preferably created under dilute conditions to reduce the risk of any entanglement of off-target DNA molecules and are then much more robust for subsequent magnetic capture and handling so that long DNA lengths are preserved throughout the extraction and washing protocol. Label 1633 indicates the hybrid molecule consisting of extended capture primer 1603 and the attached origami tail 1613.

FIG. 16 at bottom, labeled 2, in accordance with one embodiment of the present invention depicts the use of separate origami oligo nucleotides that are used independently from the RSE capture primers. In this case the genomic template 1607 has specific target regions indicated by 1605 and 1606 that are used to design complimentary hybrid oligonucleotides that contain the respective complementary sequences 1608 and 1609. There are typically many of specific target sequences that ultimately located thousands of tens of thousands of bases apart from each other that I used to design the complementary origami oligonucleotides, and all of those are then used to pull together the targeted genomic template 1610 into a much more compact and looped structure through condensation with origami oligonucleotides 1611, resulting in a robust and compact structure depicted in 1612. For further details for enabling these embodiments of the invention see Rothemund (2006). The publication of Rothemund (2006) is incorporated herein in its entirety. For supplemental enablement details see methods published at .caltech.edu/DNApublications-Rothemund.html.

Figure 17:
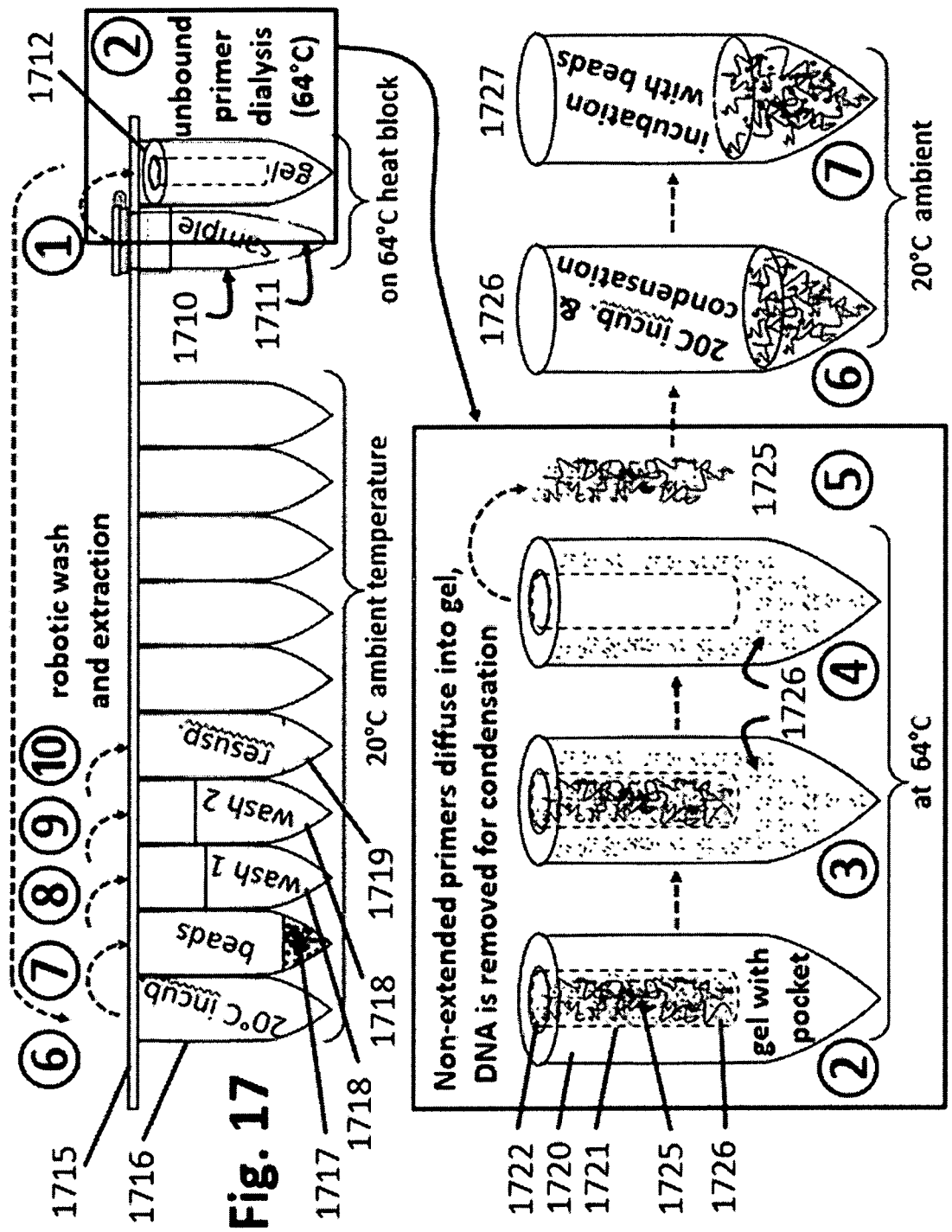
FIG. 17 in accordance with one embodiment of the present invention depicts a typical sample cartridge 1715 that contains various reagents for region-specific extraction. From the left, the container 1716 is used for the incubation of the target DNA with the magnetic beads, which are located in containers 1717. Containers 3 and 4 from the left contain the wash solution 1718, and container number 5 contains the resuspension solution 1719. Additional containers are available for additional process steps. On the right in container 1710 is the original DNA sample 1711 that gets incubated 4 region-specific extraction. In this case here the last container on the right 1712 contains an internal layer of a solid gel 1720 that is used to remove small molecules 1726 after the region-specific extraction reaction has been carried out. The process steps are indicated by the circled numbers 1 through 10. In Step 1, the sample 1711 after the completion of the region specific extraction reaction that adds biotin elated tags to selected regions of the genomic template DNA 1725 as mediated by the RSE capture primer extension is transferred to vessel 1712 that contains the gel lining 1720. In Steps 2 through 5, the extracted DNA template remains in the cylindrical sample container 1721 formed by the gel lining 1720 in container 1712 widely un-incorporated small reaction components such as unincorporated biotin tags 1722 and non-extended primers as well as small DNA fragments that are not desirable for capture diffuse into the gel lining as indicated by 1726 in process step 3. In Step number 4, the genomic DNA template 1725 is then removed from the pocket in the gel lined container, thereby leaving the free and small reaction components 1726 behind in the gel widely desirable long targeted DNA 1725 shown in blue as removed in process step number 5. In process step number 6, the temperature is then reduced from the initial temperature at which the previous process steps are carried out, which is typically 64° C. but which can be between 50° C. and 70° C., so that at the lower temperature of about 20° C. to 30° C. degrees the condensation of the DNA molecule with the condensation oligo nucleotides can take place as indicated in process step number 6. In process step 7 the tagged and condensed target DNA is then combined with the magnetic beads taken from container 1717 for magnetic extraction and washing 1727. Due to the condensation step and optional winding-up of the template DNA molecules on rotating beads the long targeted DNA molecules are considerably more robust and stable during the subsequent handling and washing steps, resulting in the ability to isolate very long template molecules from the target region with very high capture efficiency. One DNA target segment of about 4.8 Mb bases length is the major human histocompatibility complex (MHC), which is considered the most complex region of the human genome. The MHC is characterized by highly homologous, GC rich, repeat rich and polymorphic regions that are of high scientific and diagnostic importance. The MHC genome has eluded simple and accurate characterization for applications such as tissue typing, immunogenetics, immuno-oncology and disease and vaccine genetics. The human MHC is highly GC rich and therefore very difficult to reliably isolate and sequence with conventional methods. Both short fragment capture and amplification based methods have significant difficulty in dealing with the GC rich and complex regions when they contain unexpected types of genomic variation. Region-specific extraction using small DNA capture primers at only seven positions is able to isolate the entire region without the presence of any gaps, as indicated in panel three. In contrast, short fragment capture methods require about one order of magnitude more capture primers yet are not able to pull down the region without the presence of gaps when there are unexpected inserted sequences for GC which elements that are refractory for conventional capture. For example, in some embodiments of the present invention a target of DNA genomic template is sequenced directly after capture without requiring any intermediate amplification step. For example, in some embodiments of the present invention direct detection of methylated basis after enrichment through region-specific extraction, RSE, can be done. These reads may be generated by the actual genomic DNA target segments that is captured and by sequencing directly through a nanopore sequencing device. The captured genomic DNA target segments can be used without any amplification step in a library preparation process useful for Oxford Nanopore's MinIon™ device, for Pacific BioSciences platform, or for other long read sequencing platforms. The present invention can be adapted to be performed using a first Oxford Nanopore Voltrax™ fluid control base module. Magnets that are used in the Voltrax device can be used to concentrate streptavidin-labeled magnetic particles or other streptavidin-labeled structures bound to genomic DNA so as to safely permit removal of unwanted off-target material. The temperatures required for annealing of capture primers and subsequent enzymatic extension and biotin tagging can be carried out a using the Oxford Nanopore Voltrax™. An optical (fluorescent) quality control step to determine the concentration of DNA either before or after an optional amplification can be carried out. Inlet ports on the Oxford Nanopore 44 Voltrax™ can be used to provide different samples into a Voltrax™ cartridge to be used for RSE (region-specific extraction) for parallel processing in a microfluidic working area. A second Voltrax™ cartridge can contain an additional port and a microfluidic working area useful for a library preparation step before performing a next generation sequencing. A Voltrax™ base module can receive interchangeable cartridges in a sequential fashion so as to allow two different processes of RSE target capture and subsequent library preparation to be carried out sequentially. An initial DNA sample can be processed by RSE in the first cartridge and after completion of the region specific extraction RSE can then be transferred to the second cartridge for DNA amplification and library preparation, before being removed from the cartridge and transferred to the nanopore sequencing device.

FIG. 17 in accordance with one embodiment of the present invention depicts a typical sample cartridge 1715 that contains various reagents for region-specific extraction. From the left, the container 1716 is used for the incubation of the target DNA with the magnetic beads, which are located in containers 1717. Containers 3 and 4 from the left contain the wash solution 1718, and container number 5 contains the resuspension solution 1719. Additional containers are available for additional process steps. On the right in container 1710 is the original DNA sample 1711 that gets incubated 4 region-specific extraction. In this case here the last container on the right 1712 contains an internal layer of a solid gel 1720 that is used to remove small molecules 1726 after the region-specific extraction reaction has been carried out. The process steps are indicated by the circled numbers 1 through 10. In Step 1, the sample 1711 after the completion of the region specific extraction reaction that adds biotin elated tags to selected regions of the genomic template DNA 1725 as mediated by the RSE capture primer extension is transferred to vessel 1712 that contains the gel lining 1720. In Steps 2 through 5, the extracted DNA template remains in the cylindrical sample container 1721 formed by the gel lining 1720 in container 1712 widely un-incorporated small reaction components such as unincorporated biotin tags 1722 and non-extended primers as well as small DNA fragments that are not desirable for capture diffuse into the gel lining as indicated by 1726 in process step 3. In Step number 4, the genomic DNA template 1725 is then removed from the pocket in the gel lined container, thereby leaving the free and small reaction components 1726 behind in the gel widely desirable long targeted DNA 1725 shown in blue as removed in process step number 5. In process step number 6, the temperature is then reduced from the initial temperature at which the previous process steps are carried out, which is typically 64° C. but which can be between 50° C. and 70° C., so that at the lower temperature of about 20° C. to 30° C. degrees the condensation of the DNA molecule with the condensation oligo nucleotides can take place as indicated in process step number 6. In process step 7 the tagged and condensed target DNA is then combined with the magnetic bead s taken from container 1717 for magnetic extraction and washing 1727. Due to the condensation step and optional winding-up of the template DNA molecules on rotating beads the long targeted DNA molecules are considerably more robust and stable during the subsequent handling and washing steps, resulting in the ability to isolate very long template molecules from the target region with very high capture efficiency.

One DNA target segment of about 4.8 Mb bases length is the major human histocompatibility complex (MHC), which is considered the most complex region of the human genome. The MHC is characterized by highly homologous, GC rich, repeat rich and polymorphic regions that are of high scientific and diagnostic importance. The MHC genome has eluded simple and accurate characterization for applications such as tissue typing, immunogenetics, immuno-oncology and disease and vaccine genetics. The human MHC is highly GC rich and therefore very difficult to reliably isolate and sequence with conventional methods. Both short fragment capture and amplification based methods have significant difficulty in dealing with such GC rich and complex regions when they contain unexpected types of genomic variation. Region-specific extraction using small DNA capture primers at only seven positions is able to isolate the entire region without the presence of any gaps, as indicated in panel three. In contrast, short fragment capture methods require about one order of magnitude more capture primers yet are not able to pull down the region without the presence of gaps when there are unexpected inserted sequences for GC which elements that are refractory for conventional capture. For example, in some embodiments of the present invention a target of DNA genomic template is sequenced directly after capture without requiring any intermediate amplification step. For example, in some embodiments of the present invention direct detection of methylated basis after enrichment through region-specific extraction, RSE, can be done. These reads may be generated by the actual genomic DNA target segments that are captured and by sequencing directly through a nanopore sequencing device. The captured genomic DNA target segments can be used without any amplification step in a library preparation process useful for Oxford Nanopore's Minlon™ device, for Pacific BioSciences platform, or for other long read sequencing platforms. The present invention can be adapted to be performed using a first Oxford Nanopore Voltrax™ fluid control base module. Magnets that are used in the Voltrax device can be used to concentrate streptavidin-labeled magnetic particles or other streptavidin-labeled structures bound to genomic DNA so as to safely permit removal of unwanted off-target material. The temperatures required for annealing of capture primers and subsequent enzymatic extension and biotin tagging can be carried out a using the Oxford Nanopore Voltrax™. An optical (fluorescent) quality control step to determine the concentration of DNA either before or after an optional amplification can be carried out. Inlet ports on the Oxford Nanopore Voltrax™ can be used to provide different samples into a Voltrax™ cartridge to be used for RSE (region-specific extraction) for parallel processing in a microfluidic working area. A second Voltrax™ cartridge can contain an additional port and a microfluidic working area useful for a library preparation step before performing a next generation sequencing. A Voltrax™ base module can receive interchangeable cartridges in a sequential fashion so as to allow two different processes of RSE target capture and subsequent library preparation to be carried out sequentially. An initial DNA sample can be processed by RSE in the first cartridge and after completion of the region specific extraction RSE can then be transferred to the second cartridge for DNA amplification and library preparation, before being removed from the cartridge and transferred to the nanopore sequencing device.

The present invention includes methods of designing capture primers selected using oligonucleotides with modified bases, attachment chemistry molecules, linkers, spacers and Click chemistry. A good commercial source of the oligonucleotides with modified bases, attachment chemistry molecules, linkers, spacers and Click chemistry is Integrated DNA Technologies, Inc. 1710 Commercial Park, Coralville, Iowa 52241, USA.

A wide variety of modifications can be incorporated into an oligonucleotide at the time of synthesis. When possible, this is done using a modified solid support (CPG) for 3'-modifications or a specialized phosphoramidite reagent for internal and 5'-modifications. Certain modifications (notably Digoxigenin and some fluorescent dyes) are not available as a modified-CPG or phosphoramidite and must be attached to the oligo after synthesis using NHS Ester chemistry. NHS Esters react with free primary amines and result in stable, covalent attachment. A primary amine is therefore added to the oligo during synthesis to permit reaction with the desired NHS Ester. Catalog prices for NHS Ester modifications include the amino-modifier:

| | | |
|---|---|---|
| 5' | 5' Amino Modifier C6 | (phosphoramidite) |
| Int | Internal amino-C6-dT | (phosphoramidite) |
| 3' | 3' Amino Modifier | (CPG) |

Post-synthetic chemical modifications made to an oligonucleotide result in lower yields than modifications introduced during synthesis. Further, all NHS Ester modification require HPLC purification. PAGE purification is not offered for NHS Ester modifications as yields are further decreased and certain modifications can be damaged during PAGE purification Some embodiments of the present invention employ methods using binding and crosslinking of DNA stabilizing oligonucleotides for making DNA origami with RSE capture primers.

The invention includes embodiments which employ Click chemistry which is a two-step process that uses quantitative chemical reactions of alkyne and azide moieties to create covalent carbon-heteroatom bonds between biochemical species.

See idtdna.com/site/Catalog/Modifications/ClickChemistry/8

The reaction uses copper (I) as a catalyst and forms a 1,2,3-triazole between an azide and terminal alkyne. The technology is reliable and stable which makes it an ideal oligonucleotide labeling method. The benefits of click chemistry include: (1) click chemistry reactions can occur in aqueous solution at room temperature; (2) the click chemical products are stable toward $H_2O$, $O_2$, and most organic synthesis conditions; (3) the click chemistry produces no side chemical reactions; the click chemistry reaction rely on reliable catalytic processes; (4) there is a lack of functional group interference; (5) The click reactions are thermally and hydrolytically stable; and (6) click chemical reactions are selective, and suitable for covalent bond syntheses of biochemical.

| Modification Name | Used for modifying oligos with |
|---|---|
| 5', Int, 3' Azide (NHS Ester) | 5',3', or internal azide functional group |
| 5' Hexynyl | 5' alkyne functional group |
| 5', Int, 3'5-Octadiynyl dU | 5',3', or internal alkyne functional group |
| 5', Int Biotin (Azide) | 5' or internal biotin functional group |
| 5', Int 6-FAM (Azide) | 5' or internal 6-FAM functional group |
| 5', Int 5-TAMRA (Azide) | 5' or internal 5-TAMRA functional group |

See: https://www.idtdna.com/site/Catalog/Modifications/Category/7

A description of some modified nucleotide bases and their chemical structures are provided below. Some embodiments of the present invention use a modified nucleotide base. A modified nucleotide base is selected from the group consisting of a 5' Bromo dU, a 5' 2-Aminopurine, a 3' 2-Aminopurine, a 5' 2,6-Diaminopurine (2-Amino-dA), a 3' 2,6-Diaminopurine (2-Amino-dA), a 5' deoxyUridine, a 3' deoxyUridine, an Inverted DT, an Inverted Dideoxy-T, a Dideoxy-C, a 5-Methyl dC, a deoxyInosine, a Super T®, a Super G®, Locked Nucleic Acids (LNA's), a 5-Nitroindole, a 2'-O-Methyl RNA Bases, a Hydroxmethyl dC, an Iso-dG, an Iso-dC, a 5' Fluoro C, a 5' Fluoro U, a 5' Fluoro A, a 5' Fluoro G, a 5' 2-MethoxyEthoxy A, a 5' 2-MethoxyEthoxy MeC, a 5' 2-MethoxyEthoxy G, a 5' 2-MethoxyEthoxy T, a 3' Fluoro C, a 3' Fluoro U, a 3' Fluoro A, a 3' Fluoro G, a 3' 2-MethoxyEthoxy A, a 3' 2-MethoxyEthoxy MeC, a 3' 2-MethoxyEthoxy G, a 3' 2-MethoxyEthoxy T, and a combination thereof.

5-Bromo dU

The base 5-Bromo-deoxyuridine is a photo-reactive halogenated base that can be incorporated into oligonucleotides to crosslink them to DNA, RNA or protein with exposure to UV light. Crosslinking is maximally efficient with light at 308 nm.

Chemical structure for 5-Bromo dU is depicted below with 369 MW:

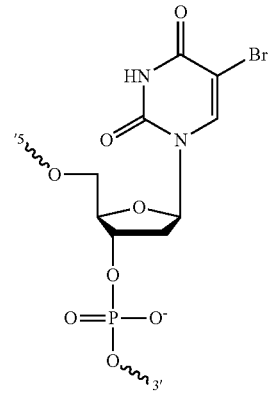

2-Aminopurine

The base 2-Aminopurine can substitute for dA in an oligonucleotide. It is a naturally fluorescent base that is sensitive to the local environment making it a useful probe for monitoring the structure and dynamics of DNA hairpins and for detecting the base stacking state of a duplex. 2-Aminopurine can be destabilizing and slightly lower the Tm.

(2) Below depicted is chemical structure for 5' 2-Aminopurine with 313 MW:

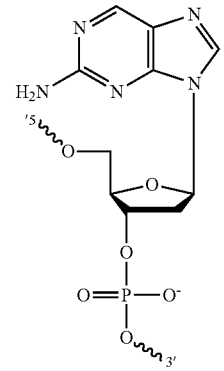

5'. 2,6-Diaminopurine (2-Amino-dA)

This modified base can form three hydrogen bonds when base-paired with dT and can increase the Tm of short oligos by as much as 1-2° C. per insertion. This effect, however, is complex and is dependent on sequence context.

(3) Below depicted is chemical structure for 5' 2,6-Diaminopurine (2-Amino-dA) which has 328 MW:

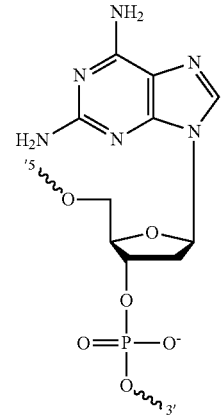

DeoxyUridine (dU)

This base can be substituted for dT in DNA oligonucleotides. The base can be removed by the enzyme uracil-N-deglycosylase (UNG) which renders the oligo susceptible to strand scission. One common use of this strategy is to eliminate amplified DNA and prevent cross-contamination.

(4) Below depicted is chemical structure for 5' deoxyUridine with 290 MW:

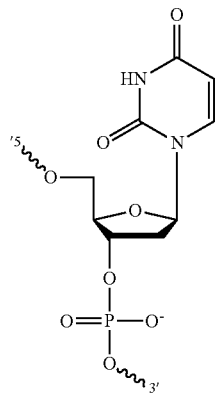

(5) Below depicted is chemical structure for 3' deoxyUridine with 290 MW:

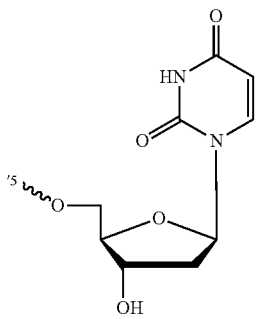

Dideocy-C, Dideoxycytidine (ddC) base is a 3' chain terminator that prevents 3' extension by DNA polymerases.

(6) Below depicted is chemical structure for 5' Dideoxy-C with 273 MW:

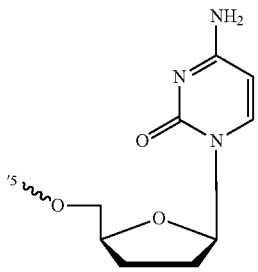

5-Methyl dC

5-Methyl deoxyCytidine when substituted for dC will increase the Tm by as much as 0.5° C. per insertion. In addition, the presence of 5-Methyl dC in CpG motifs can prevent or limit unwanted immune responses that otherwise occur if oligos are administered in vivo, which is of particular importance in antisense applications.

(7) Below depicted is chemical structure for 5' 5-Methyl dC with 303 MW:

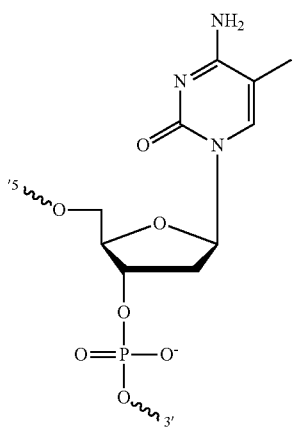

(8) Below depicted is chemical structure for 3' 5-Methyl dC with 303 MW:

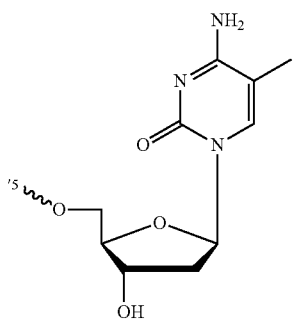

deoxyInosine

2'-deoxyInosine (dI). DeoxyInosine is a naturally occurring base that, while not truly universal, is less destabilizing than mismatches involving the four standard bases. Hydrogen bond interactions between dI and dA, dG, dC and dT are weak and unequal, with the result that some base-pairing bias does exist with dI:dC>dI:dA>dI:dG>dI:dT. When present in a DNA template, deoxyInosine preferentially directs incorporation of dC in the growing nascent strand by DNA polymerase.

(9) Below depicted is chemical structure for 5'deoxyInosine with 314 MW:

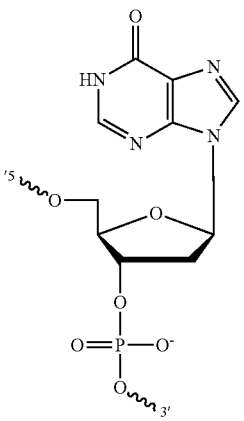

(10) Below depicted is chemical structure for 3'deoxylnosine with 314 MW:

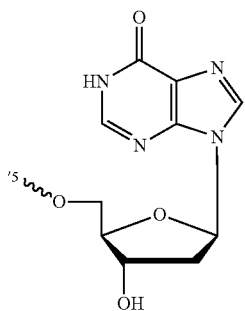

Inverted dT is a base that can be incorporated at the 3'-end of an oligo, leading to a 3'-3' linkage which inhibits both degradation by 3' exonucleases and extension by DNA polymerases.

(11) Below depicted is chemical structure for 3' Inverted dT with 304 MW:

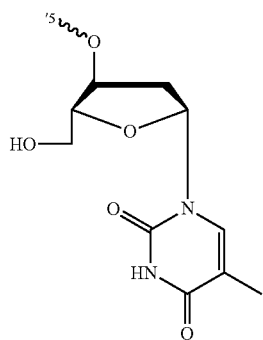

Inverted Dideoxy-T

Placing Inverted Dideoxy-T at the 5' end of a sequence will prevent unwanted 5' ligations.

(12) Below depicted is chemical structure for 5' Inverted DideoxyT with 288 MW:

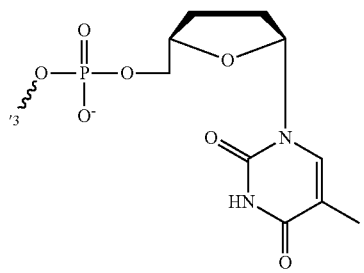

Super T®

Super T (5-hydroxybutynl-2'-deoxyuridine) is a duplex-stabilizing modified base that increases oligonucleotide Tm. Oligonucleotides containing Super T can be extended normally by polymerases, including Taq polymerase, making Super T a useful modified base for designing short primers or probes for low-complexity, A-T rich sequences. (5)

(13) Below depicted is chemical structure for 5' Super T® with 358 MW:

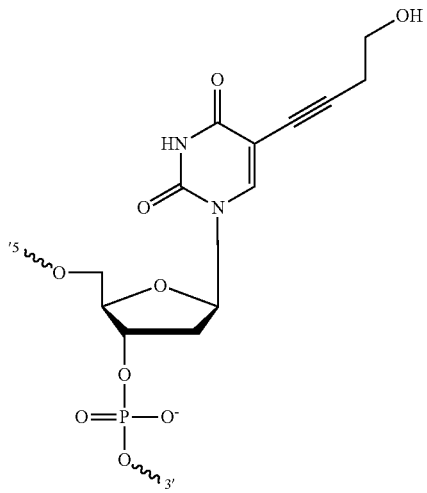

(14) Below depicted is chemical structure for 3' Super T® with 358 MW:

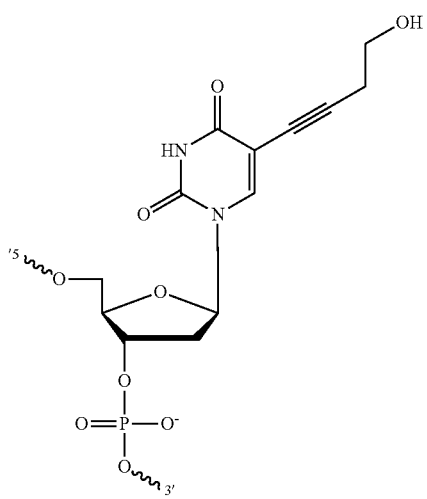

Super G®

Super G (8-aza-7-deazaguanosine) is a modified base that eliminates naturally occurring, non-Watson-and-Crick secondary structures associated with guanine-rich sequences. Oligonucleotides containing Super G can be extended normally by polymerases, including Taq polymerase, making Super G a useful modified base for designing guanine-rich primers and probes. In addition, unlike standard guanine bases, Super G does not quench fluorophores, potentially improving probe performance

(15) Below depicted is chemical structure for 5' Super G® with 329 MW:

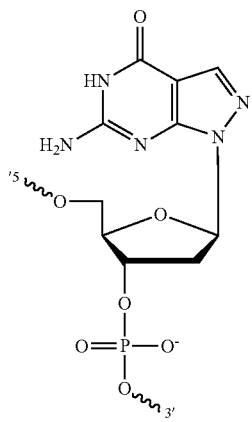

(16) Below depicted is chemical structure for 3' Super G® with 329 MW:

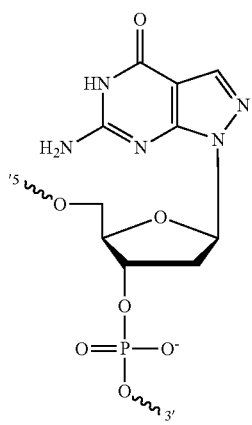

(17) Below depicted is chemical structure for 5' 5-Nitroindole with 540 MW:

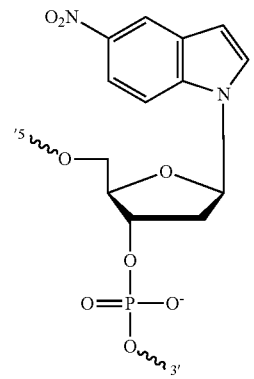

(18) Below depicted is chemical structure for 3' 5-Nitroindole with 540 MW:

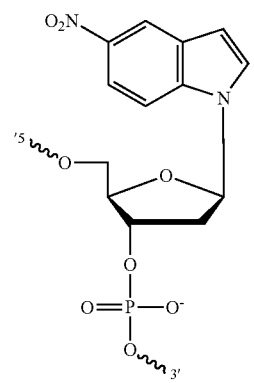

Locked Nucleic Acids (LNA's)

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. The number of LNAs incorporated into a single oligo should therefore be 10 bases or less.

5-Nitroindole

5-Nitroindole is a universal base available that does not favor any particular base-pairing (i.e., it does not support base-specific hydrogen bond formation), but does contribute to duplex stability through base-stacking interactions. Therefore, it is not as destabilizing to the duplex as mismatches between the standard bases. 5-Nitroindole directs random incorporation of any specific base when used as a template for DNA polymerase and partially blocks enzyme processivity.

2'-O-Methyl RNA Bases

2'-O-Methyl RNA is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message. To include a 2' O-methyl modification in your RNA sequence, simply place a lowercase "m" in front of the base; for example, mAmGmCmU.

Hydroxmethyl dC

Hydroxmethyl dC is a recently discovered modified base with a probable epigenetic role.

(19) Below depicted is chemical structure for 5' Hydromethyl C with 319 MW:

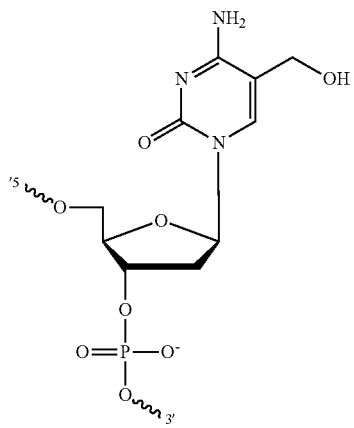

(20) Below depicted is chemical structure for 3' Hydroxy Methyl C with 319 MW:

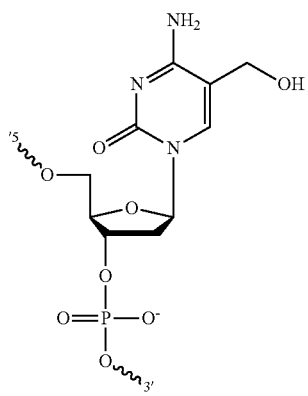

Iso-dC and Iso-dG are chemical variants of cytosine and guanine, respectively. Iso-dC will hydrogen bond with Iso-dG but not with dG. Similarly, Iso-dG will base pair with Iso-dC but not with dC. Incorporation of these bases into DNA effectively expands the genetic alphabet and permits synthesis of oligonucleotides that have increased specificity and decreased mismatch hybridization potential. For example, an oligonucleotide containing Iso-dC can be designed so that it will hybridize to a complementary oligo containing Iso-dG but will not hybridize to any naturally occurring nucleic acids sequence. Oligonucleotides that contain either or both iso-bases require IE-HPLC purification.

(21) Below depicted is chemical structure for 5' Iso-dC with 303 MW:

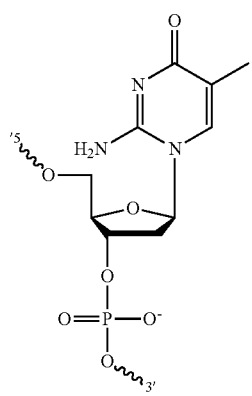

(22) Below depicted is chemical structure for 5' Iso-dG with 329 MW:

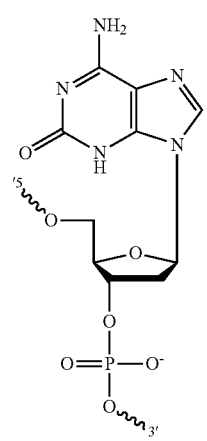

Fluoro Base:

2' Fluoro bases have a fluorine modified ribose which increases binding affinity (Tm) and also confers some relative nuclease resistance when compared to native RNA. These modifications are commonly employed in ribozymes and siRNAs to improve stability in serum or other biological fluids.

Fluoro C

(23) Below depicted is chemical structure for 5' Fluoro C with 307 MW:

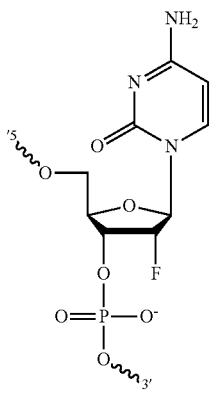

(24) Below depicted is chemical structure for 3' Fluoro C with 307 MW:

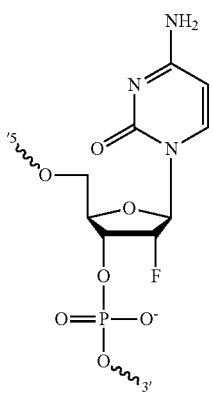

Fluoro U

(25) Below depicted is chemical structure for 5' Fluor U with 308 MW:

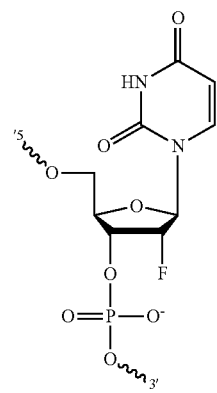

(26) Below depicted is chemical structure for 3' Fluor U with 308 MW:

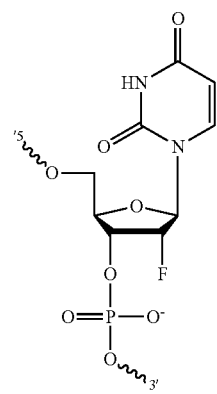

Fluoro A

(27) Below depicted is chemical structure for 5' Fluoro A with 331 MW:

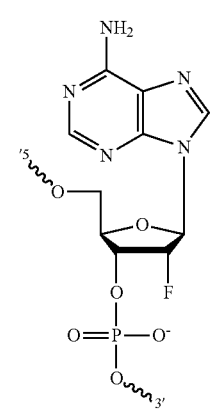

(28) Below depicted is chemical structure for 3' Fluoro A with 331 MW:

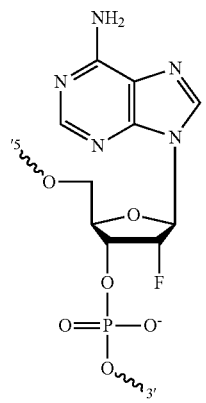

Fluoro G

(29) Below depicted is chemical structure for 5' Fluoro G with 347 MW:

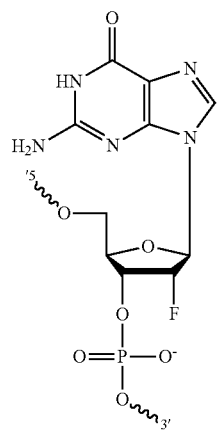

(30) Below depicted is chemical structure for 3' Fluoro G with 347 MW:

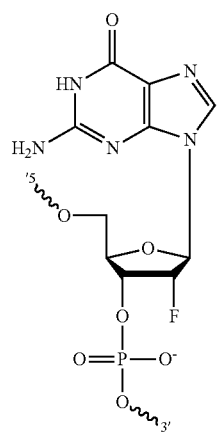

2'-O-Methoxy-Ethyl Bases (2'-MOE)

2'-MOE bases are often used for antisense oligos (ASO), aptamers, and siRNA. Compared to standard RNA bases 2'-MOE bases offer increased resistance to nuclease degradation, reduced toxicity, and increased affinity for binding to complimentary RNA.

For IDT antisense technical bulletin see idtdna.com/pages/education/decoded/article/antisense-oligonucleotides-(asos).

The chemical structures for the 2'(MOE) bases: 5' 2-MethoxyEthoxy A, 5' 2-MethoxyEthoxy MeC, 5' 2-MethoxyEthoxy G, 5' 2-MethoxyEthoxy T, 3' 2-Methoxy-Ethoxy A, 3' 2-MethoxyEthoxy MeC, 3' 2-MethoxyEthoxy G, and 3' 2-MethoxyEthoxy T are not provide by their manufacturer who is Integrated DNA Technologies, Skokie, Ill., USA.

A description of some nucleotide linkers and their chemical structures is provided below. For some embodiments of the present invention, a nucleotide linker may be selected from the group consisting of Acrydite™, Adenylation, Azide (NHS Ester), Digoxigenin (NHS Ester), Cholesterol-TEG, I-Linker™, biotin, streptavidin, and any combination thereof.

Acrydite™ is an attachment chemistry based on an acrylic phosphoramidite that can be added to oligonucleotides as a 5'-modification. Acrydite-modified oligonucleotides covalently react with thiol-modified surfaces or can be incorporated into polyacrylamide gels during polymerization.

(31) Below is the chemical structure of 5' Acrydite™ with 247 MW:

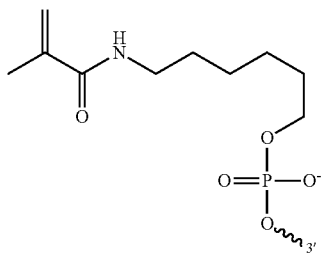

Adenylation—T4 RNA Ligase uses ATP to adenylate the 5'-end of a single-strand nucleic acid sequence. This activated adenylated-oligo is then covalently connected (ligated) to the 3'-OH of a second single-stranded sequence. Adenylated oligonucleotides containing a pyrophosphate linkage are substrates for T4 RNA Ligase in the absence of ATP (1). IDT will custom adenylate an oligonucleotide for use with RNA-Ligase using the chemical adenylation method of Unrau and Bartel (2). T4 RNA Ligase will use an adenylated DNA linker with similar efficiency as an adenylated RNA linker and IDT recommends use of adenylated DNA oligos for this application. Note that IDT requires blocking the 3'-end of an adenylated oligo so it cannot circularize; use of either 3'-Spacer C3/3SpC3/or dideoxycytosine/3ddC/is preferred. References 1. England, T. E., Gumport, R. I. and Uhlenbeck, O. C. (1977) Dinucleoside pyrophosphate are substrates for T4-induced RNA ligase. Proc Natl Acad Sci USA, 74, 4839-4842. 2. Unrau, P. J. and Bartel, D. P. (1998) RNA-catalysed nucleotide synthesis. Nature, 395, 260-263.

(32) Below is the chemical structure of 5' Adenylation with 410 MW:

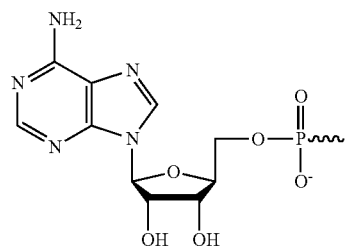

Azide (NHS Ester)—IDT's Azide modification uses an NHS Ester functional group to attach an azide moiety at the 5', 3' or any internal position in an oligo. This azide moiety may subsequently be used to attach alkyne modified groups through the click reaction. The internal version of this modification is attached to the oligo through a dT base. Incorporation of the internal version will add a dT nucleotide at that position. To avoid adding an extra nucleotide, replace an existing T nucleotide in your sequence with the required modification.

(33) Below is the chemical structure of 5' Azide (NHS Ester) with 318 MW:

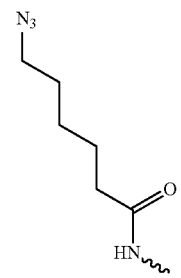

Digoxigenin (NHS Ester)—Digoxigenin is a small hapten that can be conjugated to amino-modified oligos. Anti-digoxigenin antibodies allow capture or detection of a digoxigenin-labeled oligo and can be used in a variety of assay formats much like biotin/streptavidin.

(34) Below is the chemical structure of 5' Digoxigenin (NHS Ester) with 723 MW:

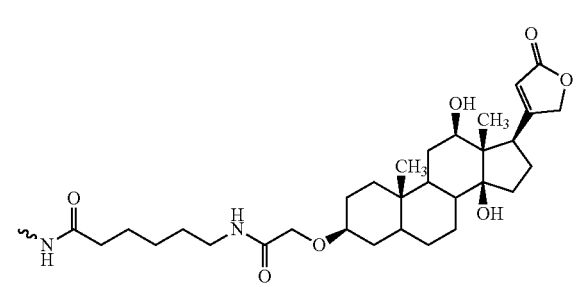

Cholesterol-TEG—Cholesterol can be conjugated to oligonucleotides and can facilitate uptake into cells. It has been used as a transfection aid for antisense oligos and siRNAs, both in vitro and in vivo. Cholesterol is a very hydrophobic modification that is best purified using RP-HPLC.

(35) Below is the chemical structure of 3' Cholesterol-TEG with 756 MW:

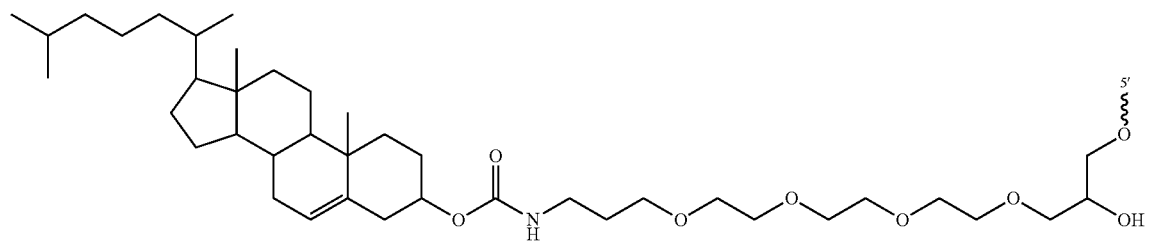

For some embodiments of the present invention, a primary amino group can be used to attach a variety of modifiers (such as fluorescent dyes) to an oligonucleotide or used to attach an oligonucleotide to a solid surface. Amino modifiers can be positioned at the 5'-end with either a standard (C6) or longer (C12) spacer arm. Amino modifications can be positioned at the 3'-end. Internal amino modifications can be introduced using an amino-dT base. Sold by Integrated DNA Technologies, Skokie, Ill., USA are a variety of amino linkers.

The amino linker may be selected from the group consisting of a C6 linker, a C12 linker, a 5' Amino Modifier C6 dT linker, a 3' Amino Modifier C6 dT linker, a 3' Amino Modifier C6 dT linker, a 3' Amino Modifier linker, a 5' Uni-Link™ Amino Modifier linker, a 5' Hexenyl linker, a 5-Octadiynyl dU linker, a 3' 5-Octadiynyl dU linker, a 5' Biotin linker, a 3' Biotin linker, a 5' Biotin (Azide) linker, a 5' Biotin dT linker, a 3' Biotin dT linker, a 3' Biotin TEG with extended spacer arm linker, a 5' Biotin TEG with extended spacer arm linker, a 5' Dual Biotin linker, a 5' PC Biotin, a 5' Desthiobiotin TEG linker, 3' Desthiobiotin TEG linker, a Thiol C3 S-S linker, a Dithiol linker, a Thiol Modifier C6 S-S linker, and any combination thereof.

The molecular structure of these linkers is depicted below with their molecular weights according to Integrated DNA Technologies, Skokie, Ill., USA who provides the chemical structures of these linkers.at idtdna.com/site/Catalog/Modifications/Category/2.

(36) Below is the chemical structure of the 179 MW (MW means molecular weight) C6 primary amine linker:

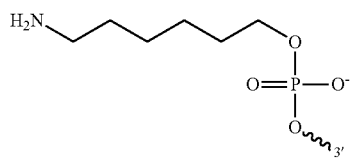

(37) Below is the chemical structure of the 263 MW C12 primary amine linker:

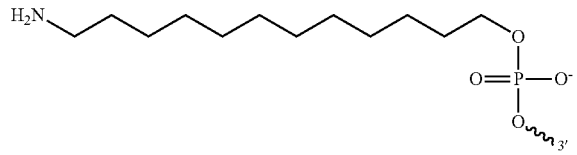

(38) Below is the chemical structure of the 458 MW 5' Amino Modifier C6 dT linker:

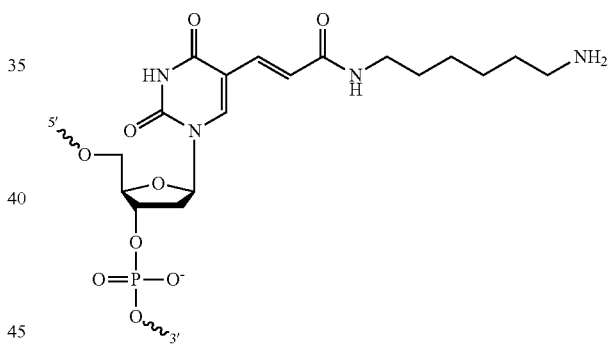

(39) Below is the chemical structure of the 458 MW 3' Amino Modifier C6 dT linker:

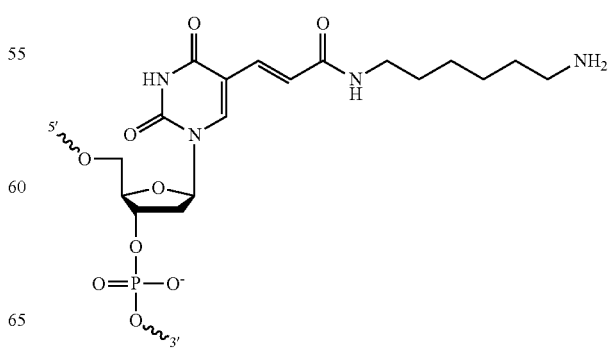

(40) Below is the chemical structure of the 211 MW 3' Amino Modifier linker:

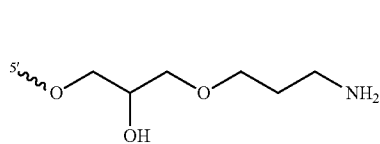

(41) Below is the chemical structure of the 209 MW 5' Uni-Link™ Amino Modifier linker:

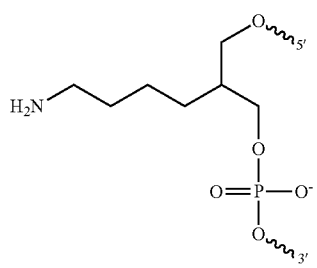

(42) Below is the chemical structure of the 160 MW 5' Hexenyl linker:

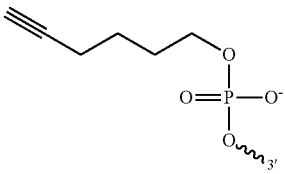

(43) Below is the chemical structure of the 394 MW 5-Octadiynyl dU linker:

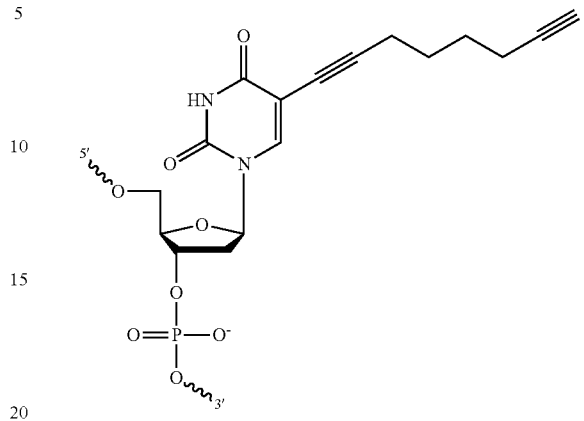

(44) Below is the chemical structure of the 394 MW 3' 5-Octadiynyl dU linker:

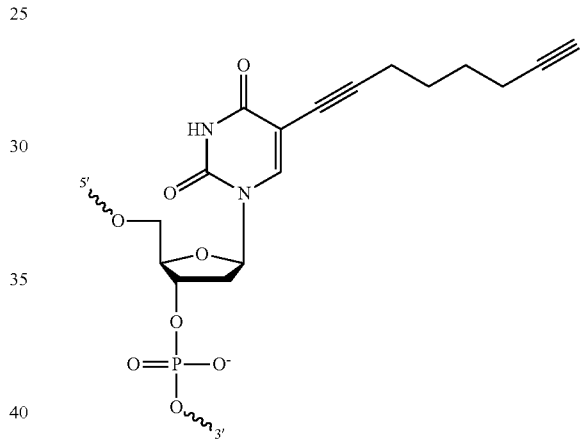

(45) Below is the chemical structure of the 393 MW 5' Biotin linker:

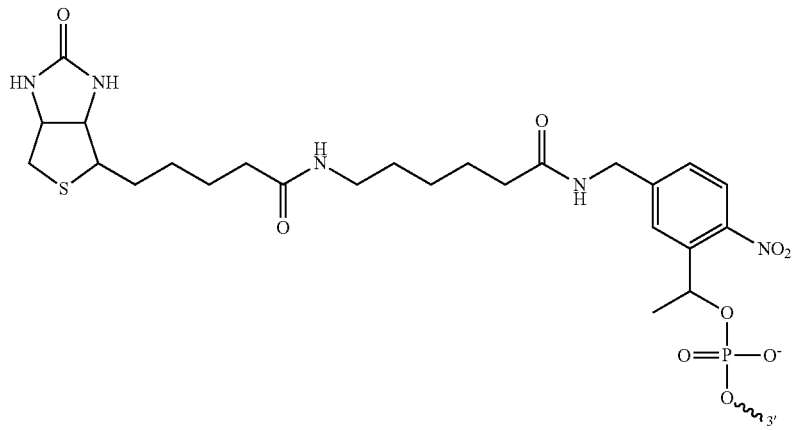

(46) Below is the chemical structure of the 685 MW 3' Biotin linker:
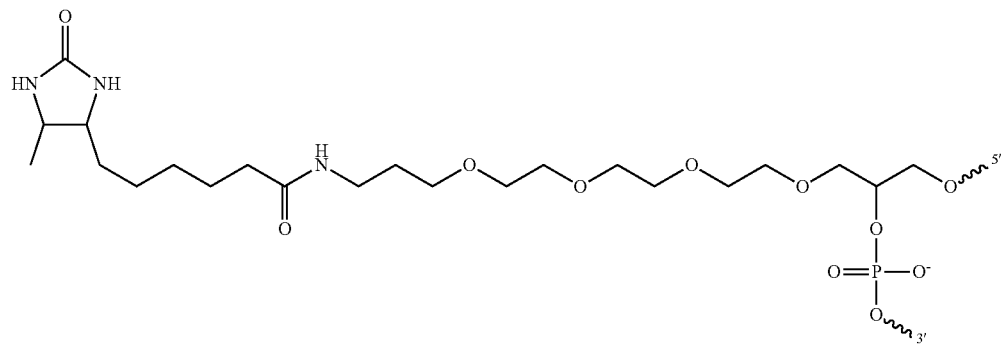
(47) Below is the chemical structure of the 487 MW 5' Biotin (Azide) linker:
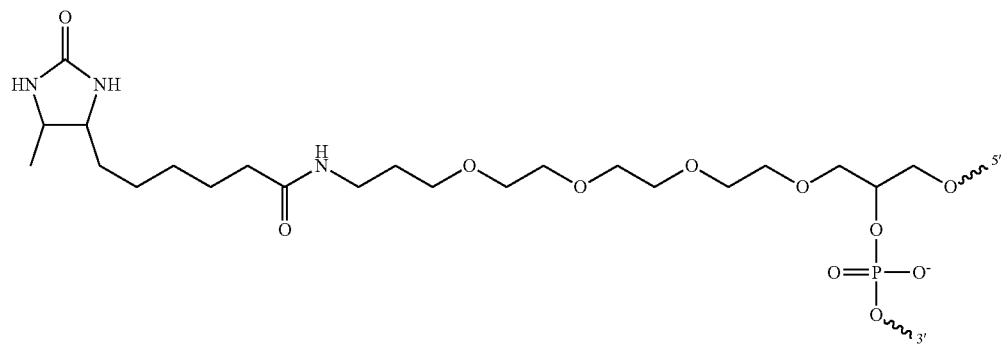
(48) Below is the chemical structure of the 685 MW 5' Biotin dT linker:
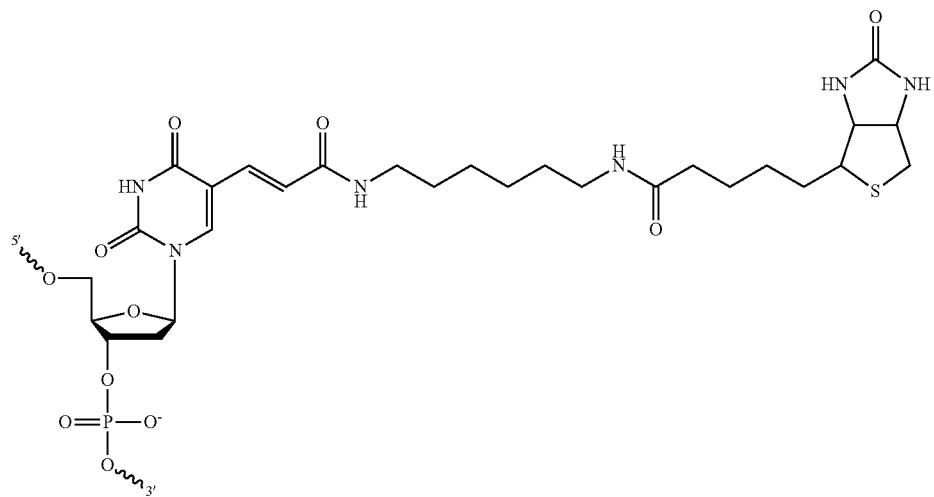

(49) Below is the chemical structure of the 685 MW 3' Biotin dT linker:
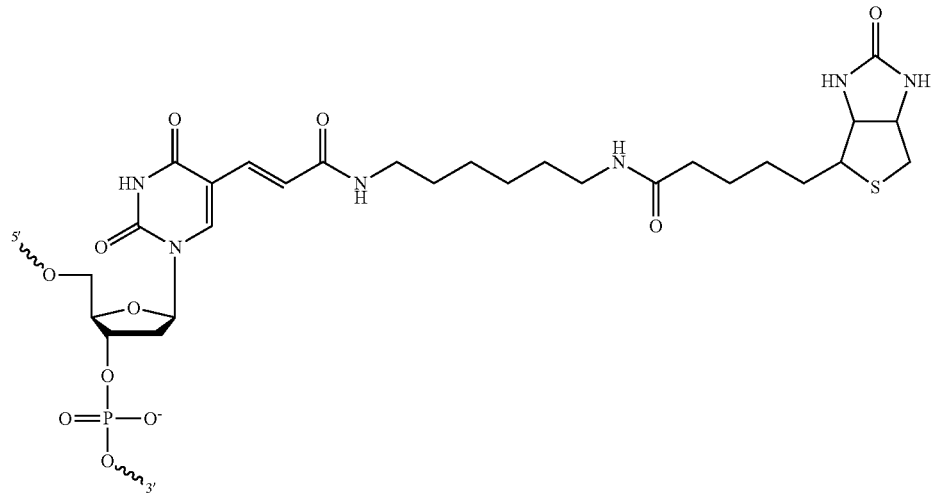
(50) Below is the chemical structure of the 482 MW 5' Biotin TEG with extended spacer arm linker:
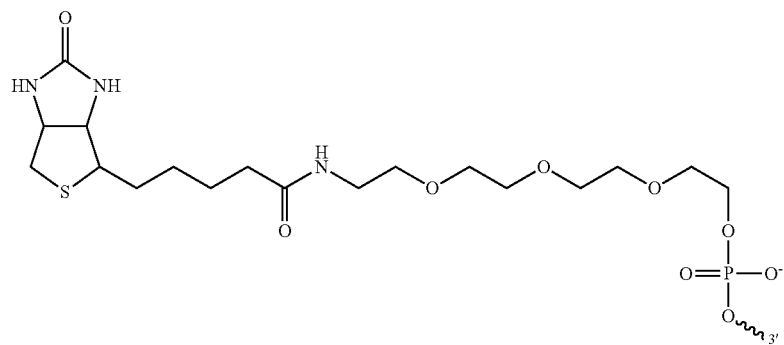
(51) Below is the chemical structure of the 570 MW 3' Biotin TEG with extended spacer arm linker:
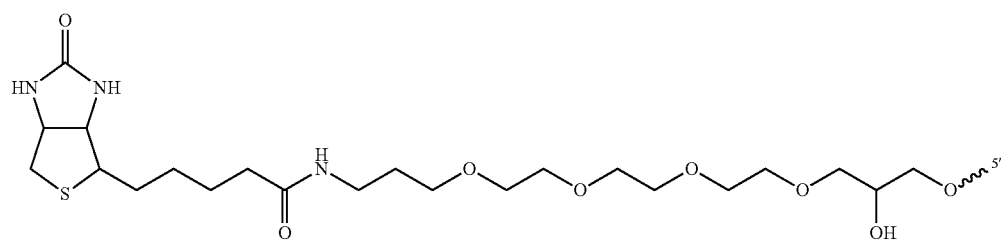

(52) Below is the chemical structure of the 871 MW 5' Dual Biotin linker:
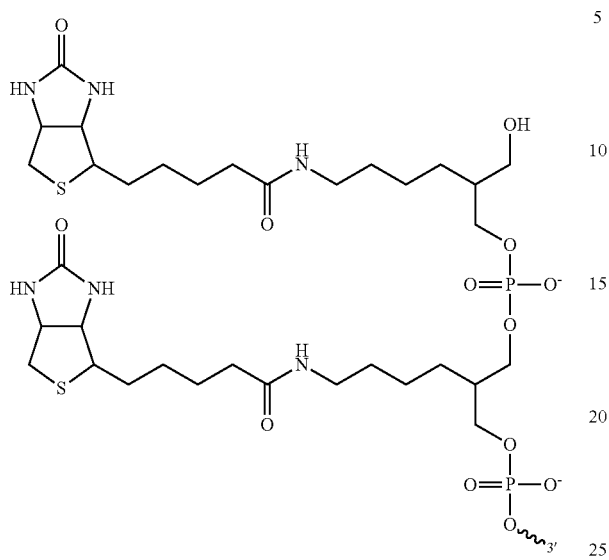
(53) Below is the chemical structure of the 598 MW 5' PC Biotin linker:
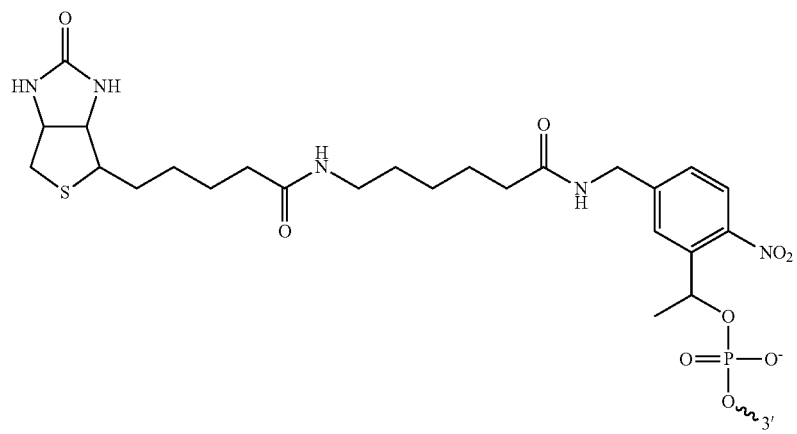
(54) Below is the chemical structure of the 540 MW 5' Desthiobiotin TEG linker:
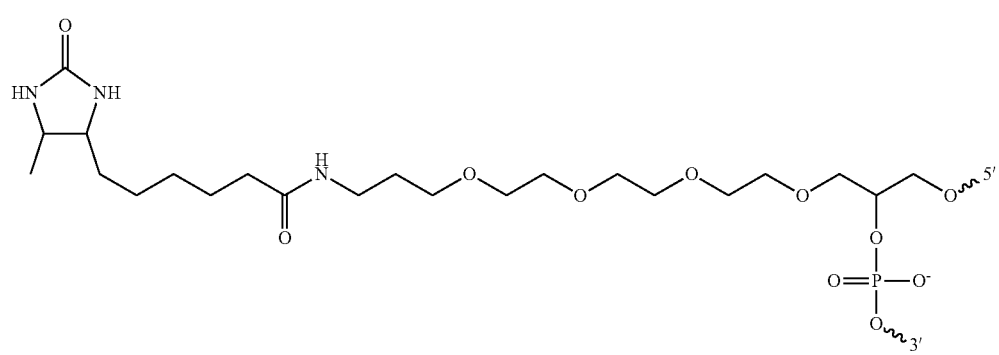

(55) Below is the chemical structure of the 540 MW 3' Desthiobiotin TEG linker:

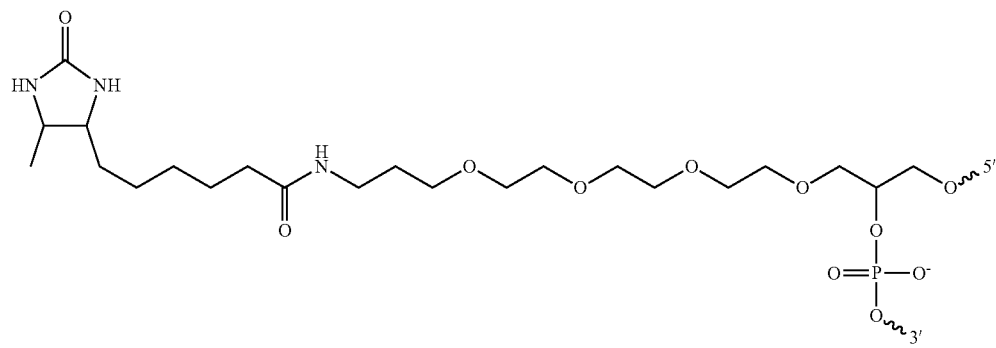

(56) Below is the chemical structure of the 244 MW 3' Thiol Modifier C3 S-S linker:

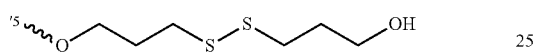

(57) Below is the chemical structure of the 214 MW 3' Dithiol linker:

Structure was not provided by Integrated DNA Technologies, Skokie, Ill., USA

(58) Below is the chemical structure of the 214 MW 5' Dithiol linker:

Structure was not provided by Integrated DNA Technologies, Skokie, Ill., USA.

(59) Below is the chemical structure of the 540 MW Thiol Modifier C6 S-S linker:

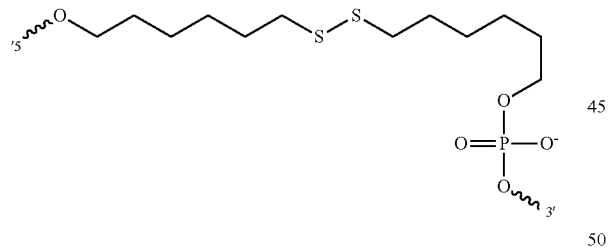

A description of some spacers for use in oligonucleotide synthesis and their chemical structures is provided below.

A Spacer for use in an embodiment of the present invention may be selected from the group consisting of a 5'C3 Spacer, a 3' C3 Spacer, a 5' PCSpacer, a 3' Hexanediol Spacer, a 5' Spacer 9, a 3' Spacer 9, a 5' Spacer 18, a 3' Spacer 18, a 5' 1',2'-Dideooxyribose (dSpacer), a 3' 1',2'-Dideooxyribose (dSpacer), and any combination thereof.

C3 Spacer

The C3 Spacer phosphoramidite can be incorporated internally or at the 5'-end of the oligo. Multiple C3 spacers can be added at either end of an oligo to introduce a long hydrophilic spacer arm for the attachment of fluorophores or other pendent groups.

(60) Below is the chemical structure of the 5' C3 Spacer with 138 MW:

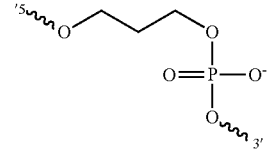

(61) Below is the chemical structure of the 3' C3 Spacer:

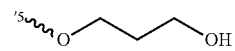

5' PC Spacer

PC (Photo-Cleavable) Spacer can be placed between DNA bases or between the oligo and a 5'-modifier group. It offers a 10-atom spacer arm which can be cleaved with exposure to UV light in the 300-350 nm spectral range. Cleavage releases the oligo with a 5'-phosphate group.

(62) Below is the chemical structure of 5' PC Spacer with 344 MW:

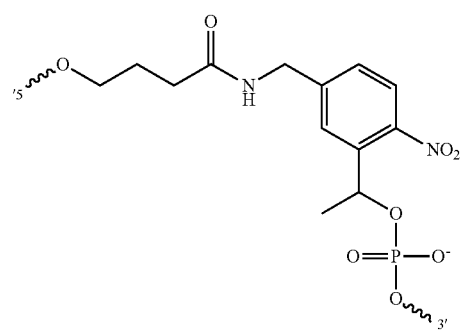

3' Hexanediol

Hexanediol is a six carbon glycol spacer that is capable of blocking extension by DNA polymerases. This 3' modification is capable of supporting synthesis of longer oligos.

(63) Below is the chemical structure of 3' Hexanediol with 180 MW:

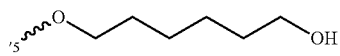

Spacer 9

Spacer 9 is a triethylene glycol spacer that can be incorporated at the 5'-end or 3'-end of an oligo or internally. Multiple insertions can be used to create long spacer arms.

(64) Below is the chemical structure of 5' Spacer 9 with 212 MW:

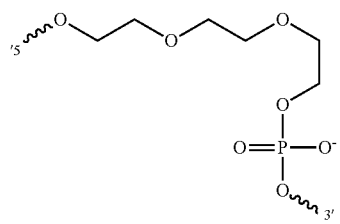

Spacer 18

Spacer 18 is an 18-atom hexa-ethyleneglycol spacer. It is the longest spacer arm that can be added as a single modification.

(65) Below is the chemical structure of 5' Spacer 18 with 344 MW:

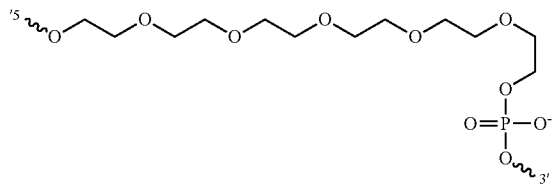

1',2'-Dideoxyribose (dSpacer)

The 1',2'-Dideoxyribose modification is used to introduce a stable abasic site within an oligonucleotide.

(66) Below is the chemical structure of 5'1',2'-Dideoxyribose (dSpacer) with 180 MW:

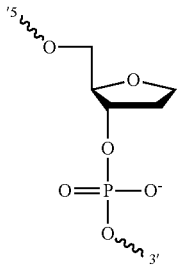

DdNTP or ddNTP refers to di-deoxynucleotides triphosphates. Di-deoxynucleotides may be selected from the group consisting of ddATP (di-deoxyadenine nucleotide triphosphate), ddTTP (di-deoxythymidine nucleotide triphosphate), ddCTP (di-deoxycytosine nucleotide triphosphate), and ddGTP. (di-deoxyguanosine nucleotide triphosphate).

The present invention includes embodiments which include rotational magnetic mixing. Rotational magnetic mixing can be used for spooling up very long DNA, with or without origami tails, 3-5 kb typical primer spacing.

Given that 10 kb of DNA has a length of 3.4 um, and a typical magnetic bead diameter is about 1 um, then the invention method only needs to use a relatively low concentration of magnetic beads when spooling and can have more than one primer and extended region binding to the same magnetic bead. Larger beads that do not settle very fast are advantageous. For the present invention DNA spooling onto one bead is a means for avoiding DNA shearing. Individual magnetic beads in homogeneous magnetic field can be rotated when the homogenous magnetic field rotates in a circle around a center tube having the magnetic beads in a small chamber. The formation of clusters of streptavidin-labeled magnetic beads or other streptavidin-labeled structures may be useful. Crosslinking may be useful. Notably the present invention utilizes the surprising observation that multiple biotin patches on long stretch of DNA are synergistic, not just additive in facilitating the stability and length of the DNA extension process as well as preventing DNA shearing. If nonmagnetic beads are used in the present invention, then similar effects to spooling may be achieved by centrifugation or spinning.

Some embodiments of the present invention use Cot-1 DNA in invention process of extracting DNA. Cot-1 DNA can also be used in comparative genomic hybridization. Cot-1 DNA® blocking reagent is DNA which is predominantly 50 to 300 bp in size, and enriched for repetitive DNA sequences. Cot-1 DNA® blocking reagent is commonly used to block nonspecific hybridization in aCGH microarray experiments and FISH assays. Cot-1 DNA® blocking reagent blocks repetitive sequences such as SINEs (short interspersed elements), LINEs (long interspersed elements), and sequence homology among members of the same gene family when added to the hybridization solution. Human Cot DNA is enriched for repetitive, non-coding elements commonly found in genomic DNA. These repetitive sequences often lead to non-specific binding during hybridization reactions. Adding Cot DNA to these reactions reduces non-specific binding associated with these repetitive sequences to improve accuracy. The use of Cot-1 DNA in fluorescence in situ hybridization (FISH) experiments. FISH experiments involve the hybridization of a labeled DNA probe of interest to a metaphase chromosome spread, which allows researchers to pinpoint the location along the length of a chromosome where the probe binds. Generally, the labeled probe is designed to hybridize to a gene of interest and FISH experiments can be used to detect gene deletion, duplication, and translocation events. In some cases, FISH probes are complex and consist of a long stretch of labeled DNA, which allows researchers to color-code a large region of, or an entire, chromosome. Cot-1 DNA is used in FISH experiments. By definition, Cot-1 DNA is genomic DNA that is highly enriched for repetitive elements, such as SINES (short interspersed repetitive elements, or Alu repeats) and LINES (long interspersed repetitive elements, or L1 elements). Cot-1 DNA used as an unlabeled blocking agent in FISH and other types of hybridization experiments (e.g., microarray experiments, comparative genome hybridization [CGH] experiments). It hybridizes to repetitive elements in the genome; as a result, Cot-1 DNA effectively prevents the non-specific binding of a labeled probe of interest to the repetitive DNA sequences. This is particularly important when the labeled probe of interest contains some repetitive elements. Cot-1 DNA is commercially available and typically derived from total genomic DNA of a given organism using procedures that enrich for repetitive sequence elements—its precise composition is not usually known. Although Cot-1 DNA has been used widely as a blocking agent in FISH experiments, it might not always be effective so to increase the specificity and reproducibility of hybridization experiments, synthetic repetitive DNA elements can be used as blocking agents and in contrast to Cot-1 DNA, their precise composition is known. A labeled probe of interest can be designed to lack repetitive elements in an effort to decrease non-specific binding.

Sources of DNA that can be sequenced include circulating tumors cells (CTCs), sputum, saliva, bacteria, blood, plants, urine, feces, cerebrospinal fluid, forensics, finger prints, hair, skin, and sperm. The practice of the invention is an enhanced method of non-invasive diagnostics. The invention can be practiced using archived DNA and methylated genomic DNA, and compared to what is learned by whole genome analyzed DNA. To practice the present invention embodiments a very small amount of DNA is needed as a sample to ensure an efficient isolation of the targeted area. The amount of DNA needed may be between about 600 ng to about 6 µg per extraction and the preferably the DNA concentration is at least 50 ng/µl.

In practicing embodiments of the present invention embodiments the invention includes preferred DNA handling methods. Useful DNA isolations methods include column- or bead-based methods that provide 'high quality' DNA— i.e. clean, reasonably long for the intended downstream application so as to prevent DNA damage in the form of DNA getting entangled or nicked. It is not necessary to shear the isolated DNA prior to use in RSE, however if desired this can be done in order to limit the linkage distance of each capture primer. Typical commercial methods for DNA extraction from blood, tissue, cell lines etc. work well and are able to produce captured fragment lengths after RSE that are significantly greater than those obtained with other enrichment methods. If the maximum available linkage distance is desired from any single capture point during RSE/HSE (haplotype-specific extraction), use freshly prepared DNA from freshly collected biospecimens that were properly stored and handled to avoid DNA degradation. Genomic DNA that is freshly isolated from older specimens, in particular if from blood, often suffers from significant damage and degradation that affects the achievable linkage distance and on-vs. off-target ratio during RSE. The presence of hemoglobin-based iron as well as other factors gradually damage and degrade nucleic acids in biospecimens even if they are kept frozen at −20C or −80C and stored in common collection buffers. In order to preserve the longest molecular weight DNA that is available from a biospecimen for later extraction, the sample should be stored at liquid nitrogen temperatures soon after collection. This turns the sample into a glassy state that prevents any molecular reactions. DNA that has been extracted from blood, tissue, cell lines etc. should be kept in solution or frozen at all times to avoid precipitation and entanglement, which increases off-target background. Ethanol precipitation methods are acceptable as long as the isolated DNA is never allowed to fully dry out. The use of reconstituted DNA that was previously dried or lyophilized is not recommended. Some exceptions apply for forensic applications where you obviously have no choice. If desired, the genomic DNA can be subjected to a defined restriction enzyme digest prior to RSE in order to create defined sequence boundaries, limit the overall linkage distance and thereby eliminate off-target material from more distant loci. It is also possible to carry out a size-selection step prior to RSE such as through the use of AMPure® beads to further eliminate any undesirable DNA template that does not correspond to the intended target size Some Embodiments Are Using Other Shapes Of Streptavidin-Labeled Structures Some embodiments of the invention comprise a biotinylated nucleotide of a primer extension product which can be bound to a streptavidin-labeled structure. In some embodiments the streptavidin-labeled structure is for binding to a biotin-labeled nucleotide, the streptavidin-labeled structure is selected from the group consisting of: a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, a streptavidin-labeled cluster, and any combination thereof, wherein the streptavidin-labeled cluster may be comprised a plurality of individual streptavidin-labeled structures selected from the group consisting of a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, and any combination thereof.

A primer extension product is defined as a polynucleotide product resulting from the enzymatic extension of a polynucleotide 3'-end with a nucleotide. In some embodiments of the invention the nucleotide is a biotinylated nucleotide or a nucleotide with another hapten that can bind specifically to its cognate ligand. The polynucleotide 3'-end can be part of an oligonucleotide primer hybridized to a polynucleotide template sequence that is entirely or partially complementary to the primer. The polynucleotide 3'-end can also be part of a double-stranded region of the polynucleotide that is enzymatically extended. A 5'-end overhang of the opposite strand acts as the template for primer extension.

A streptavidin-labeled structure is defined as a structure having one or more streptavidin attached to its surface through a link, which may be selected from the group consisting of: a chemical bond, which is covalent, non-covalent, ionic, hydrogen-bonding, coordination complex, van der Waals complex, hydrophilic, hydrophobic, and a combination thereof. The streptavidin-labeled structure has a largest dimension in nanometers selected from the group consisting of 10 to 100, 100 to 250, 200 to 500, 500 to 750, 700 to 900, 900 to 1200, 1000 to 3000, 2500 to 5000, 5000 to 10,000 and any combination thereof. In addition, some of the streptavidin-labeled structures can have a largest dimension in micrometers selected from the group consisting of 10 to 100, 100 to 250, 200 to 500, 500 to 750, 700 to 900, 900 to 1200, 1000 to 3000, 2500 to 5000, 5000 to 10,000 and any combination thereof.

As depicted in FIG. 16, an origami tail 1613 refers to a DNA origami tail. DNA origami is the nanoscale folding of DNA to create non-arbitrary two- and three-dimensional shapes at the nanoscale. Origami tails can be used to bring together relatively distant DNA target segments of single stranded portions of DNA or other polynucleotides by a condensation process to form loops and other structures, which process and resulting structure stabilizes the polynucleotide strand and thereby helps prevent physical and chemical damage to the polynucleotide. One advantage is that during an extraction, a manipulation, a region-specific capture and a library preparation for sequencing, the risk of shearing and fragmentation will have been reduced when a DNA sequence has been condensed into a compacted shape through the formation of loops using an origami tail. For example, the specificity of the interactions between complementary base pairs make DNA a useful material for the condensation of specific DNA target regions and sequences through design of specific target and cross-hybridization base sequences of origami tails, oligonucleotides or oligonucleotide primers. Nucleotides of the DNA may comprise biotinylated nucleotides, which can be used for creating and stabilizing scaffolds comprising streptavidin-labeled structures linked to the biotinylated nucleotides of one or more DNA strands. For example, the design of origami tails can be done by a computer program that calculates the placement of individual origami tail strands so that each binds to a specific region of the DNA template. An origami tail can be part of the 5'-end of a combined origami tail-oligonucleotide primer-complex, in which the oligonucleotide primer binds to a specific region of the DNA template. The origami tail-oligonucleotide primer-complex can be enzymatically extended with biotinylated nucleotides to form an extended origami tail-oligonucleotide primer-complex 1633. If the sequences of at least two 5'-end origami tails 1613 are complementary to each other, these origami tails can hybridize and condense the DNA template strands that have complementary sequences to the corresponding extended primers 1603. For example, as depicted in FIG. 16, the solution comprising the DNA target segment 1604 is heated to a temperature selected between about 80° C. and about 98° C., and then cooled to a temperature selected between about 20° C. and about 80° C. in the presence of origami tails or origami tail-oligonucleotide primer-complexes. For example, 80° C. means 80 degrees centigrade. As the DNA target segment cools, the origami tails or origami tail-oligonucleotide primer-complexes pull the long DNA target segment into the desired shape and condense it. See description of FIG. 16 in the specification.

In yet another embodiment of the present invention, a process may be used for forming loops and condensing the DNA, so as to stabilize the polynucleotide strand and thereby help to prevent physical and chemical damage to the polynucleotide, wherein the process may comprise using a member of the SMC (structural maintenance of chromosomes) family of protein complexes. SMC protein complexes include condensin, cohesin and the Smc5/6 complex (Ganji, 2018). The publication of Ganji et al. (2018) is incorporated herein in its entirety. The SMC protein complexes are useful for re-structuring genomes, for stabilizing DNA target segments and for capturing long polynucleotides for sequencing specific genomic regions. For example, a 1 nM concentration of *Saccharomyces cerevisiae* condensin complex and 5 mM ATP can be used to form a DNA loop in a double-stranded polynucleotide molecule. The speed of DNA loop formation depends on the concentration of ATP and the ability of condensin to bind and hydrolyze ATP.

In yet another embodiment of the present invention, a process may be used for condensing the DNA, so as to stabilize the polynucleotide strand and thereby help to prevent physical and chemical damage to the polynucleotide, wherein the process may comprise for example spreading heterochromatin protein 1 (HP1) proteins across large regions of the genome for compacting the underlying chromatin for condensing the DNA target segment. Other types of proteins that may be used for condensing the DNA target segment may include HP1α (wild-type, nPhos-HP1α, and HP1α (BPM)) and HP1β (Larson 2017). The publication of Larson et al. (2017) is incorporated herein in its entirety. Chromatin is found in two varieties: euchromatin and heterochromatin. Originally, the two forms were distinguished cytologically by how intensely they stained—the euchromatin is less intense, while heterochromatin stains intensely, indicating tighter packing. Heterochromatin is usually localized to the periphery of the nucleus. Despite this early dichotomy, recent evidence in both animals and plants has suggested that there are more than two distinct heterochromatin states, and it may in fact exist in four or five 'states', each marked by different combinations of epigenetic marks. Heterochromatin mainly consists of genetically inactive satellite sequences, and many genes are repressed to various extents, although some cannot be expressed in euchromatin at all. Both centromeres and telomeres are heterochromatic, as is the Barr body of the second, inactivated X-chromosome in a female. Heterochromatin is a tightly packed form of DNA or condensed DNA. Heterochromatin has been associated with several functions, from gene regulation to the protection of chromosome integrity; some of these roles can be attributed to the dense packing of DNA, which makes it less accessible to protein factors that usually bind DNA or its associated factors. For example, naked double-stranded DNA ends would usually be interpreted by the cell as damaged or viral DNA, triggering cell cycle arrest, DNA repair or destruction of the fragment, such as by endonucleases in bacteria. Some regions of chromatin are very densely packed with fibers that display a condition comparable to that of the chromosome at mitosis. Heterochromatin is generally clonally inherited; when a cell divides, the two daughter cells typically contain heterochromatin within the same regions of DNA, resulting in epigenetic inheritance. Variations cause heterochromatin to encroach on adjacent genes or recede from genes at the extremes of domains. Transcribable material may be repressed by being positioned (in cis) at these boundary domains. This gives rise to expression levels that vary from cell to cell, which may be demonstrated by position-effect variegation. Insulator sequences may act as a barrier in rare cases where constitutive heterochromatin and highly active genes are juxtaposed (e.g. the 5'HS4 insulator upstream of the chicken β-globin locus, and loci in two *Saccharomyces* spp.) (Heterochromatin, Wikipedia, 2019).

Condensation means a decrease in distance, elongation or occupied space of one or more polynucleotide molecules, typically through processes that involve folding, clustering, stacking, packing, binding, hybridization, or association with moieties or reagents that initiate condensation and increased proximity of segments from one or more polynucleotide molecules. Examples of such a condensation reagent or moiety are: DNA origami tails, DNA origami oligonucleotides, origami oligonucleotides comprising modified nucleotides, Cot-1 DNA, oligonucleotides comprising Cot-1, SINE, LINE, transposon or other types of repeat sequences, heterochromatin protein 1 (HP1), HP1α (wild-type, nPhos-HP1α, and HP1α (BPM)), HP1β, histones, spermidine, spermine, ethanol, streptavidin-labeled magnetic bead, streptavidin-labeled structure, cobalt(III) hexaamine ion $[Co(NH_3)_6]^{3+}$ or any combination thereof.

wikipedia.org/wiki/Spermidine,
ncbi.nlm.nih.gov/pubmed/28636604/,
researchgate.net/publication/13890685_Bridged cobalt_amine_complexes_induce_DNA_conformational_changes_effectively Surprising results of the present invention and various details for Region-Specific Extraction (RSE) embodiments of the present invention are discussed in below paragraphs.

RSE is able to selectively isolate genomic DNA target segments that are typically an order of magnitude larger (20 kb) than fragments produced by other target enrichment methods. Long DNA sequence reads can greatly simplify the assembly of complex genomes, in particular if the target region contains difficult sequence elements.

RSE requires only a small number of short (20-25 base) capture primers, typically spaced at distances of 3-8 kb, to pull down an extended region of interest. This makes it possible to enrich a region of interest even from potentially highly variable samples by creating a standard capture primer set based on known, conserved sequence elements.

RSE allows the identification of regions with unknown sequence around each capture point. It can therefore generate accurate and complete sequence information even for complex regions of interest for which no reliable reference genomes exist. Other target enrichment methods are unable capture a broad genomic context.

RSE generates a large proportion of enriched DNA target segments that can produce long read-length sequences across the targeted region of interest. Without prior fragmentation, most of the DNA after whole genome amplification (WGA) and RSE will be between 5 kb and 20 kb, with a portion over 40 kb. Forensic applications have reached linkage distances of 50 kb in each direction from a single capture point.

RSE achieves a capture efficiency of 20-30% per targeted locus even for very large DNA target segments based on active magnetic mixing (i.e. copy number of a locus enriched by RSE versus the copy number of this locus present in the input DNA). The material obtained after RSE is then typically amplified by whole genome amplification (WGA) in order to generate sufficient material for library preparation and sequencing.

For some applications, such as the use of RSE-enriched material on DNA arrays, no further amplification is required. The present invention advances next-generation sequencing platforms so as to allow a direct processing of very large DNA segments as produced by RSE in order to generate greatly increased DNA reads across a target region. For these instruments the intermediate WGA step, which is required for current NGS platforms, will no longer be needed.

The enzymatic primer extension step provides dual specificity based on the condition that each capture primer has to both (a) hybridize to the corresponding target sequence and (b) have a matching 3'-end in order for the primer to get extended.

Due to the ability of RSE to pull down large DNA target segments of the original template DNA, the amount of off-target material is high when compared with hybridization-based enrichment methods. Depending on the target region size, homology of target versus non-targeted regions and the duration of the WGA (Whole Genome Amplification) step, the amount of off-target material is typically over 50% and in some cases has been as high as 90%. This is in part due to the extension-based capture of very large fragments, which can lead to cross-hybridization of captured regions with other, non-targeted chromosomal segments that contain similar sequence, such as repeats, and the subsequent WGA amplification step, which can further introduce non-target sequences. Thus a periodic checking of the amount of DNA generated during the WGA step via a fluorescence-based method (i.e. Qubit or nanodrop 3300) is important and strictly limiting the WGA to the amount necessary for library preparation is helpful.

The distance of the primer extension step during RSE relative to read length is irrelevant for the linkage distances that can be achieved from each capture point provided the template DNA has sufficient length. The biotinylated nucleotides that are incorporated during the extension step serve as the handle for the pull-down of the original DNA template. Each primer isolates the original DNA template in both directions—upstream and downstream—from the capture point. The read length and uniformity of sequence coverage achieved are dependent on the capture primer locations, the amplification and library preparation steps performed after RSE and the selected NGS platform. RSE capture primers are typically spaced every 3-8 kb. This provides redundant capture across the region of interest even in cases where a capture primer may fail to perform optimally due to any unexpected issues, such as the presence of polymorphisms or other sequence variants at the capture point, DNA damage, secondary structure, or residual protein content. For short molecular weight DNA the distance between primers should be reduced. The recommended average RSE primer spacing varies between 1-20 kb depending on the application and the overall number of primers that are used in one extraction. For small target regions (50-250 kb) and a low number of capture primers (10-50), an average distance between neighboring primers of 3-5 kb is useful. For extended target regions (1-5 Mb) requiring a large number of capture primers (300+), the average distance between neighboring primers is 8-10 kb so as to ensure that adequate capture occurs across the target region by retaining a sufficient capture primer concentration with a low risk for primer dimer formation. For the typical design of a primer set, the region of interest can be first repeat-masked to identify unique sequence elements across the target region that can serve as capture points. These sequences are then reviewed for the possible presence of known mutations, which may either be avoided, incorporated or exploited during capture primer design.

A DNA region that contains unknown sequence can be "pulled down" provided that it contains or is flanked by known sequence elements that can be used to design unique capture primers (typically 15-25 bases are sufficient). For example, a 300 kb contiguous region that includes unknown sections of sequence can reliably be captured using about 40 capture points when working with input DNA of sufficiently high quality. Linkage distances of up to 50 kb in both directions from each capture point have been achieved in forensic applications.

In preferred embodiments of the present invention, the primer design process generates highly specific capture primer sets even for difficult genomic regions that do not allow for the placement of reliable primer sets with conventional repeat masking procedures.

Due to the enzymatic nature of the RSE capture process, even a very restrictive target sequence can in all likelihood be utilized to design a successful capture primer at this position.

The 5'-end of a primer can be allowed to partly overlap repetitive sequence as long as its 3'-end is unique.

The presence of a known polymorphism under the primer can be accepted by designing primers for both variants. If an allelic discrimination is desired, a known polymorphism can be positioned at the 3'-end of a capture primer (=HSE). In this case the enzymatic biotin labeling step and subsequent capture will only occur for primers whose 3'-ends match the targeted allele but not for variants that create a 3'-mismatch with the primers.

Region Specific Extraction (RSE) does not depend upon which direction the capture primers are oriented. The orientation of the primers does not affect the linkage distance in either direction from the capture point. One approach is to orient the direction of the primers so that the enzymatic extension occurs into the region that is of particular interest to the user. The extended capture primers are dissociated from the captured genomic DNA template in a buffer during the final resuspension step. Then the presence of any remaining extended, biotinylated strand does not interfere with any downstream assay, such as NGS or conventional Sanger sequencing, DNA arrays, or PCR/qPCR-based assays. Existing primers and validated primer sets, such as used for long-range PCR or qPCR, can often directly be used for RSE or as a starting point for the design of optimized RSE primers.

Preferably, the RSE capture primers are typically 15-25 bases long and designed to target unique sequence elements that distinguish the region of interest from the rest of the genomic material that is present in the sample. The capture primers should have a melting temperature of approximately 58° C. and a GC content of no more than 50%. It is advantageous to avoid GC-regions for increased capture efficiency. The RSE capture primers contain no biotin and are prepared at an equimolar ratio for a combined (total) concentration of 100 µM.

RSE primers can be placed on any target strand (+/−) in any direction/orientation that is most convenient, although self-complementary capture primers that are targeting the same sequence via opposite strands should obviously be avoided. A pairwise bioinformatic analysis of all primers should be conducted to eliminate possible primer dimers that might result in reduced capture. RSE is robust against the effects of possible primer dimer formation because, unlike in PCR, only a single extension step is required for capture and consequently no self-amplifying product is ever created.

A variation of RSE called region-specific amplification (RSA) uses a modified protocol to isothermally generate amplified products across the region of interest. The primer design in that case requires more diligence than for RSE. Allele-specific PCR primers can likewise be use as allele- or PSV-specific primers during haplotype-specific extraction HSE. Generally it is best to place a mismatch in order to select between two heterozygous alleles at the second-to-last position at the 3'-end of a capture primer. Additional primer design considerations apply to HSE that can greatly increase the degree of separation and overall capture efficiency, in particular when separating single-base differences in sequence (i.e. SNPs or PSVs).

RSE can selectively pull out large segments of native genomic DNA, and the methylation information on those segments is preserved. Methylated bases can directly be detected on certain newer NGS platforms, i.e. without the need for any bisulfite conversion. Enrichment control (after RSE and WGA/RSA but before NGS) is essentially done by "normal qPCR". It is preferred to design 4 to 5 qPCR assays in the target region and 4 to 5 qPCR assays for comparison to other non-enriched regions. It may be useful to design 6-7 qPCR primer pairs for both regions (on- and off-target) and then run them on normal genomic DNA, preferably in 2 or 3 concentrations to see they primer pairs behave linearly. Then the best assays are selected and take the CT values of the non-enriched, genomic DNA as a reference, which you then use to compare the CT values after enrichment. If you are measuring gene expression, qPCR will tell you how much of a specific mRNA there is in your samples. You amplify a small region of this mRNA with oligos and a fluorescent probe (if working with Taqman). The qPCR machine measures the intensity of fluorescence emitted by the probe at each cycle. During the first cycles, there is not enough fluorescence to be detected, but the reaction rapidly produces more and more amplicons and the fluorescence builds up. A qPCR curve has typically an exponential phase followed by a plateau phase. The Ct measure is a determined PCR cycle and represents the basic result of a qPCR experience. It is taken in the exponential phase, where the curve is linear. The threshold is placed in the linear phase, and the Ct is measured where the PCR curve crosses the threshold. The threshold is different for every qPCR assay (every gene tested), and is the same for all samples tested with this gene. The principle of the qPCR is based on the fact that at each PCR cycle, the number of PCR products doubles. If there is a difference of 2 cycles between two reactions (see figure), we can say that there is 4 times more copies in the pink reaction than in the orange reaction. Most of the time, a qPCR experiment will give a "relative expression", which is a variation of the expression of a gene between two samples. It's also possible to determine an absolute quantification (copy number) of a gene, but this technique requires a standard: typically the cloning of the cDNA of the gene into a vector.

The effect of the actual size of the target region on the calculation is not that significant for relatively small target regions, which is the case for most applications. If the target region is about 1% of the full genome the simple calculation above provides a very good estimate. The factors that are much more important to maximize the enrichment ratio (and increase coverage for a given sequence throughput) are DNA quality, age and handling, the design of the capture primers across the region and the ability to make them truly distinct from other known regions that may contain similar sequences. The presence of repeats or other complicating sequence elements in relative close proximity to the target points can create problems with additional background because they can cross-hybridize to similar repeats from non-targeted regions.

When working with very long DNA; alkaline denaturation and the use of larger volumes/lower DNA concentrations to minimize strand entanglement and the likelihood of cross-hybridization is important. Doing WGA after RSE and before NGS library prep is a useful protocol as it generates the minimum amounts of DNA you need for the library prep when the overall targeted regions are small. RSE is compatible with all common commercially available NGS platforms and available as a kit for manual or automated protocols. The most obvious advantage is gained on NGS instruments that generate very long DNA reads. However, NGS platforms that do not generate such long DNA reads are also able to use large input DNA segments from targeted regions to great advantage: even though the reads are shorter, they can now reliably detect linked sequence elements that are not accessible with other enrichment methods.

Completely unknown sequence can be pulled down as long as it is within reach (<20-50 kb) of at least one capture primer that is flanking this region. For input DNA that has been sheared, the isolation of 8 kb segments with any single primer is still possible. Unlike PCR-based methods, the linkage distance that can be obtained by RSE is not limited by the distance over which the enzymatic biotin-tagging step occurs during RSE: an extension of several hundred bases incorporates a sufficient number of biotins for a secure and reliable capture of much larger target template molecules.

Equally important, target capture by RSE is not limited to regions downstream of any capture point: any extended primer captures DNA segments that contain the target sequence, regardless of where it is located with respect to the remainder of the DNA molecule. If the DNA was pre-treated by specific restriction enzyme cuts or other sequence-specific sizing methods, the length of the captured DNA target segments will be limited by those boundaries in addition to any inherent size limitations that were present in the DNA starting material.

Downstream analysis of RSE is not limited to NGS. Insertion site or breakpoint mapping and copy number analysis can be done on a simple, array-based platform without requiring any additional amplification step after RSE. Mapping can be done through the use of DNA arrays after RSE and direct Cy3/Cy5 labeling of the captured material, without amplification. For some applications, RSE is close to being able to proceed directly from capture to sequencing, which will allow a user to directly see the methylation status of the captured region on some NGS platforms without the need for bisulfite conversion.

RSE capture primers for insertion site mapping can be designed to target either a pathogen's DNA, sections of the host genome that contain known breakpoints or sequences that are vulnerable to trigger carcinogenesis, or both. As long as the user can identify target-specific sequences in a region of interest, he or she can use those as capture points for the primers to pull out a large surrounding genomic context.

The size of the DNA that gets enriched by each primer depends primarily on the quality and molecular weight of the genomic starting material. There is a need to optimize factors that influence the available DNA size and quality because many samples have significant limitations in terms of length and quality, mostly because of age, extraction conditions and sometimes non-optimal storage and handling. DNA freshly isolated from blood, tissue or cell lines is ideal to be able to obtain very long linkage distances with each capture primer.

RSE capture primers are easily designed to avoid any known polymorphisms and repeat elements. They are selected to provide redundant and robust capture of a target region even if some of them fail due to unexpected changes in their respective target sequence. They can be very short (20-25 bases), which greatly facilitates the placement of capture primers within regions of high complexity, such as in heavily repeat-masked or duplicated regions that do not allow for a meaningful capture or amplification by other methods. In many cases existing primers for different purposes, such as LR-PCR or qPCR assays, can be used as RSE capture primers with slight or no modifications. We recommend designing a redundant set of primers that are relatively closely spaced (3 to 8 kb average distance) for reliable capture across a region. If any primers fail for unexpected reasons it is easy to re-design these and swap them out for better ones in the capture set.

For some embodiments of the present invention the DNA target segments have a length in terms of numbers of DNA bases wherein the number of DNA bases is selected from the group consisting of 3 to 5, 5 to 8, 8 to 12, 12 to 15, 15 to 25, 25 to 50, 50 to 100, 100 to 200, 200 to 350, 350 to 500, 500 to 1000, 1000 to 5000, 5000 to 10,000 and any combination thereof. The DNA target sequence is present within the sequence of a polynucleotide molecule. The term "DNA target segment" means DNA sequences of a length of 3 to 5, 5 to 8, 8 to 12, 12 to 15, 15 to 25, 25 to 50, 50 to 100, 100 to 200, 200 to 350, 350 to 500, and 500 to 1000 bases that are present within the sequence of a polynucleotide molecule.

Polynucleotide means is a biopolymer composed of a plurality of nucleotide monomers, wherein the number of monomers in the polynucleotide is selected from the group of 5, 6, 7, 8, 9, 10, 11, 12, 13, 14, 15, 16, 17, 18, 19, 20, 25, 30, 35, 40, 50, 60, 70, 80, 90, 100, 150, 200, 300, 500, 1000, 1738, 2000, 3000, 4000, 5000, 6000, 7000, 8000, 9000, 10,000, 20,000, 30,000, 50,000, 100,000, 200,000, 300,000, 400,000, 500,000, 1 million, 2 million, 3 million, 4 million, 5 million, 10 million, 20 million, 30 million, 40 million, 50 million, 100 million, 200 million, 300 million, 400 million, 500 million, 1 billion, 2 billion, 3 billion, 4 billion, 5 billion, and any combination thereof, and wherein the monomers in the polynucleotide covalently bonded in a chain. A polynucleotide may be selected from the group consisting of: a single-stranded polynucleotide, a double-stranded polynucleotide, a triple-stranded polynucleotide, and any combination thereof.

DNA (deoxyribonucleic acid) and RNA (ribonucleic acid) are examples of polynucleotides with distinct biological functions. Other examples of man-made polynucleotides are LNA (locked nucleic acid) and PNA (peptide nucleic acid).

In general, any population of polynucleotides can be used in the method. For example, polynucleotides can be selected from the group of DNA or RNA, and can include genomic DNA, plasmid DNA, amplified DNA, cDNA, total cellular RNA, hnRNA, polyA+-containing RNA, and any combination thereof. Polynucleotides can be from a single unicellular or eukaryotic organism. For example, the polynucleotide can be obtained from a mammalian organism such as a human, a plant, or an animal, or bacteria, or archaea, or fungi, or viruses. Examples of nucleic acid-based nucleic acid derivatives include, e.g., an oligonucleotide, oligopeptide nucleic acid (PNA), oligo-LNA, or a ribozyme.

Biotin is an example of a substituent on a nucleotide, wherein the nucleotide is used to extend a polynucleotide primer. Streptavidin is an example of a substituent which is used to label a structure. In some embodiments, binding of the biotin to the streptavidin is a preferred means for linking the nucleotide and the extended polynucleotide primer to the structure which has been labeled by the streptavidin. The streptavidin-labeled structure is selected from the group consisting of: a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, a streptavidin-labeled cluster, and any combination thereof, wherein the streptavidin-labeled cluster may be comprised a plurality of individual streptavidin-labeled structures selected from the group consisting of a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, and any combination thereof.

In preferred embodiments of the invention, the molecular binding combination is a biotin-streptavidin binding combination, wherein the first binding partner of the molecular binding combination is biotin and the second binding partner is streptavidin. In alternative embodiments of the invention, other first binding partner and second binding partner are useful as molecular binding combinations and may be selected from the group consisting of ligands, receptors, antibodies, haptens, enzymes, chemical groups recognizable by antibodies or aptamers, fluorescein, digoxigenin, 2,4-Dinitrophenol, proteins, nucleic acids, carbohydrates, lipids, small organic molecules and any combination thereof.

Examples of second binding partners may be selected from the group consisting of particles, beads, magnetic beads, optically trapped beads, microtiter plates, glass slides, papers, test strips, gels, other matrices, nitrocellulose, nylon and any combination thereof.

The published US patent application of Dapprich, US 2001/0031467A1, Barnes U.S. Pat. No. 7,057,076, and Dapprich, U.S. Pat. No. 8,465,925 are herein incorporated by reference in their entirety.

A polynucleotide primer may be elongated by the use of non-terminating biotinylated nucleotides. It is significant that the extension of the polynucleotide primer produces numerous binding events between multiple biotins and a streptavidin-labeled structure located over a potentially long distance of the DNA target segment: A strong attachment is formed by multiple binding events between multiple biotins and a streptavidin-labeled structure. Due to the twisted helical structure of double-stranded DNA, the DNA target fragment becomes intertwined with the primer extension product containing biotinylated nucleotides, thereby topologically linking the DNA target segment to the streptavidin-labeled structure, provided the distance of the elongated region is significantly greater than the average distance between incorporated biotinylated nucleotides and the pitch of the helix (about 3.4 nm or ten base pairs per turn).

In preparation for DNA target segment capture and separation it is advantageous to achieve fast on-rates as well as high selectivity and efficiency of binding between biotinylated nucleotides and the streptavidin-labeled structure. If small DNA target segments are captured, it is sufficient to carry out the binding step by incubation on a rotator at room temperature. In the case of increasingly large DNA target segments, relative motion between the targeted DNA target segments and the streptavidin-labeled structure increases capture efficiency and reduces time required for efficient capture. Relative motion between the targeted DNA target segments and the streptavidin-labeled structure can be achieved by different means, for instance by moving magnetic beads or streptavidin-labeled structures used for capturing back and forth through the solution by repeated precipitation and resuspension, or by magnetically or electrophoretically generated movement. Examples of magnetically induced relative motion are a magnetic field gradient that attracts the beads through the reaction solution, or a rotating homogeneous magnetic field that generates clusters of magnetic beads or streptavidin-labeled structures that rotate with the rotating magnetic field with respect to the reaction solution.

Non-specific binding of non-targeted polynucleotide fragments to the magnetic beads or streptavidin-labeled structures can be reduced by exposing the surface of a streptavidin-labeled structure to a solution containing components that saturate unspecific binding sites on the surface of the streptavidin-labeled structures. As an example, a blocking buffer "MBSB" can be used to suppress unspecific binding to beads (2.8 µm magnetic beads 'Dynabeads M-280 Streptavidin', Dynal AS, Oslo, Norway, or 1 µm polystyrene beads ('Streptavidin Coated Latex'), Interfacial Dynamics Corporation, Portland, Oreg.) with the result that biotinylated DNA target segments are readily amplified by PCR compared to undetectable levels of product of non-biotinylated DNA fragments on both types of beads (magnetic or polystyrene).

An example of a buffered liquid medium is buffer 'MBSA', which is a solution containing 10 mM Tris pH 7.5, 2 mM EDTA, 0.2% Tween-20, 1 M NaCl, 5 µg/ml BSA, 1.25 mg/ml 'carnation' dried milk (Nestle), and 1 mg/ml glycine. Magnetic beads or streptavidin-labeled structures are washed twice in 1 ml "MBSA" by briefly vortexing and precipitating. Precipitation is performed with a particle collection magnet (Polysciences, Warrington, Pa.) for 1 min. (magnetic beads or streptavidin-labeled structures), or by centrifugation at 13,000 rpm on a table-top centrifuge for 3 min. (polystyrene beads or streptavidin-labeled structures).

Specification support for original claims includes the below section.

We claim: 1. A method for capturing a polynucleotide comprising a DNA target segment from a population of polynucleotide molecules, the method comprising the steps of:

providing a mixture comprising the population of the polynucleotide molecules, one or more polynucleotide primers, nucleotides, biotinylated nucleotides, a polymerase enzyme and a buffered liquid medium;

denaturing the polynucleotide molecules in the mixture so as to create single stranded portions of the polynucleotide molecules which can be accessible to the polynucleotide primers;

hybridizing the polynucleotide primers to the polynucleotide comprising the DNA target segment;

creating an extended polynucleotide primer by using the nucleotides, the biotinylated nucleotides and the polymerase enzyme as a means for labeling with biotin and increasing the extent of hybridization of the extended polynucleotide primer to the polynucleotide comprising the DNA target segment;

adding streptavidin-labeled magnetic beads to the mixture;

using a magnetic field to move the streptavidin-labeled magnetic beads relative to the buffered liquid medium as a means for increasing binding of the biotinylated nucleotides of the extended polynucleotide primer to the streptavidin-labeled magnetic beads;

using either a rotation of the magnetic field relative to the mixture or a rotation of the mixture relative to the magnetic field for causing a streptavidin-labeled magnetic bead rotation in the buffered liquid medium as a means for performing the steps of increasing the binding of the biotinylated nucleotides of the extended polynucleotide primer to the streptavidin-labeled magnetic beads and increasing the winding of the biotinylated nucleotides of the extended polynucleotide primer onto the streptavidin-labeled magnetic beads, so as to increase the probability of capturing a long polynucleotide comprising a DNA target segment and so as to increase the probability of preventing damage to the long polynucleotide comprising a DNA target segment; and using the magnetic field to collect the streptavidin-labeled magnetic beads so as to capture the polynucleotide comprising the DNA target segment which is bound to the streptavidin-labeled magnetic beads.

2. The method according to claim 1, wherein the winding of the biotinylated nucleotides of the extended polynucleotide primer onto the streptavidin-labeled magnetic beads lessens entanglement of the captured polynucleotide with the population of polynucleotides so as to avoid an increase in off-target capture during capturing of the polynucleotide comprising the DNA target segment from a population of polynucleotide molecules.

3. The method according to claim 1, wherein the polynucleotide primer is capable of binding to the same polynucleotide strand or to two or more separate polynucleotide strands.

4. The method according to claim 1, wherein two different polynucleotide primers have two complementary origami tails which are capable of binding to each other, so as to result into the condensation of two separate DNA target segments which are located on at least one polynucleotide strand and which are hybridized to two different polynucleotide primers.

5. The method according to claim 1, wherein a polynucleotide may comprise two origami tails and may be capable of binding to at least two different DNA target segments so as to result into the condensation of two different DNA target segments which are located on at least one polynucleotide strand.

6. The method according to claim 1, wherein the polynucleotide primer has a length of between about 15 to about 30 DNA bases and polynucleotide primers designed to hybridize to adjacent DNA target segments are spaced at a distance of between about 3 to about 8 kilobases, to pull down the polynucleotide comprising the DNA target segment from a population of polynucleotide molecules.

7. The method according to claim 1, where the step of using either a rotation of the magnetic field relative to the mixture or a rotation of the mixture relative to the magnetic field for causing a streptavidin-labeled magnetic bead rotation in the buffered liquid medium comprises a streptavidin-labeled structure 8. The method according to claim 1, wherein condensation of at least one polynucleotide is effected by a condensation reagent or moiety selected from the group consisting of: DNA origami tails, DNA origami oligonucleotides, origami oligonucleotides comprising modified nucleotides, Cot-1 DNA, oligonucleotides comprising Cot-1, SINE, LINE, transposon or other types of repeat sequences, heterochromatin protein 1 (HP1), HP1α (wild-type, nPhos-HP1α, and HP1α (BPM)), HP1β, histones, spermidine, spermine, ethanol, streptavidin-labeled magnetic bead, streptavidin-labeled structure, cobalt(III) hexaamine ion [Co (NH$_3$)$_6$]$^{3+}$ or any combination thereof.

9. The method according to claim 1, wherein the polynucleotide primer has a number of nucleotide bases selected from the group consisting of 5 bases, 6 bases, 7 bases, 8 bases, 9 bases, 10 bases, 15 bases, 16 bases, 17 bases, 18 bases, 19 bases, 20 bases, 21 bases, 22 bases, 23 bases, 24 bases, 25 bases, 26 bases, 27 bases, 28 bases, 29 bases, 30 bases, 31q bases, 32 bases, 33 bases, 34 bases, 35 bases, 36 base, 37 bases, 38 bases, 39 base, 40 bases, 41 base, 42 bases, 43 bases, 44 bases, 45 bases, 46 bases, 47 bases, 48 bases, 49, bases, 50 bases and any combination thereof.

10. The method according to claim 1, wherein the polymerase enzyme is selected from the group consisting of Φ29 DNA polymerase, BST 2.0 polymerase, and a combination thereof.

11. The method according to claim 10, wherein the Φ29 polymerase is used at temperature of between 40° C.-50° C.

12. The method according to claim 1, wherein the biotinylated nucleotide base. is added to the DNA sequence during primer extension process at a frequency selected from the group consisting of one biotinylated nucleotide per 5 nucleotide bases of DNA primer extension, one biotinylated nucleotide per 6 nucleotide bases of DNA primer extension, one biotinylated nucleotide per 7 nucleotide bases of DNA primer extension, one biotinylated nucleotide per 8 nucleotide bases of DNA primer extension, one biotinylated nucleotide per 9 nucleotide bases of DNA primer extension, one biotinylated nucleotide per 10 nucleotide bases of DNA primer extension, one biotinylated nucleotide per 15 nucleotide bases of DNA primer extension, one biotinylated nucleotide per 20 nucleotide bases of DNA primer extension, one biotinylated nucleotide per 30 nucleotide bases of DNA primer extension, one biotinylated nucleotide per 40 nucleotide bases of DNA primer extension, one biotinylated nucleotide per 50 nucleotide bases of DNA primer extension, one biotinylated nucleotide per 60 nucleotide bases of DNA primer extension, one biotinylated nucleotide per 70 nucleotide bases of DNA primer extension, one biotinylated nucleotide per 80 nucleotide bases of DNA primer extension, one biotinylated nucleotide per 90 nucleotide bases of DNA primer extension, one biotinylated nucleotide per 100 nucleotide bases of DNA primer extension, and any combination thereof.

13. The method according to claim 1, wherein a temperature range during the hybridization to specific genomic regions of interest is selected from the group consisting of 20° C. to 90° C., 25° C. to 80° C., 30° C. to 70° C., 35° C. to 65° C., 40° C. to 60° C., 45° C. to 65° C., 45° C. to 60° C., 50° C. to 60° C., 55° C. to 65° C., 55° C. to 60° C., and any combination thereof.

14. The method according to claim 1, further comprising using non-extendable blocking oligonucleotides which is longer or has a higher Guanosine and Cytosine content than the polynucleotide primer which is used.

15. The method according to claim 1, further comprising performing a pre-extension with terminating nucleotides which are dideoxynucleotides triphosphates selected from the group consisting of ddATP, ddTTP, ddCTP, ddGTP, and any combination thereof so as to repair a strand break and terminate free 3'-polynucleotide ends so as to reduce off-target capture.

16. The method according to claim 1, further comprising using a nucleotide base selected from the group consisting of a 5' Bromo dU, a 5' 2-Aminopurine, a 3' 2-Aminopurine, a 5' 2,6-Diaminopurine (2-Amino-dA), a 3' 2,6-Diaminopurine (2-Amino-dA), a 5' deoxyUridine, a 3' deoxyUridine, an Inverted DT, an Inverted Dideoxy-T, a Dideoxy-C, a 5-Methyl dC, a deoxyInosine, a Super T, a Super G, Locked Nucleic Acids (LNA's), a 5-Nitroindole, a 2'-O-Methyl RNA Bases, a Hydroxmethyl dC, an Iso-dG, an Iso-dC, a 5' Fluoro C, a 5' Fluoro U, a 5' Fluoro A, a 5' Fluoro G, a 5' 2-MethoxyEthoxy A, a 5' 2-MethoxyEthoxy MeC, a 5' 2-MethoxyEthoxy G, a 5' 2-MethoxyEthoxy T, a 3' Fluoro C, a 3' Fluoro U, a 3' Fluoro A, a 3' Fluoro G, a 3' 2-MethoxyEthoxy A, a 3' 2-MethoxyEthoxy MeC, a 3' 2-MethoxyEthoxy G, a 3' 2-MethoxyEthoxy T, and a combination thereof.

17. The method according to claim 1, wherein a nucleotide linker is selected from the group consisting of Acrydite™, Adenylation, Azide NHS ester, Digoxigenin NHS Ester, Cholesterol-TEG, I-Linker™, biotin, streptavidin, and any combination thereof.

18. The method according to claim 1, wherein the buffered liquid medium is a buffer MBSA which comprises an aqueous solution comprising 10 mM Tris pH 7.5, 2 mM EDTA, 0.2% Tween-20, 1 M NaCl, 5 µg/ml BSA, 1.25 mg/ml Nestle Carnation dried milk, and 1 mg/ml glycine.

19. The method according to claim 1, wherein the polynucleotide molecules can be selected from the group consisting of a DNA sample, a genomic DNA sample, a plasmid DNA sample, an amplified DNA sample, a cDNA, a mitochondrial nucleotide sample, an oligonucleotide sample, an oligo-peptide nucleic acid (PNA) sample, an oligo-LNA, and any combination thereof, and wherein the polynucleotide molecules may be obtained from a human, a mammal, a plant, a bacteria, an archaea, a fungi, a viruses, a single biological cell, a biological tissue, a biological organ, and any combination thereof.

20. A method for capturing a polynucleotide comprising a DNA target segment from a population of polynucleotide molecules, the method comprising the steps of:
provproviding a mixture comprising the population of the polynucleotide molecules, one or more polynucleotide primers, nucleotides, biotinylated nucleotides, a polymerase enzyme and a buffered liquid medium;
denaturing the polynucleotide molecules in the mixture so as to create single stranded portions of the polynucleotide molecules which can be accessible to the polynucleotide primers;
hybridizing the polynucleotide primers to the polynucleotide comprising the DNA target segment;
creating an extended polynucleotide primer by using the nucleotides, the biotinylated nucleotides and the polymerase enzyme as a means for labeling with biotin and increasing the extent of hybridization of the extended polynucleotide primer to the polynucleotide comprising the DNA target segment;
adding streptavidin-labeled magnetic structures to the mixture;
using a magnetic field to move the streptavidin-labeled magnetic structures relative to the buffered liquid medium as a means for increasing binding of the biotinylated nucleotides of the extended polynucleotide primer to the streptavidin-labeled magnetic structures;
using either a rotation of the magnetic field relative to the mixture or a rotation of the mixture relative to the magnetic field for causing a streptavidin-labeled magnetic structures rotation in the buffered liquid medium as a means for performing the steps of increasing the binding of the biotinylated nucleotides of the extended polynucleotide primer to the streptavidin-labeled magnetic structures and increasing the winding of the biotinylated nucleotides of the extended polynucleotide primer onto the streptavidin-labeled magnetic structures, so as to increase the probability of capturing a long polynucleotide comprising a DNA target segment and so as to increase the probability of preventing damage to the long polynucleotide comprising a DNA target segment; and
using the magnetic field to collect the streptavidin-labeled magnetic structures so as to capture the polynucleotide comprising the DNA target segment which is bound to the streptavidin-labeled magnetic structures
wherein the streptavidin-labeled structures are selected from the group consisting of:
a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, a streptavidin-labeled cluster, and any combination thereof, wherein the streptavidin-labeled cluster may be comprised a plurality of individual streptavidin-labeled structures selected from the group consisting of a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, and any combination thereof.

Certain terminology may be used in the following description for convenience only and is not limiting. The words "lower" and "upper" and "top" and "bottom" designate directions in the drawings to which reference is made. The terminology includes the words above specifically mentioned, derivatives thereof and words of similar import. Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein. It will be appreciated by those skilled in the art that changes could be made to the embodiments described above without departing from the broad inventive concept thereof. It is understood, therefore, that this invention is not limited to the particular embodiments disclosed, but it is unintended to cover modifications within the spirit and scope of the present invention as defined by the appended claims.

We claim:

1. A method for capturing a long polynucleotide comprising a DNA target segment from a population of polynucleotide molecules, the method comprising the steps of: providing a mixture comprising the population of the polynucleotide molecules, one or more polynucleotide primers, nucleotides, biotinylated nucleotides, a polymerase enzyme and a buffered liquid medium; denaturing the polynucleotide molecules in the mixture so as to create single stranded portions of the polynucleotide molecules which can be accessible to the polynucleotide primers; hybridizing the polynucleotide primers to the polynucleotide comprising the DNA target segment; creating an extended polynucleotide primer by using the nucleotides, the biotinylated nucleotides and the polymerase enzyme as a means for labeling with biotin and increasing the extent of hybridization of the extended polynucleotide primer to the polynucleotide comprising the DNA target segment; adding streptavidin-labeled magnetic beads to the mixture; using a magnetic field to move the streptavidin-labeled magnetic beads relative to the buffered liquid medium as a means for increasing binding of the biotinylated nucleotides of the extended polynucleotide primer to the streptavidin-labeled magnetic beads; using either a rotation of the magnetic field relative to the mixture or a rotation of the mixture relative to the magnetic field for causing a streptavidin-labeled magnetic bead rotation in the buffered liquid medium as a means for performing the steps of increasing the binding of the biotinylated nucleotides of the extended polynucleotide primer to the streptavidin-labeled magnetic beads and increasing the winding of the biotinylated nucleotides of the extended polynucleotide primer onto and around the streptavidin-labeled magnetic beads, so as to increase the probability of capturing a long polynucleotide comprising the DNA target segment, wherein the long polynucleotide is at least 10 kb, and so as to increase the probability of preventing damage to the long polynucleotide comprising the DNA target segment; and using the magnetic field to collect the streptavidin-labeled magnetic beads so as to capture the polynucleotide comprising the DNA target segment which is bound to the streptavidin-labeled magnetic beads.

2. The method according to claim 1, wherein the winding of the biotinylated nucleotides of the extended polynucleotide primer onto the streptavidin-labeled magnetic beads lessens entanglement of the captured long polynucleotide with the population of polynucleotides so as to avoid an increase in off-target capture during capturing of the polynucleotide comprising the DNA target segment from a population of polynucleotide molecules.

3. The method according to claim 1, wherein the polynucleotide primer is capable of binding to the same polynucleotide strand or to two or more separate polynucleotide strands.

4. The method according to claim 1, wherein two different polynucleotide primers have two complementary origami tails which are capable of binding to each other, so as to result into the condensation of two separate DNA target segments which are located on at least one polynucleotide strand and which are hybridized to two different polynucleotide primers.

5. The method according to claim 1, wherein a polynucleotide may comprise two origami tails and may be capable of binding to at least two different DNA target segments so as to result into the condensation of two different DNA target segments which are located on at least one polynucleotide strand.

6. The method according to claim 1, wherein the polynucleotide primer has a length of between about 15 to about 30 DNA bases and polynucleotide primers designed to hybridize to adjacent DNA target segments are spaced at a distance of between about 3 to about 8 kilobases, to pull down the polynucleotide comprising the DNA target segment from a population of polynucleotide molecules.

7. The method according to claim 1, where the step of using either a rotation of the magnetic field relative to the mixture or a rotation of the mixture relative to the magnetic field for causing a streptavidin-labeled magnetic bead rotation in the buffered liquid medium comprises a streptavidin-labeled structure.

8. The method according to claim 1, wherein condensation of at least one polynucleotide is effected by a condensation reagent or moiety selected from the group consisting of: DNA origami tails, DNA origami oligonucleotides, origami oligonucleotides comprising modified nucleotides, Cot-1 DNA, oligonucleotides comprising Cot-1, SINE, LINE, transposon or other types of repeat sequences, heterochromatin protein 1 (HP1), HP1α (wild-type, nPhos-HP1α, and HP1α(BPM)), HP1β, histones, spermidine, spermine, ethanol, streptavidin-labeled magnetic bead, streptavidin-labeled structure, cobalt(III) 16 examine ion $[Co(NH_3)_6]^{3+}$ or any combination thereof.

9. The method according to claim 1; wherein the polynucleotide primer has a number of nucleotide bases selected from the group consisting of 5 bases, 6 bases, 7 bases, 8 bases, 9 bases, 10 bases, 15 bases, 16 bases, 17 bases, 18 bases, 19 bases; 20 bases, 21 bases; 22 bases, 23 bases; 24 bases, 25 bases, 26 bases, 27 bases; 28 bases, 29 bases, 30 bases, 31 q bases, 32 bases, 33 bases, 34 bases, 35 bases; 36 base, 37 bases, 38 bases, 39 base, 40 bases, 41 base, 42 bases, 43 bases, 44 bases, 45 bases, 46 bases, 47 bases, 48 bases, 49, bases, 50 bases and any combination thereof.

10. The method according to claim 1, wherein the polymerase enzyme is selected from the group consisting of Φ29 DNA polymerase, BST 2.0 polymerase, and a combination thereof.

11. The method according to claim 10, wherein the Φ29 polymerase is used at temperature of between 40° C.-50° C.

12. The method according to claim 1, wherein the biotinylated nucleotide base is added to the DNA sequence during primer extension process at a frequency selected from the group consisting of one biotinylated nucleotide per 5 nucleotide bases of DNA primer extension, one biotinylated nucleotide per 6 nucleotide bases of DNA primer extension, one biotinylated nucleotide per 7 nucleotide bases of DNA primer extension, one biotinylated nucleotide per 8 nucleotide bases of DNA primer extension, one biotinylated nucleotide per 9 nucleotide bases of DNA primer extension, one biotinylated nucleotide per 10 nucleotide bases of DNA primer extension, one biotinylated nucleotide per 15 nucleotide bases of DNA primer extension, one biotinylated nucleotide per 20 nucleotide bases of DNA primer extension, one biotinylated nucleotide per 30 nucleotide bases of DNA primer extension, one biotinylated nucleotide per 40 nucleotide bases of DNA primer extension, one biotinylated nucleotide per 50 nucleotide bases of DNA primer extension, one biotinylated nucleotide per 60 nucleotide bases of DNA primer extension, one biotinylated nucleotide per 70 nucleotide bases of DNA primer extension, one biotinylated nucleotide per 80 nucleotide bases of DNA primer extension, one biotinylated nucleotide per 90 nucleotide bases of DNA primer extension, one biotinylated nucleotide per 100 nucleotide bases of DNA primer extension, and any combination thereof.

13. The method according to claim 1, wherein a temperature range during the hybridization to specific genomic regions of interest is selected from the group consisting of 20° C. to 90° C., 25° C. to 80° C., 30° C. to 70° C., 35° C. to 65° C., 40° C. to 60° C., 45° C. to 65° C., 45° C. to 60° C., 50° C. to 60° C., 55° C. to 65° C., 55° C. to 60° C., and any combination thereof.

14. The method according to claim 1, further comprising using non-extendable blocking oligonucleotides which is longer or has a higher Guanosine and Cytosine content than the polynucleotide primer which is used.

15. The method according to claim 1, further comprising performing a pre-extension with terminating nucleotides which are dideoxynucleotides triphosphates selected from the group consisting of ddATP, ddTTP, ddCTP, ddGTP, and any combination thereof so as to repair a strand break and terminate free 3'-polynucleotide ends so as to reduce off-target capture.

16. The method according to claim 1, further comprising using a nucleotide base selected from the group consisting of a 5' Bromo dU, a 5' 2-Aminopurine, a 3' 2-Aminopurine, a 5' 2,6-Diaminopurine (2-Amino-dA), a 3' 2,6-Diaminopurine (2-Amino-dA), a 5' deoxyUridine, a 3' deoxyUridine, an Inverted DT, an Inverted Dideoxy-T, a Dideoxy-C, a 5-Methyl dC, a deoxyInosine, a Super T, a Super G, Locked Nucleic Acids (LNA's), a 5-Nitroindole, a 2'-O-Methyl RNA Bases, a Hydroxmethyl dC, an Iso-dG, an Iso-dC, a 5' Fluoro C, a 5' Fluoro U, a 5' Fluoro A, a 5' Fluoro G, a 5' 2-MethoxyEthoxy A, a 5' 2-MethoxyEthoxy MeC, a 5' 2-MethoxyEthoxy G, a 5' 2-MethoxyEthoxy T, a 3' Fluoro C, a 3' Fluoro U, a 3' Fluoro A, a 3' Fluoro G, a 3' 2-MethoxyEthoxy A, a 3' 2-MethoxyEthoxy MeC, a 3' 2-MethoxyEthoxy G, a 3' 2-MethoxyEthoxy T, and a combination thereof.

17. The method according to claim 1, wherein a nucleotide linker is selected from the group consisting of Acrydite™, Adenylation, Azide NHS ester, Digoxigenin NHS Ester, Cholesterol-TEG, I-Linker™, biotin, streptavidin, and any combination thereof.

18. The method according to claim 1, wherein the buffered liquid medium is a buffer MBSA which comprises an aqueous solution comprising 10 mM Iris pH 7.5, 2 mM EDTA, 0.2% Tween-20, 1 M NaCl, 5 µg/ml BSA, 1.25 mg/ml Nestle Carnation dried milk, and 1 mg/ml glycine.

19. The method according to claim 1, wherein the polynucleotide molecules can be selected from the group consisting of a DNA sample, a genomic DNA sample, a plasmid DNA sample, an amplified DNA sample, a cDNA, a mitochondrial nucleotide sample, an oligonucleotide sample, an oligo-peptide nucleic acid (PNA) sample, an oligo-LNA, and any combination thereof, and wherein the polynucleotide molecules may be obtained from a human, a mammal, a plant, a bacteria, an archaea, a fungi, a viruses, a single biological cell, a biological tissue, a biological organ, and any combination thereof.

20. A method for capturing a long polynucleotide comprising a DNA target segment from a population of polynucleotide molecules, the method comprising the steps of: providing a mixture comprising the population of the polynucleotide molecules, one or more polynucleotide primers, nucleotides, biotinylated nucleotides, a polymerase enzyme and a buffered liquid medium; denaturing the polynucleotide molecules in the mixture so as to create single stranded portions of the polynucleotide molecules which can be accessible to the polynucleotide primers; hybridizing the polynucleotide primers to the polynucleotide comprising the DNA target segment; creating an extended polynucleotide primer by using the nucleotides, the biotinylated nucleotides and the polymerase enzyme as a means for labeling with biotin and increasing the extent of hybridization of the extended polynucleotide primer to the polynucleotide comprising the DNA target segment; adding streptavidin-labeled magnetic structures to the mixture; using a magnetic field to move the streptavidin-labeled magnetic structures relative to the buffered liquid medium as a means for increasing binding of the biotinylated nucleotides of the extended polynucleotide primer to the streptavidin-labeled magnetic structures; using either a rotation of the magnetic field relative to the mixture or a rotation of the mixture relative to the magnetic field for causing a streptavidin-labeled magnetic structures rotation in the buffered liquid medium as a means for performing the steps of increasing the binding of the biotinylated nucleotides of the extended polynucleotide primer to the streptavidin-labeled magnetic structures and increasing the winding of the biotinylated nucleotides of the extended polynucleotide primer onto and around the streptavidin-labeled magnetic structures, so as to increase the probability of capturing a long polynucleotide comprising the DNA target segment and so as to increase the probability of preventing damage to the long polynucleotide comprising the DNA target segment, wherein the long polynucleotide is at least 10 kb; and using the magnetic field to collect the streptavidin-labeled magnetic structures so as to capture the polynucleotide comprising the DNA target segment which is bound to the streptavidin-labeled magnetic structures wherein the streptavidin-labeled structures are selected from the group consisting of: a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, a streptavidin-labeled cluster, and any combination thereof, wherein the streptavidin-labeled cluster may be comprised a plurality of individual streptavidin-labeled structures selected from the group consisting of a streptavidin-labeled superparamagnetic bead, streptavidin-labeled superparamagnetic particle, streptavidin-labeled disk, streptavidin-labeled rod, streptavidin-labeled sheet, streptavidin-labeled hollow cylinder, streptavidin-labeled polysaccharide, and any combination thereof.

21. The method according to claim 1, wherein each of the magnetic beads have a diameter of about one micron and the rotation of each magnetic bead is at least one winding turn to increase the binding and winding of the biotinylated nucleotides of the extended polynucleotide primer around the magnetic bead.

22. The method according to claim 1, wherein the long polynucleotide is from about 10 kb to about 1 Mb in length.

* * * * *